(12) United States Patent
Flaherty et al.

(10) Patent No.: US 9,345,858 B2
(45) Date of Patent: *May 24, 2016

(54) CATHETERS, SYSTEMS AND METHODS FOR PERCUTANEOUS IN SITU ARTERIO-VENOUS BYPASS

(71) Applicant: Medtronic Vascular, Inc., Santa Rosa, CA (US)

(72) Inventors: J. Christopher Flaherty, Los Altos, CA (US); Jason B. Whitt, San Francisco, CA (US); Patrick E. Macaulay, San Jose, CA (US); David R. Tholfsen, San Francisco, CA (US); John T. Garibotto, Palo Alto, CA (US); Philip C. Evard, Palo Alto, CA (US); Joshua Makower, Los Altos, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/967,849

(22) Filed: Aug. 15, 2013

(65) Prior Publication Data

US 2014/0180222 A1    Jun. 26, 2014

Related U.S. Application Data

(60) Continuation of application No. 10/370,429, filed on Feb. 20, 2003, now Pat. No. 8,585,596, which is a division of application No. 09/282,276, filed on Mar. 31, 1999, now Pat. No. 6,544,230.

(60) Provisional application No. 60/080,196, filed on Mar. 31, 1998.

(51) Int. Cl.
*A61M 25/01*     (2006.01)
*A61B 17/3207*   (2006.01)
(Continued)

(52) U.S. Cl.
CPC ............ *A61M 25/0108* (2013.01); *A61B 17/22* (2013.01); *A61B 17/3207* (2013.01); *A61B 2017/00252* (2013.01);
(Continued)

(58) Field of Classification Search
CPC ..................... A61M 25/0108; A61M 25/0105; A61M 2205/0175; A61M 2205/0177; A61M 2205/1061; A61M 2205/0197; A61M 2205/018; A61B 17/22; A61B 17/3207; A61B 2017/22077; A61B 2017/00252; A61B 2017/00455; A61B 19/54; A61B 2019/5425; A61B 2019/5483
USPC ............... 604/96.01, 102.01, 102.02, 102.03, 604/523, 532, 103.01, 103.02, 104–109
See application file for complete search history.

(56) References Cited

U.S. PATENT DOCUMENTS 4,739,768 A    4/1988   Engelson
4,769,005 A    9/1988   Ginsburg et al.
(Continued)

FOREIGN PATENT DOCUMENTS

WO    WO96/30072    10/1996
WO    WO9701988     1/1997
WO    WO97/27897    8/1997

*Primary Examiner* — Andrew Gilbert

(57) ABSTRACT

A system of catheter devices and methods for forming channels or passageways between a luminal anatomical structure (e.g., a blood vessel) and a target location (e.g., another blood vessel, an organ, a mass of tissue, etc.) for the purpose of rerouting blood flow or for delivering a substance or instrument, etc. to the target location.

13 Claims, 32 Drawing Sheets

(51) Int. Cl.
*A61B 17/22* (2006.01)
*A61B 17/00* (2006.01)
*A61B 19/00* (2006.01)

(52) U.S. Cl.
CPC ............... *A61B 2017/00455* (2013.01); *A61B 2017/22077* (2013.01); *A61B 2019/528* (2013.01); *A61B 2019/5425* (2013.01)

(56) References Cited

U.S. PATENT DOCUMENTS

| | | | |
|---|---|---|---|
| 4,794,931 A | | 1/1989 | Yock |
| 4,817,613 A | | 4/1989 | Jaraczewski et al. |
| 4,861,336 A | | 8/1989 | Helzel |
| 4,950,267 A | | 8/1990 | Ishihara et al. |
| 4,997,431 A | | 3/1991 | Isner et al. |
| 5,054,492 A | * | 10/1991 | Scribner et al. ............... 600/463 |
| 5,055,109 A | | 10/1991 | Gould et al. |
| 5,106,386 A | | 4/1992 | Isner et al. |
| 5,171,232 A | | 12/1992 | Castillo et al. |
| 5,190,528 A | | 3/1993 | Fonger et al. |
| 5,269,326 A | | 12/1993 | Verrier |
| 5,287,861 A | | 2/1994 | Wilk |
| 5,312,341 A | | 5/1994 | Turi |
| 5,330,496 A | | 7/1994 | Alferness |
| 5,354,279 A | * | 10/1994 | Hofling ................... 604/164.12 |
| 5,366,490 A | | 11/1994 | Edwards et al. |
| 1,537,067 A | | 12/1994 | Edwards et al. |
| 5,389,096 A | | 2/1995 | Aita et al. |
| 5,409,019 A | | 4/1995 | Wilk |
| 5,429,144 A | | 7/1995 | Wilk |
| 5,464,395 A | | 11/1995 | Faxon et al. |
| 5,470,308 A | | 11/1995 | Edwards et al. |
| 5,485,840 A | | 1/1996 | Bauman |
| 5,499,630 A | | 3/1996 | Hiki et al. |
| 5,527,325 A | | 6/1996 | Conley et al. |
| 5,549,581 A | | 8/1996 | Lurie et al. |
| 5,558,101 A | | 9/1996 | Brooks et al. |
| 5,558,673 A | | 9/1996 | Edwards et al. |
| 5,570,693 A | | 11/1996 | Jang et al. |
| 5,571,093 A | | 11/1996 | Cruz et al. |
| 5,584,803 A | | 12/1996 | Stevens et al. |
| 5,588,960 A | | 12/1996 | Edwards et al. |
| 5,590,659 A | | 1/1997 | Hamilton et al. |
| 5,596,990 A | | 1/1997 | Yock et al. |
| 5,597,378 A | | 1/1997 | Jervis |
| 5,636,644 A | | 6/1997 | Hart et al. |
| 5,643,231 A | | 7/1997 | Lurie et al. |
| 5,658,262 A | | 8/1997 | Castaneda et al. |
| 5,662,124 A | | 9/1997 | Wilk |
| 5,662,671 A | * | 9/1997 | Barbut et al. ................. 606/170 |
| 5,672,153 A | | 9/1997 | Lax et al. |
| 5,681,336 A | * | 10/1997 | Clement et al. ............... 606/159 |
| 5,699,805 A | | 12/1997 | Seward et al. |
| 5,701,905 A | | 12/1997 | Esch |
| 5,722,963 A | | 3/1998 | Lurie et al. |
| 5,724,977 A | * | 3/1998 | Yock et al. .................... 600/437 |
| 5,733,248 A | | 3/1998 | Adams et al. |
| 5,735,847 A | | 4/1998 | Gough et al. |
| 5,758,663 A | | 6/1998 | Wilk et al. |
| 5,762,636 A | | 6/1998 | Rupp et al. |
| 5,769,830 A | | 6/1998 | Parker |
| 5,771,895 A | | 6/1998 | Slager |
| 5,775,327 A | | 7/1998 | Randolph et al. |
| 5,814,064 A | | 9/1998 | Daniel et al. |
| 5,827,315 A | | 10/1998 | Yoon |
| 5,830,224 A | | 11/1998 | Cohn et al. |
| 6,190,353 B1 | * | 2/2001 | Makower et al. ........... 604/95.01 |
| 6,231,546 B1 | * | 5/2001 | Milo et al. ................ 604/164.13 |
| 6,283,951 B1 | * | 9/2001 | Flaherty et al. ................. 604/529 |
| 6,302,875 B1 | * | 10/2001 | Makower et al. ............. 604/528 |
| 6,375,615 B1 | * | 4/2002 | Flaherty et al. ................. 600/439 |
| 6,544,230 B1 | * | 4/2003 | Flaherty et al. .......... 604/164.12 |
| 2008/0051756 A1 | * | 2/2008 | Makower et al. ............. 604/508 |

* cited by examiner

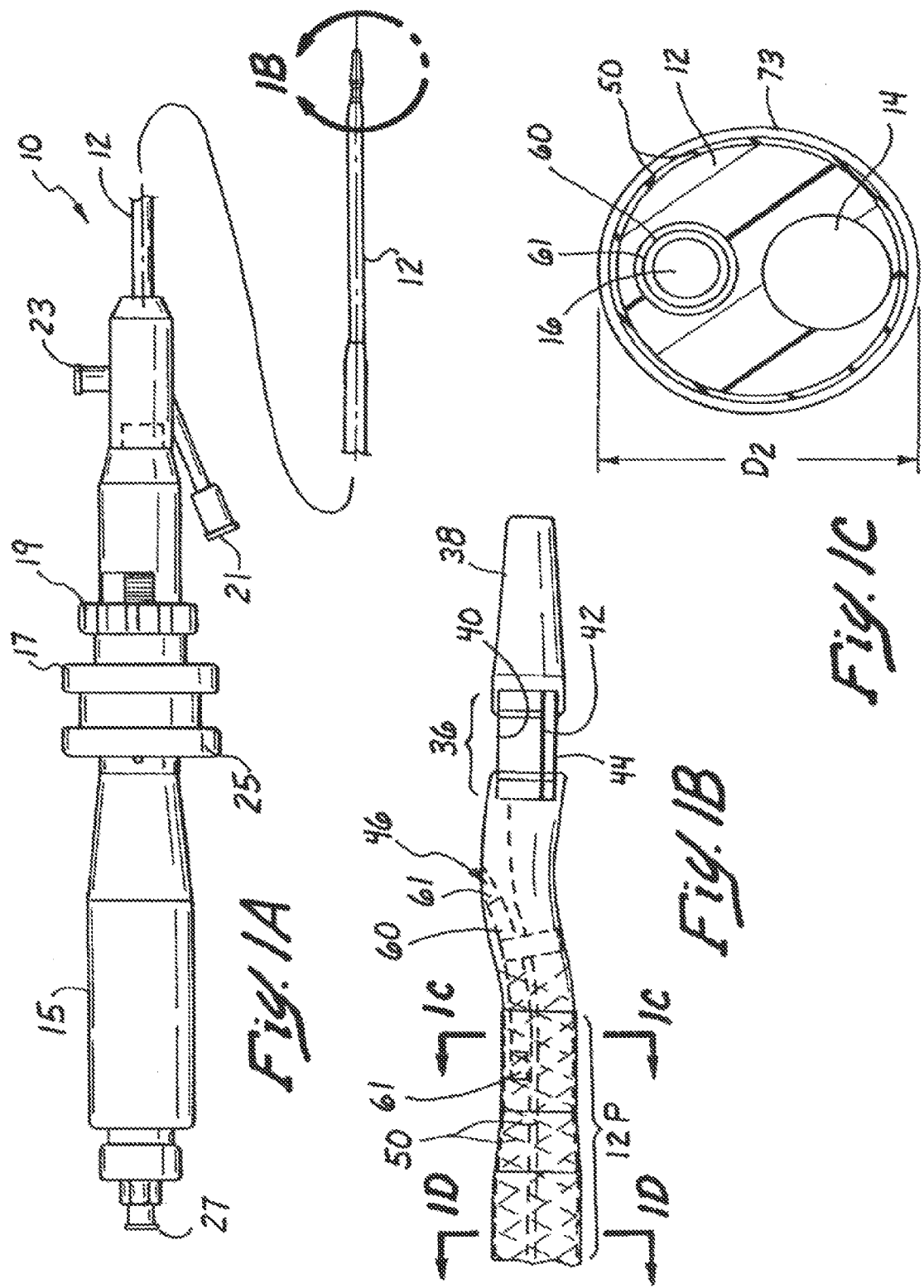

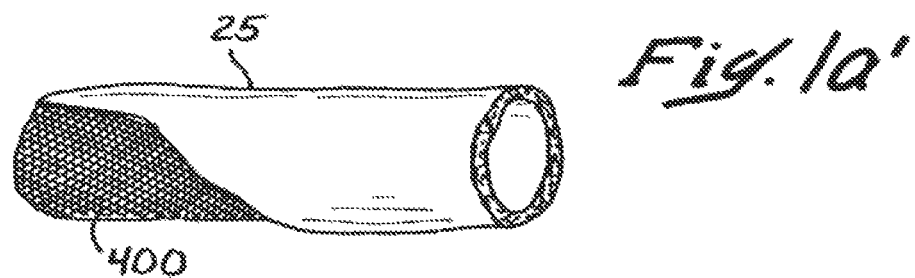
Fig. 1a'
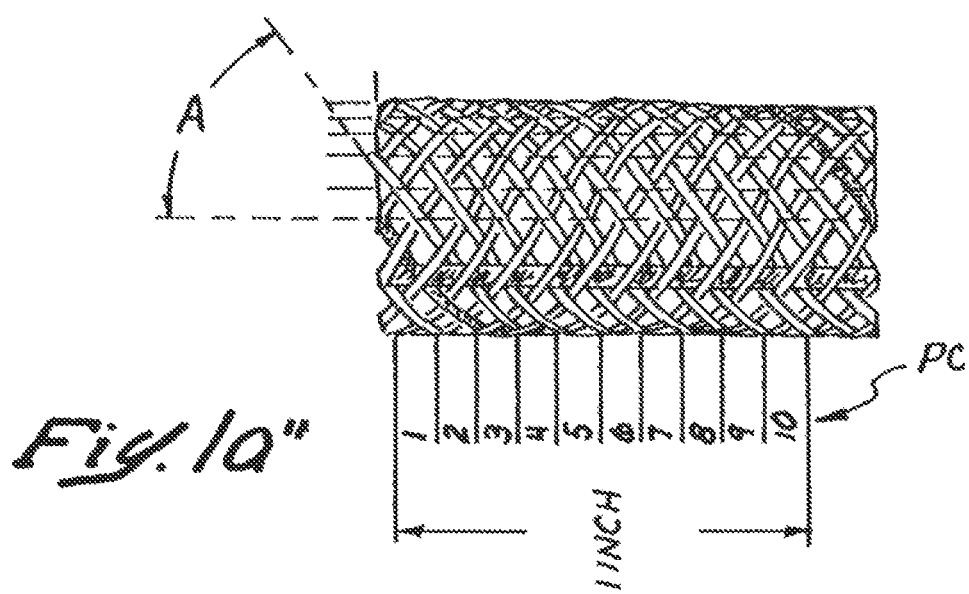
Fig. 1a"
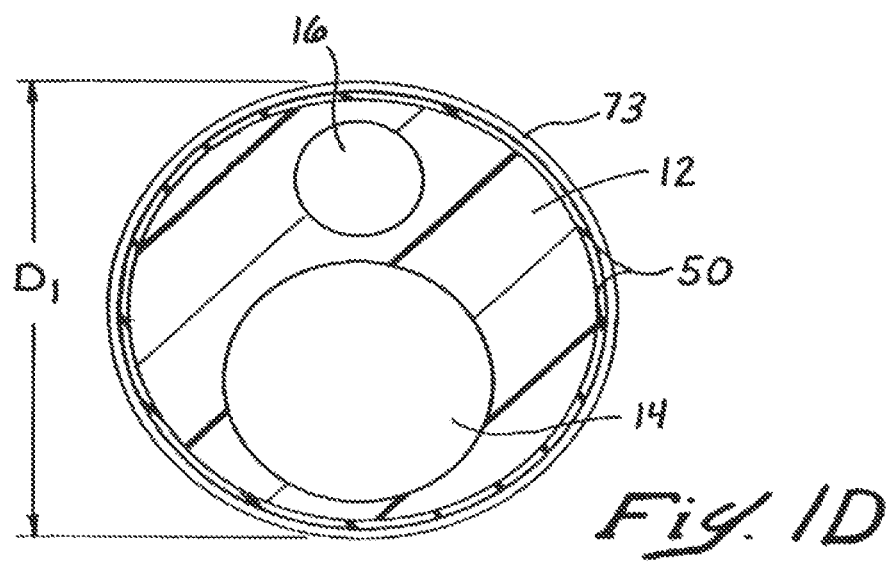
Fig. 1D

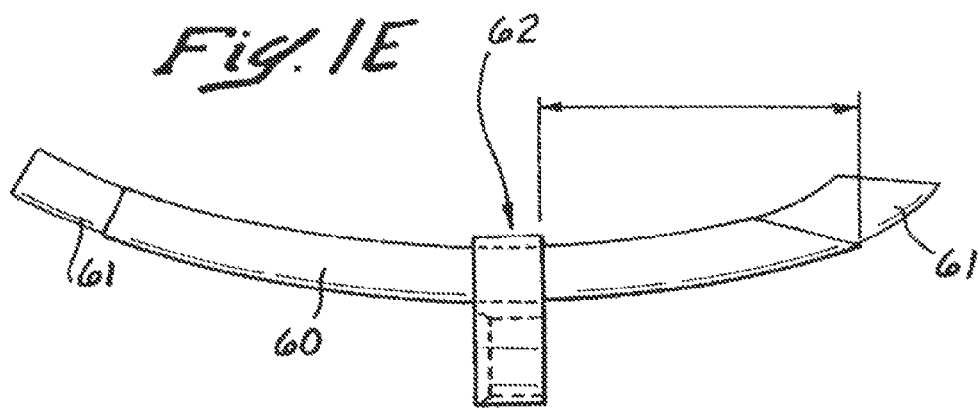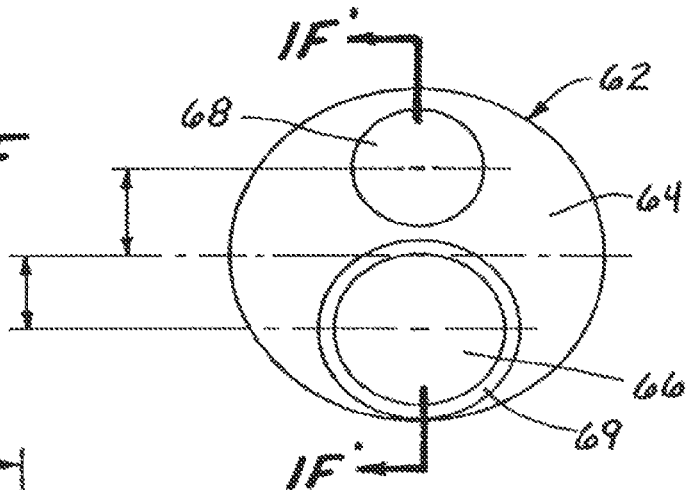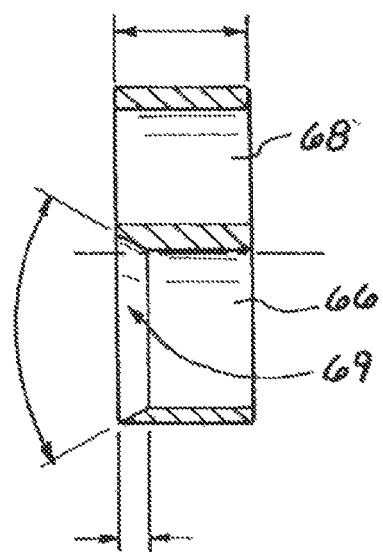

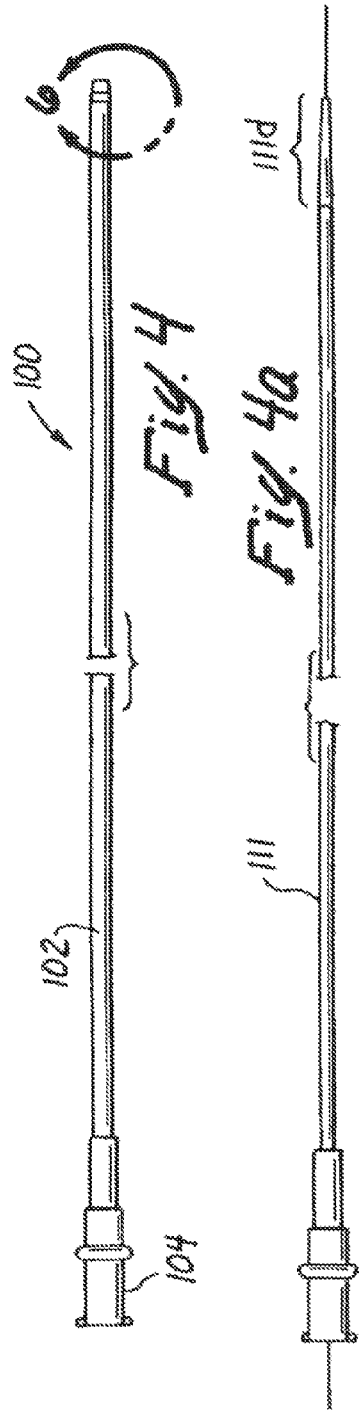
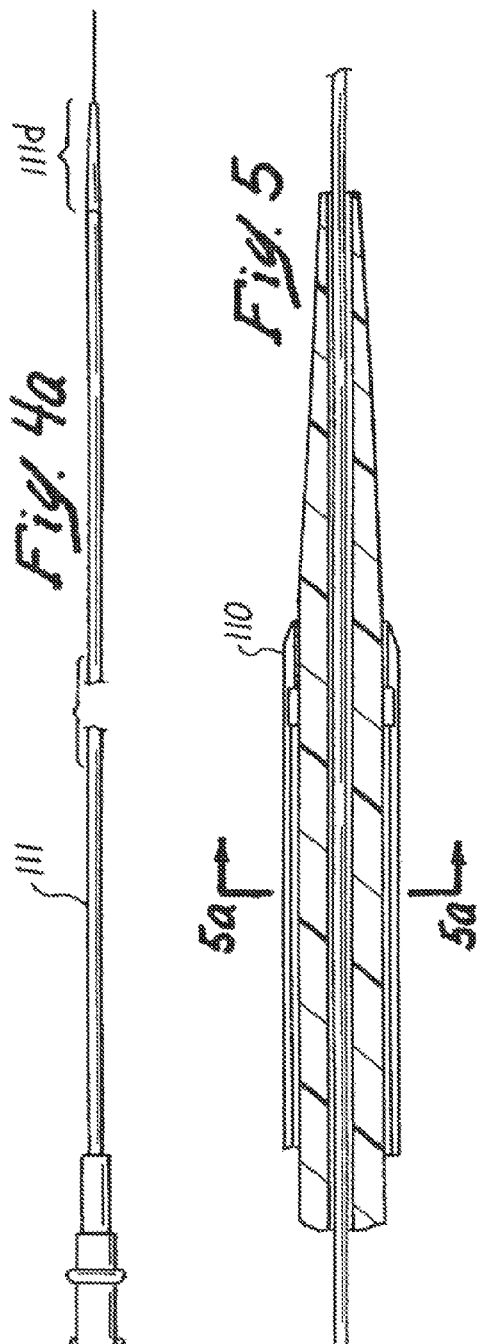
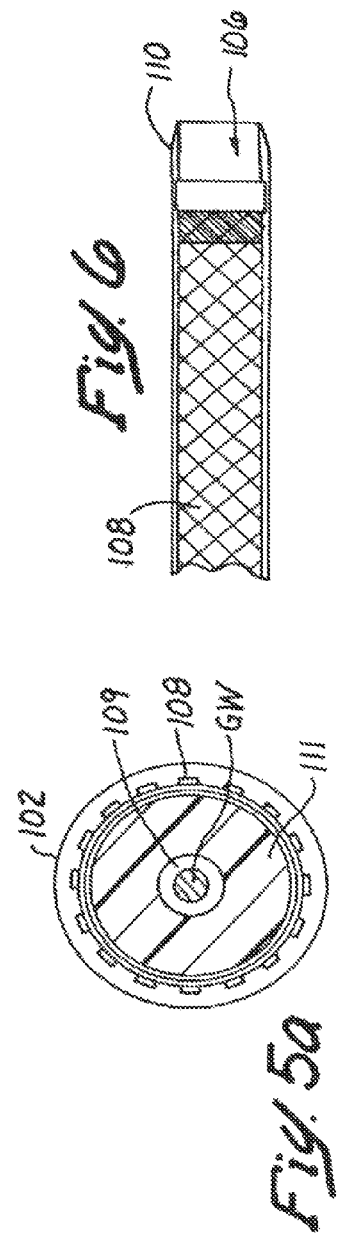

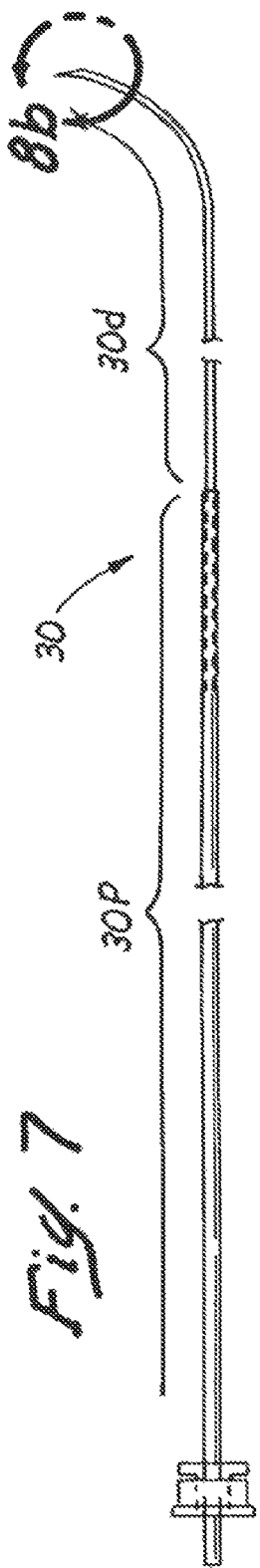
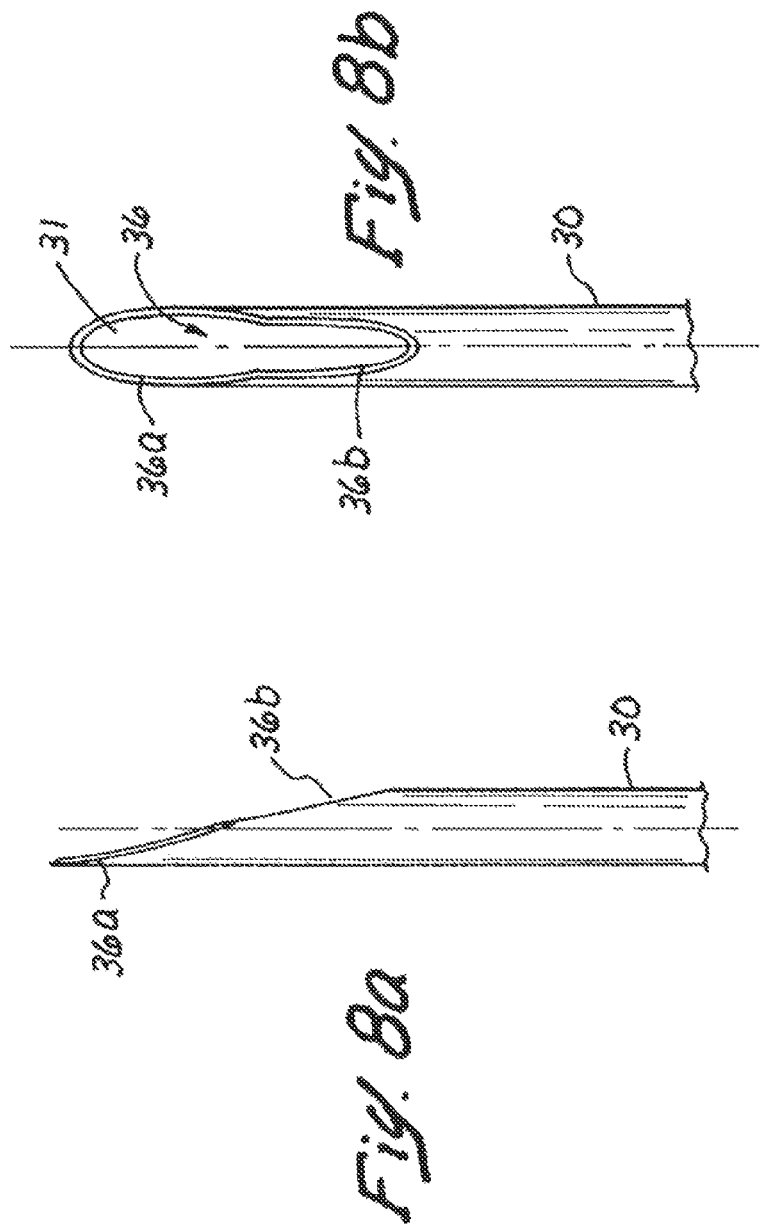
Fig. 7
Fig. 8a
Fig. 8b

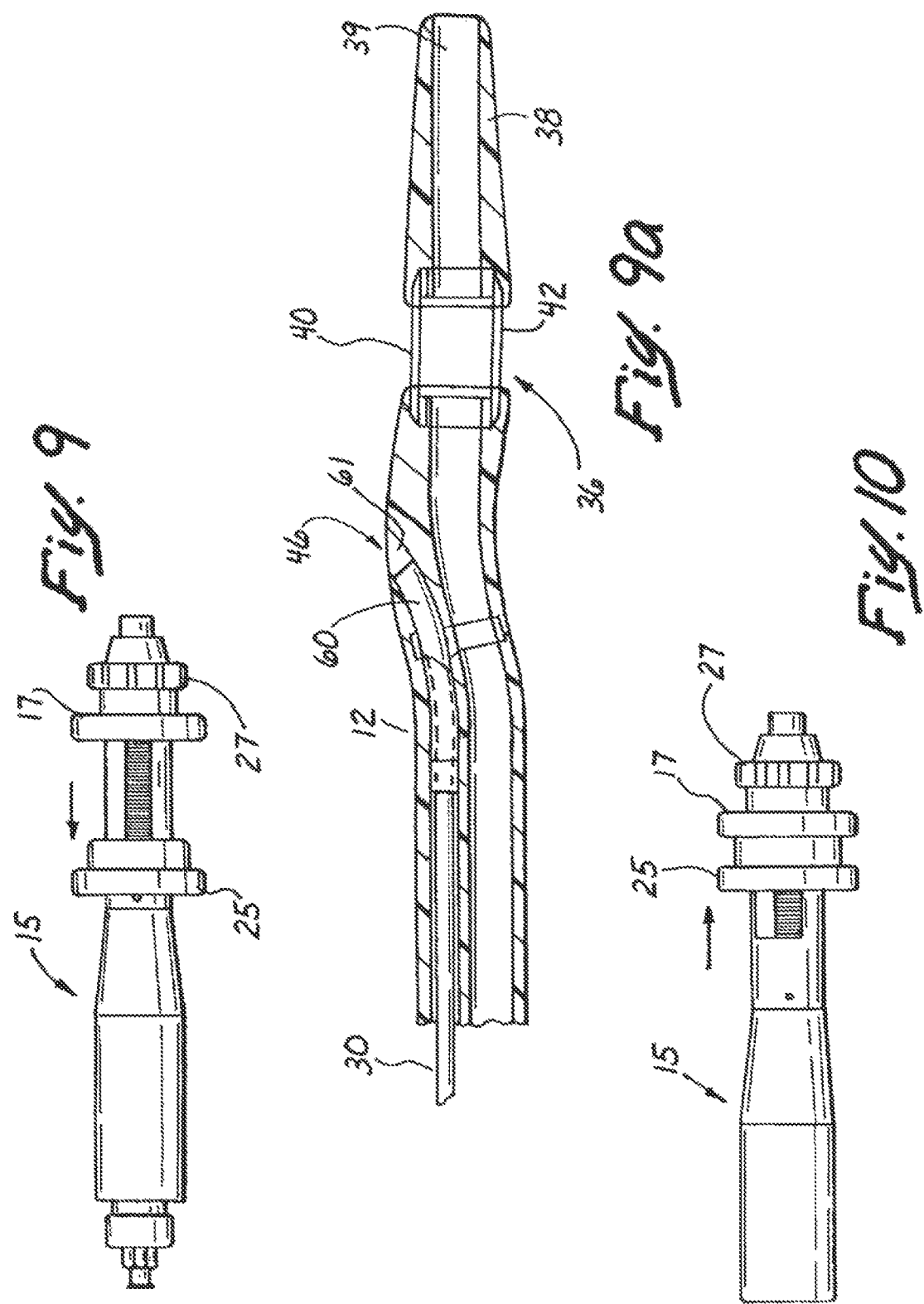

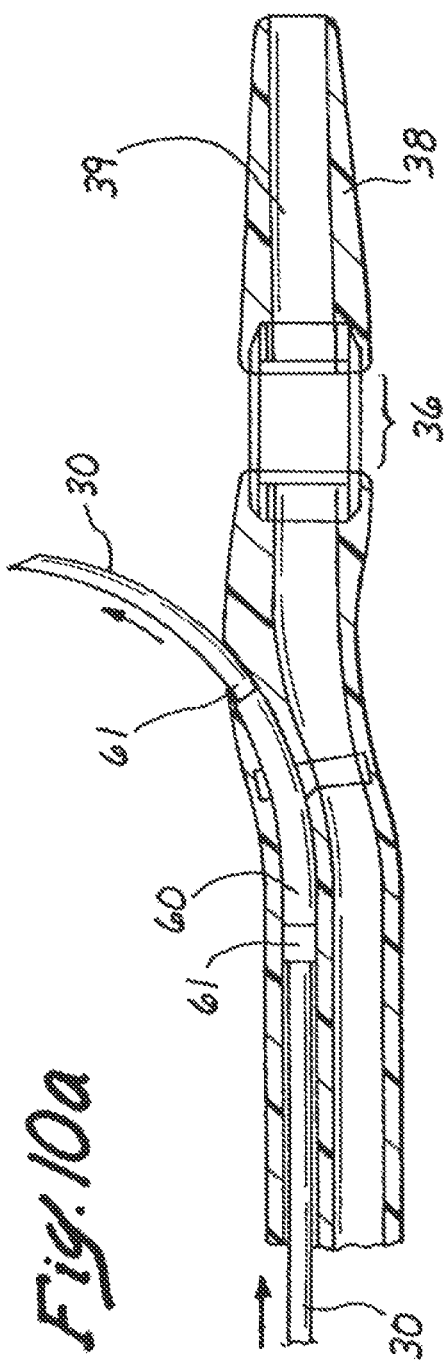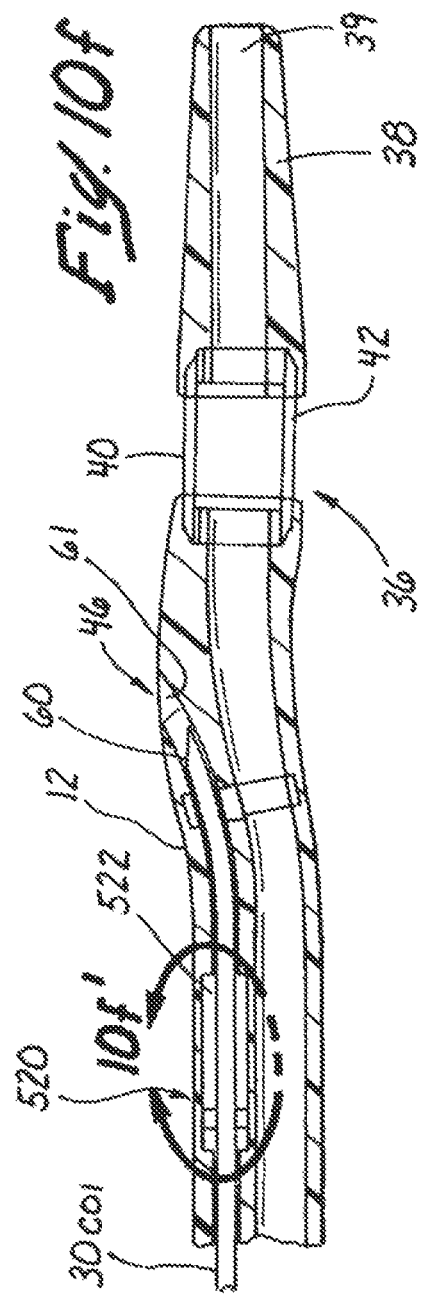

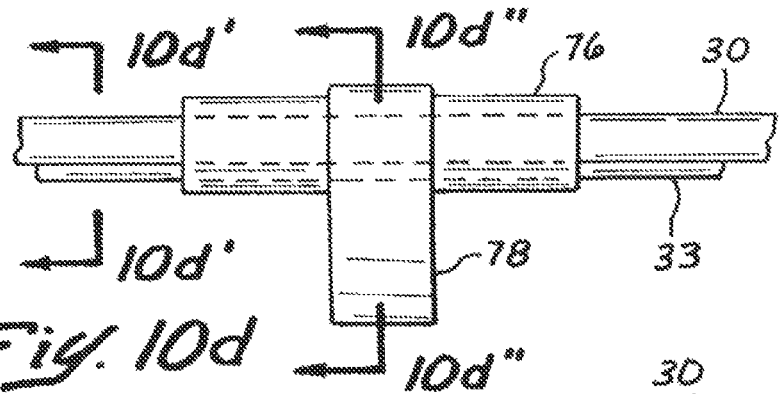
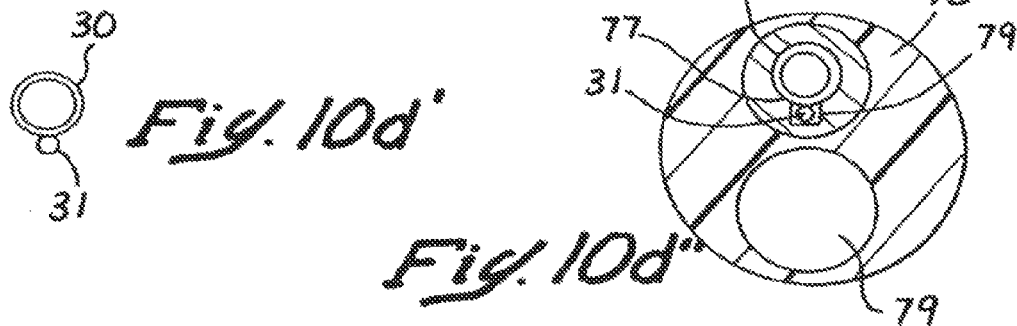
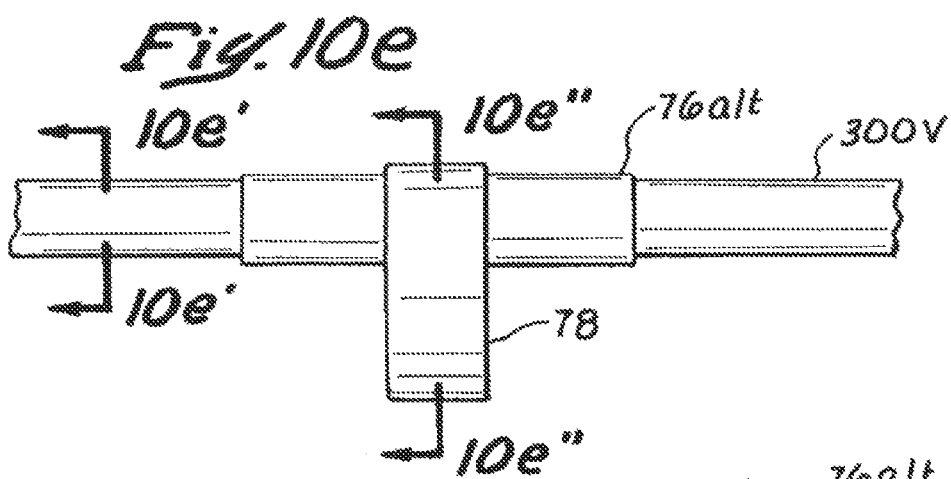
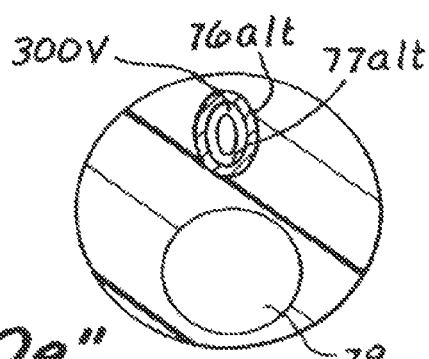

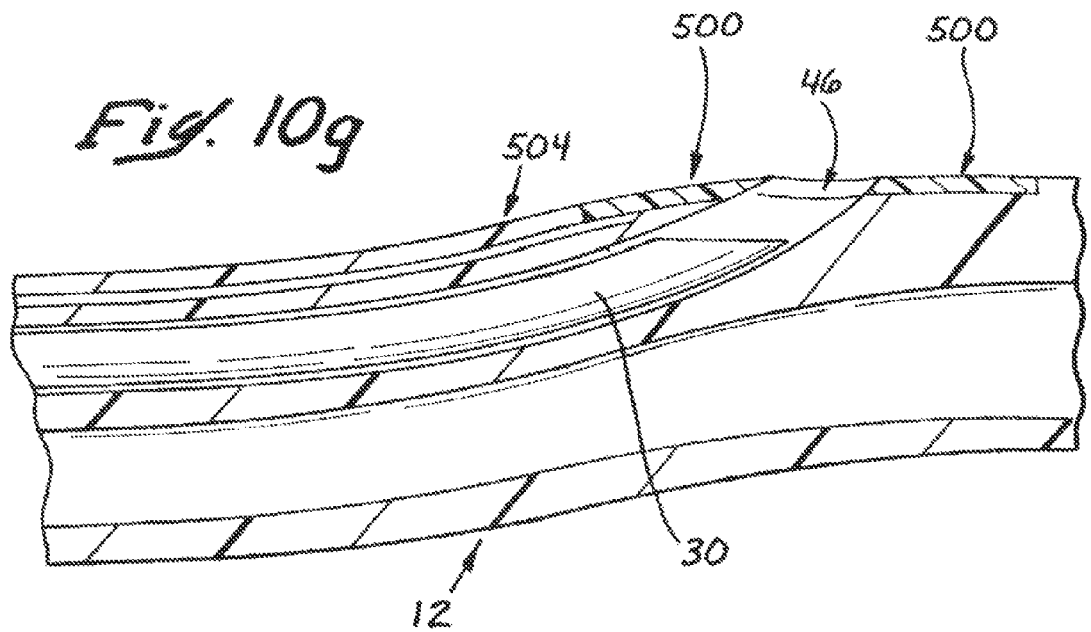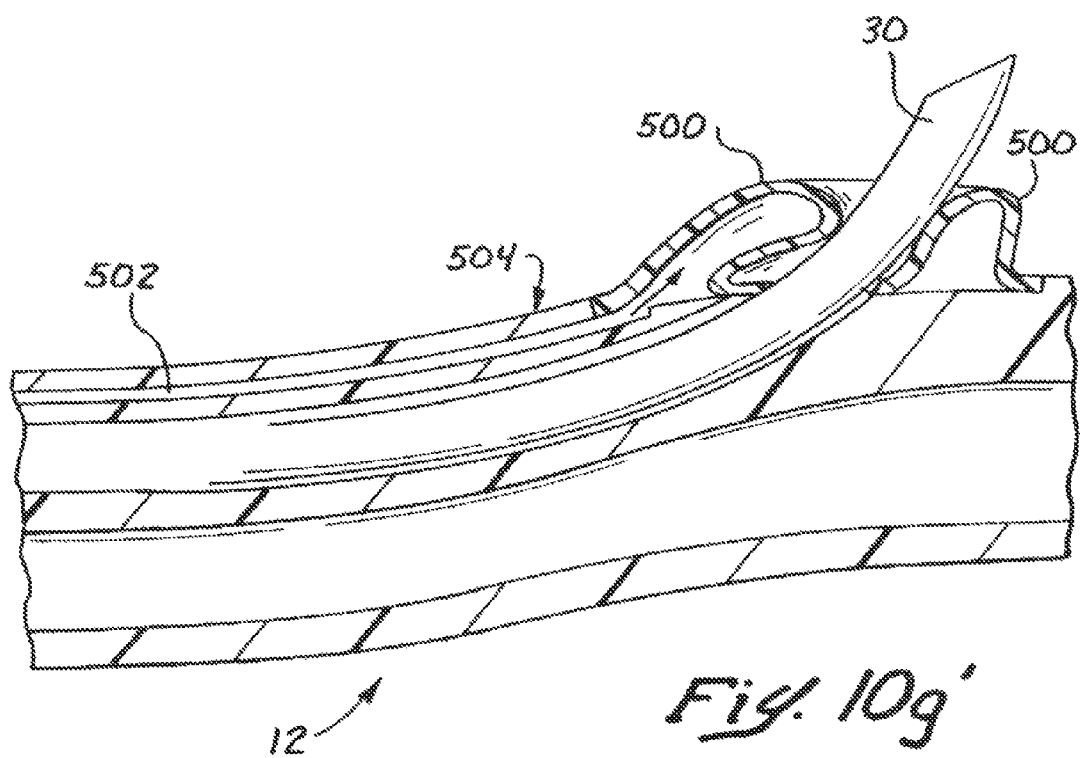

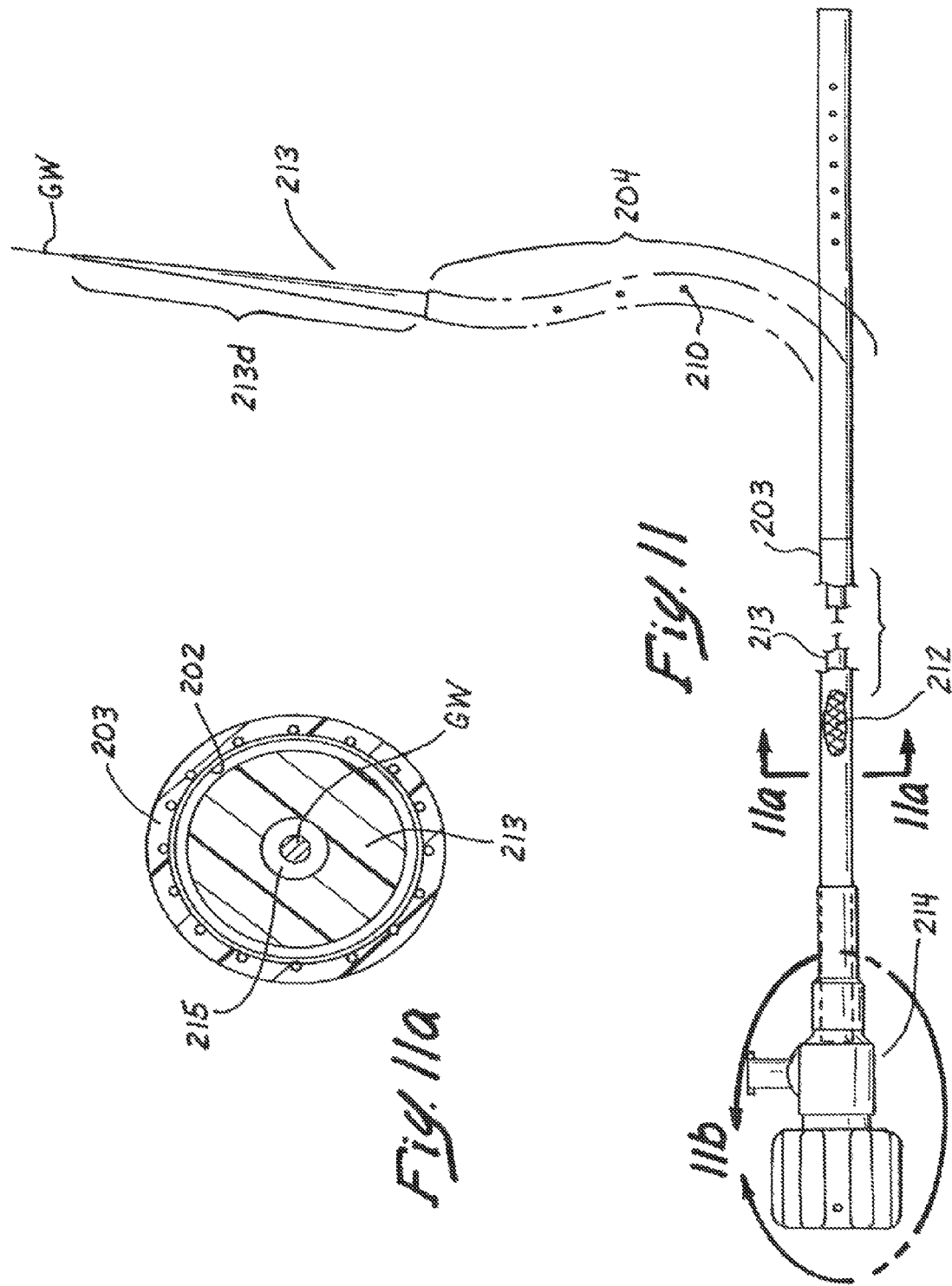

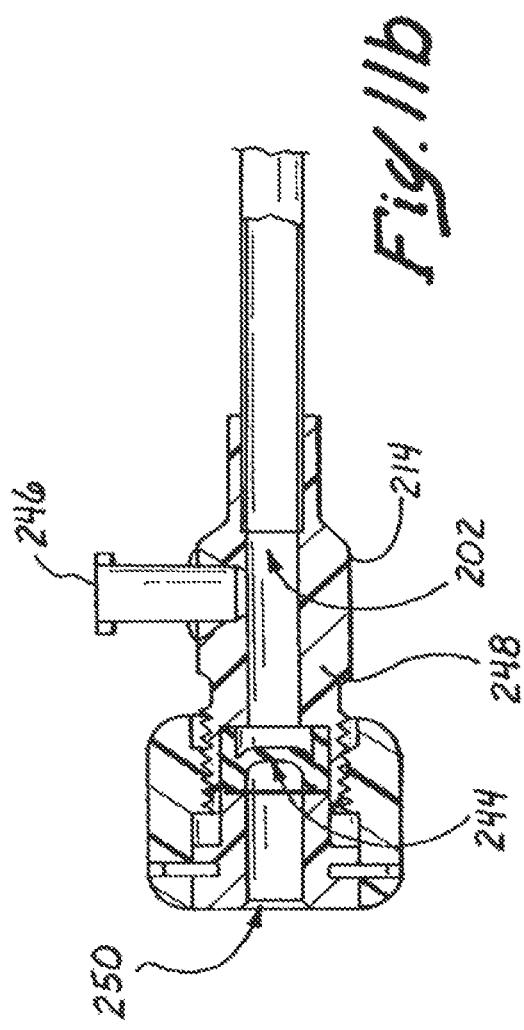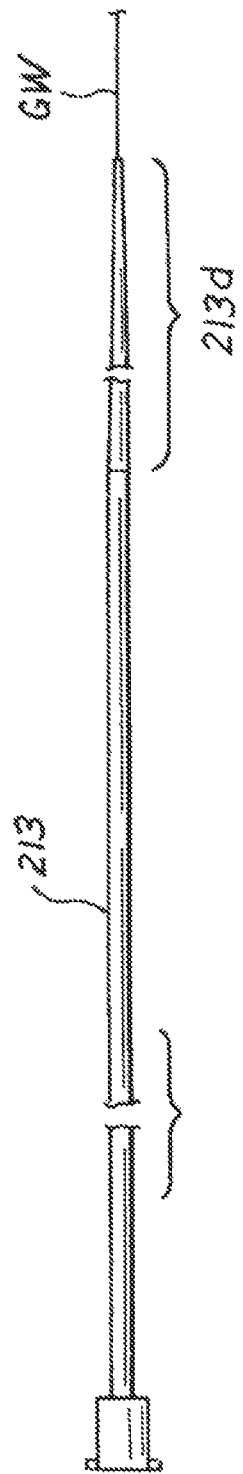

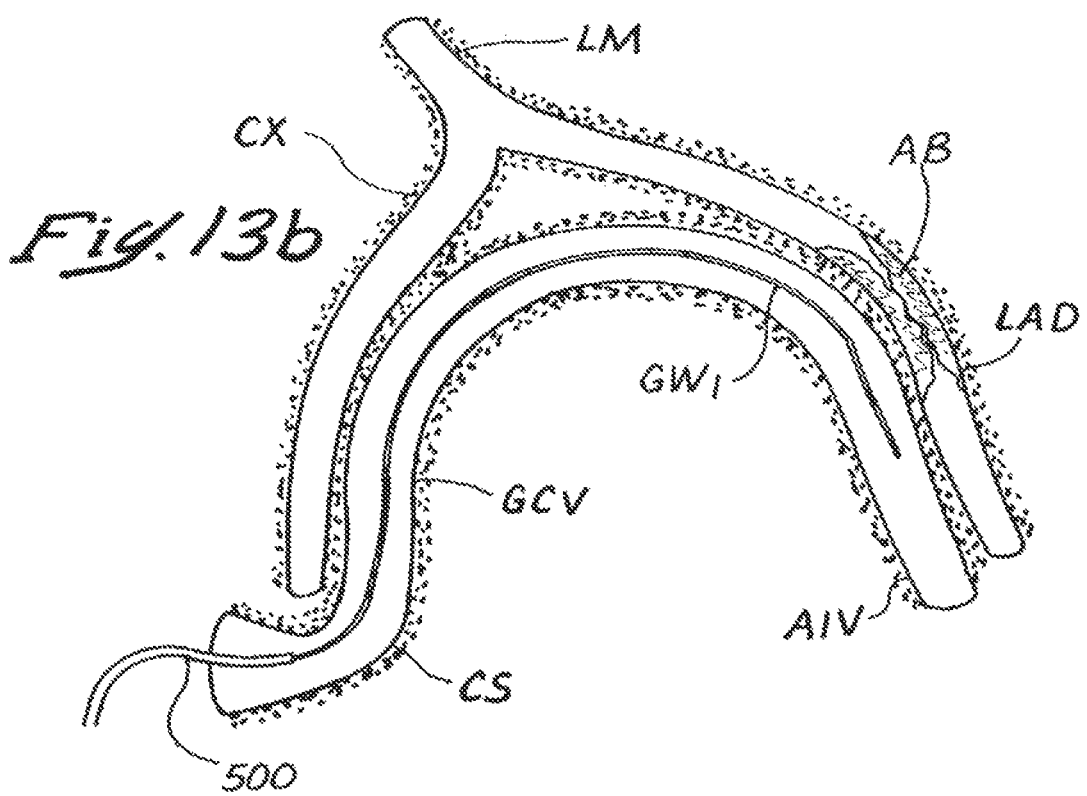
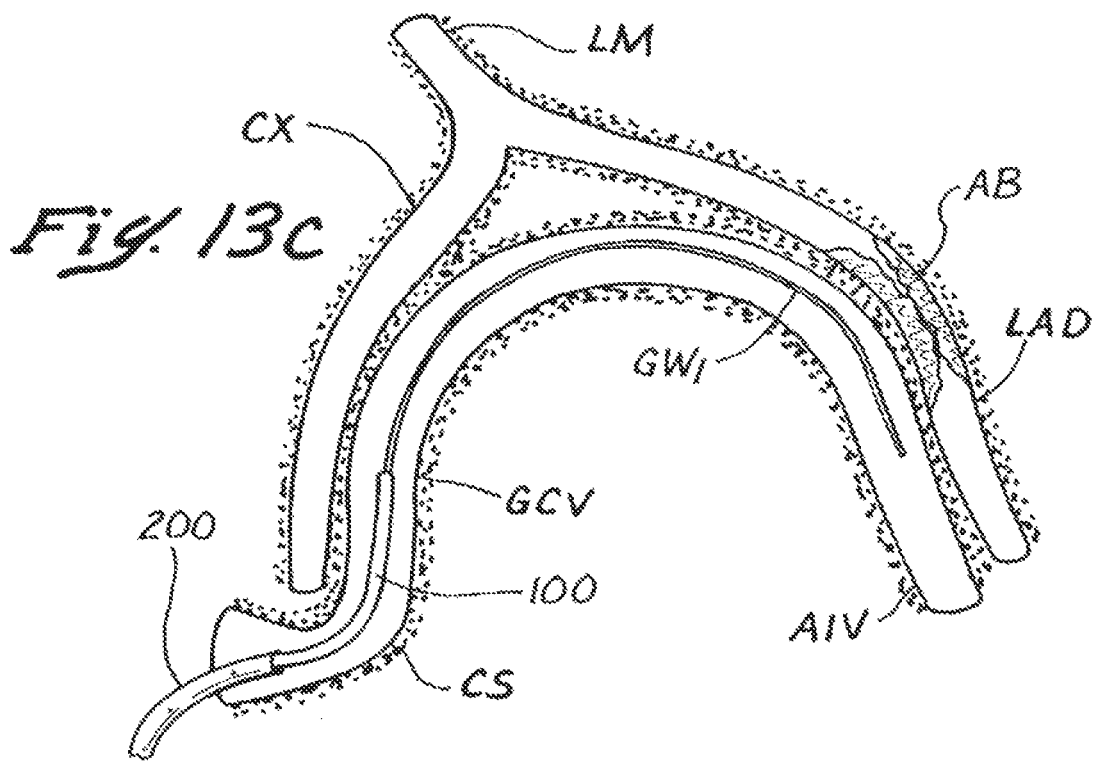

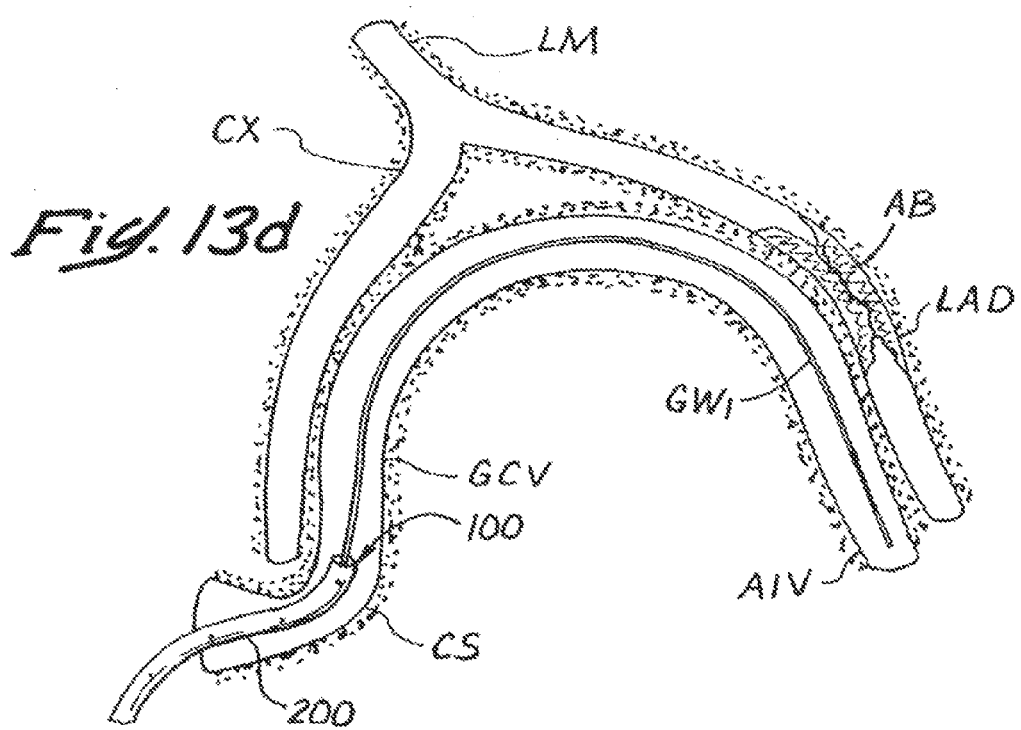
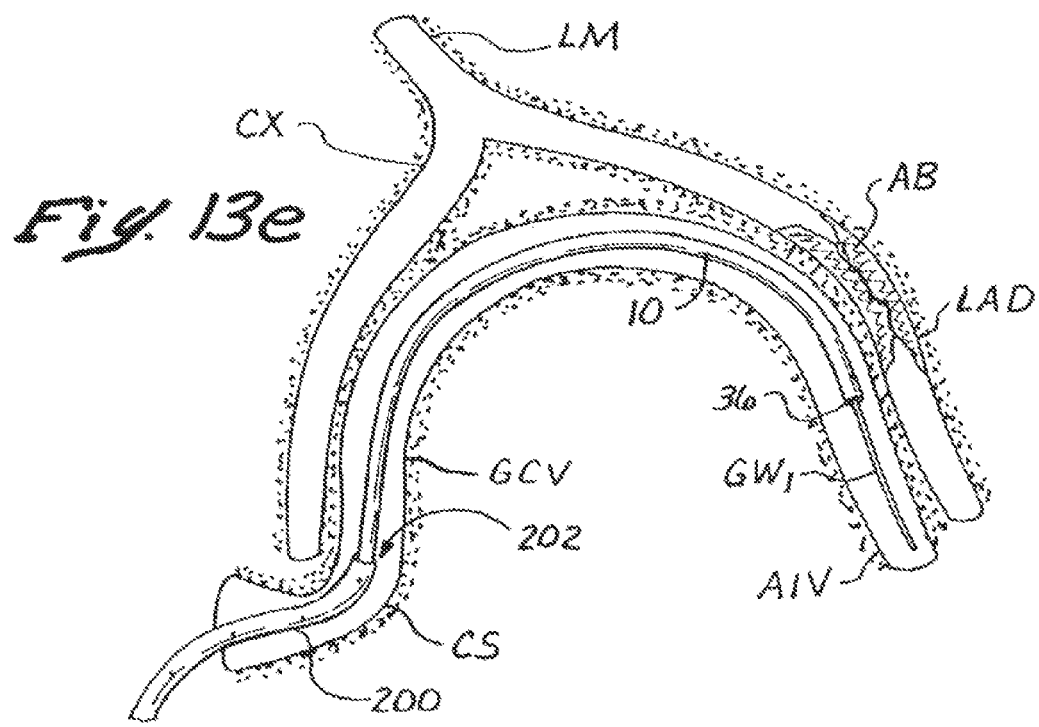

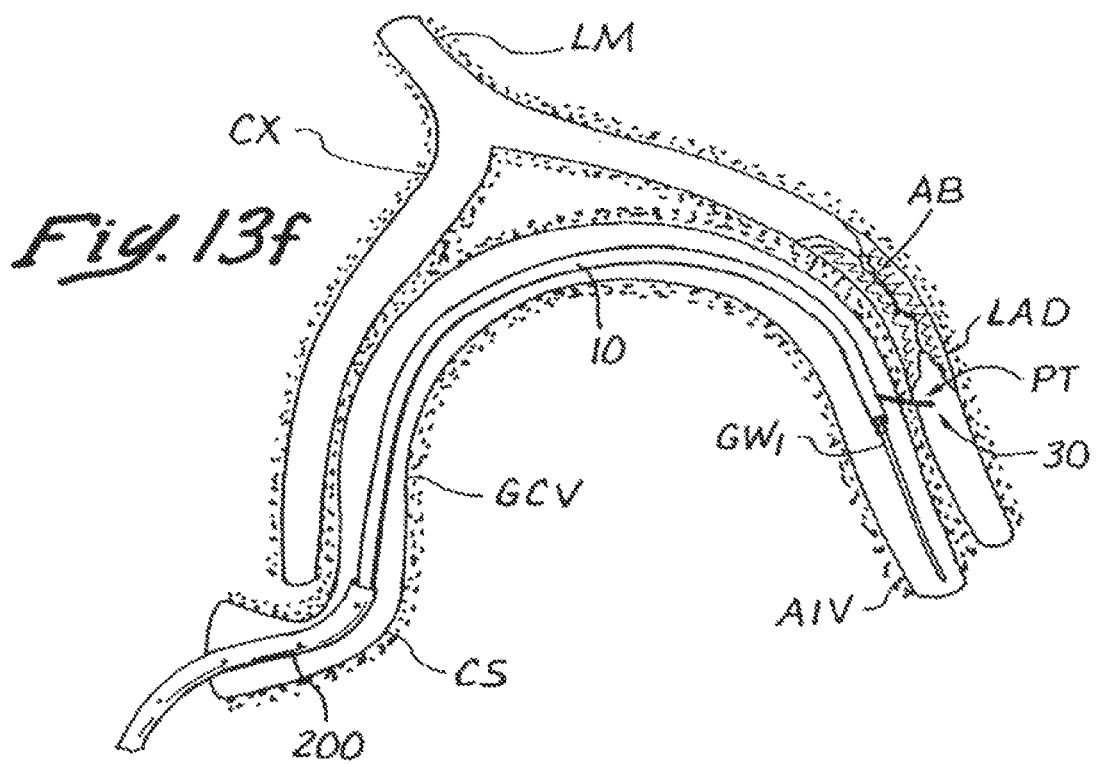
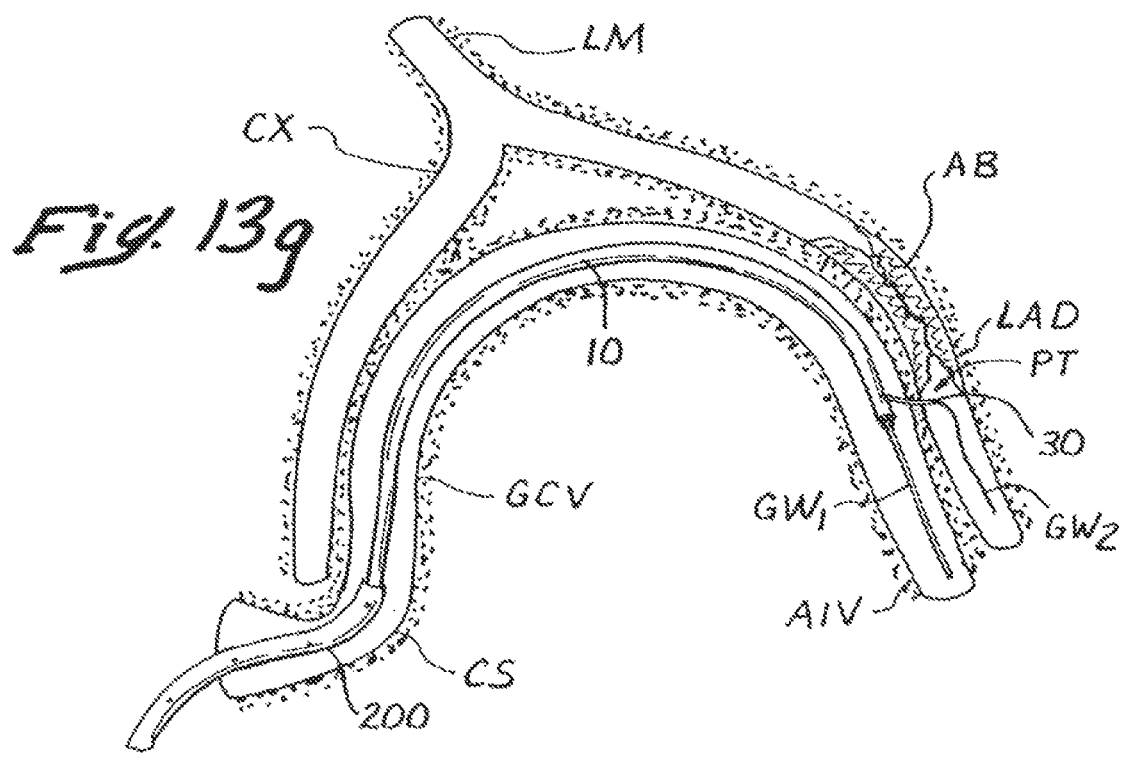

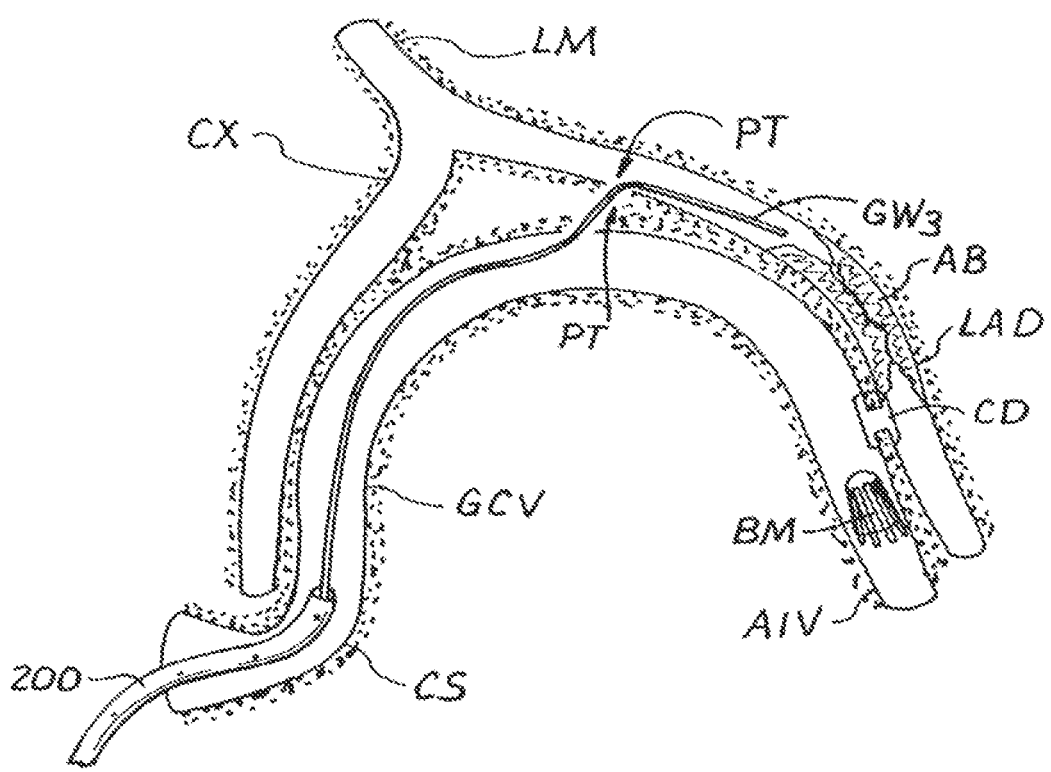

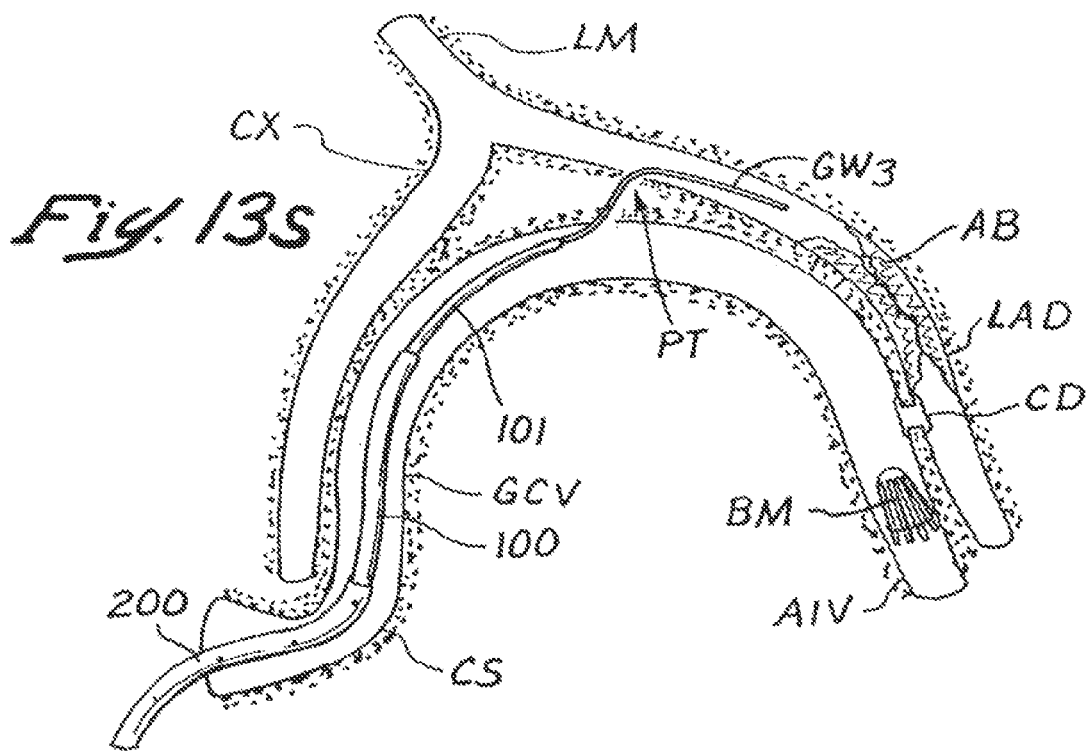
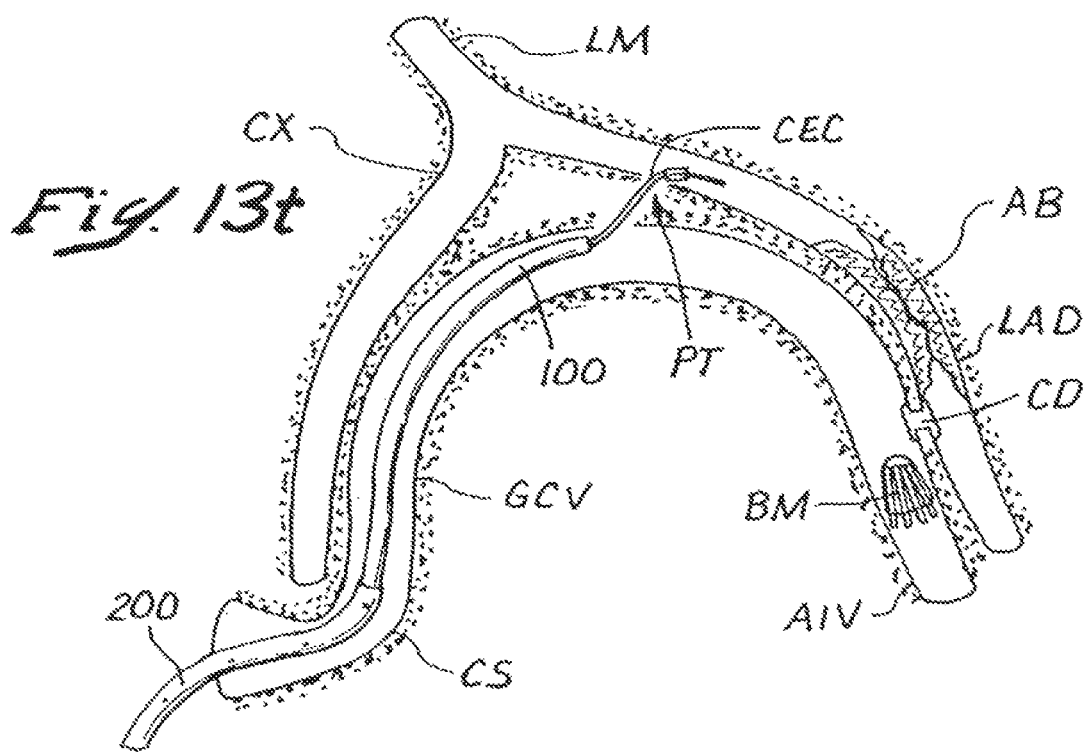

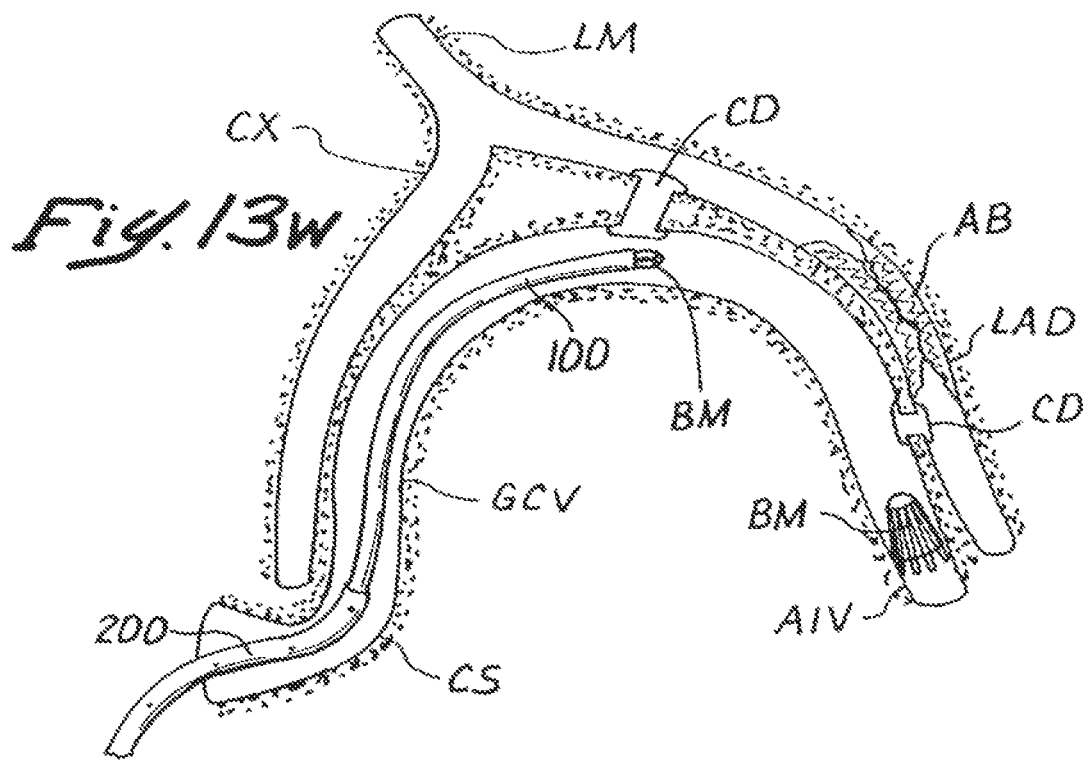
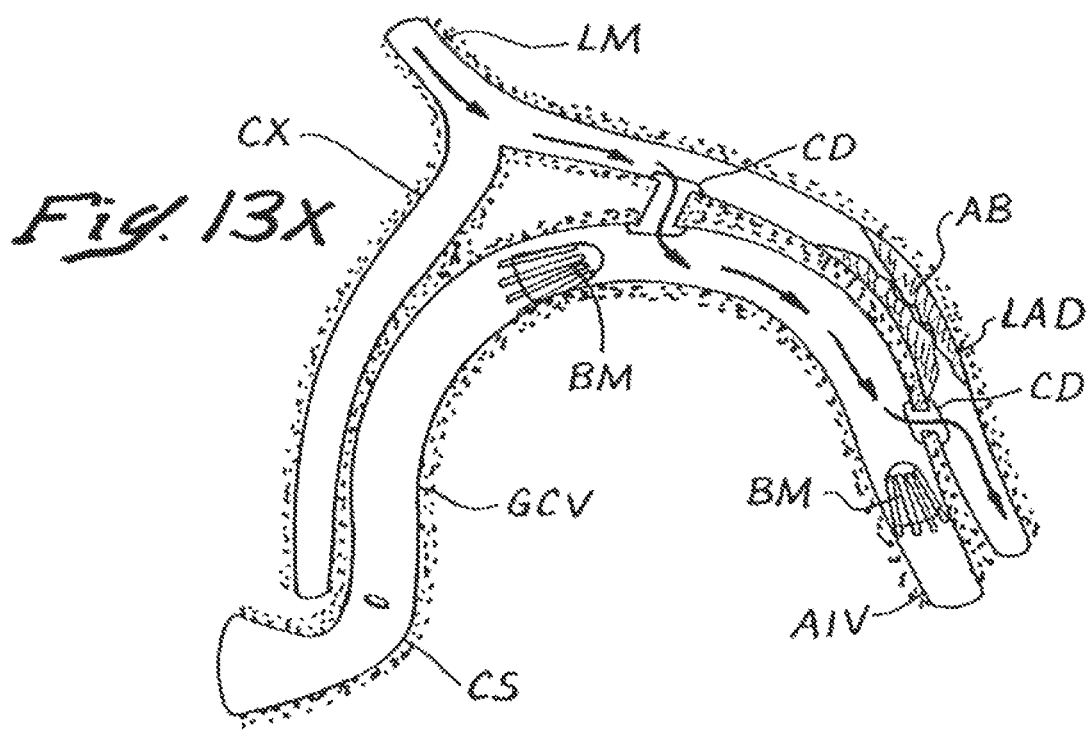

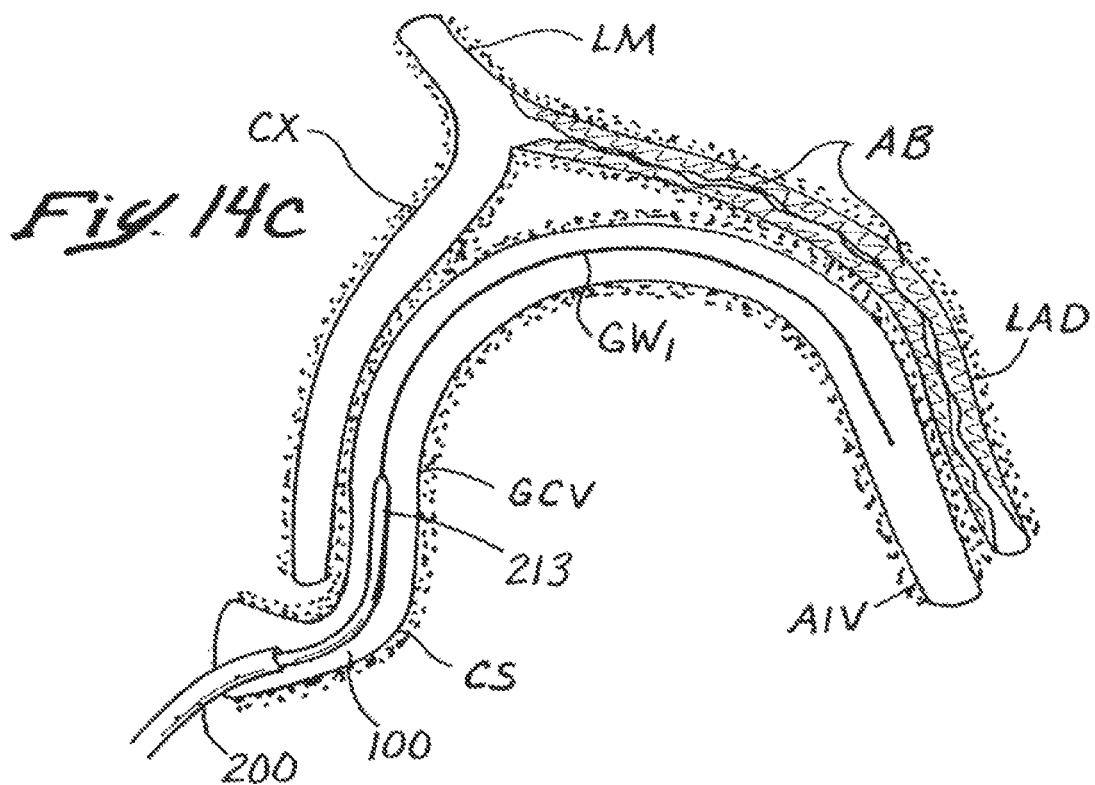
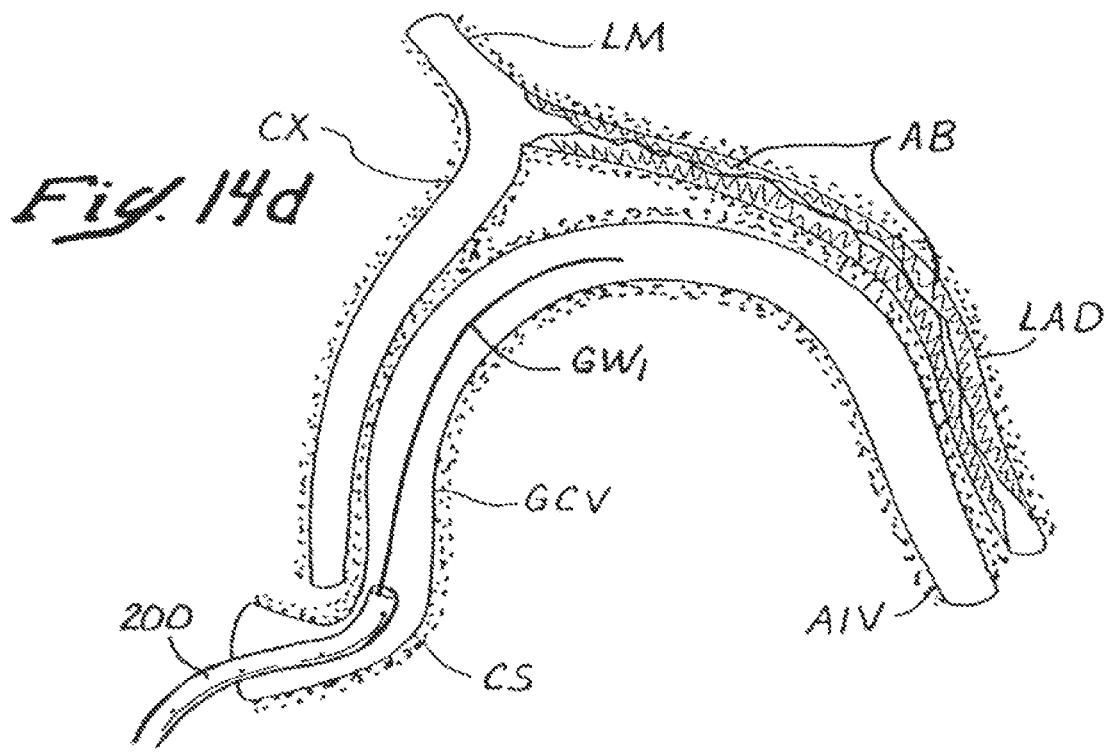

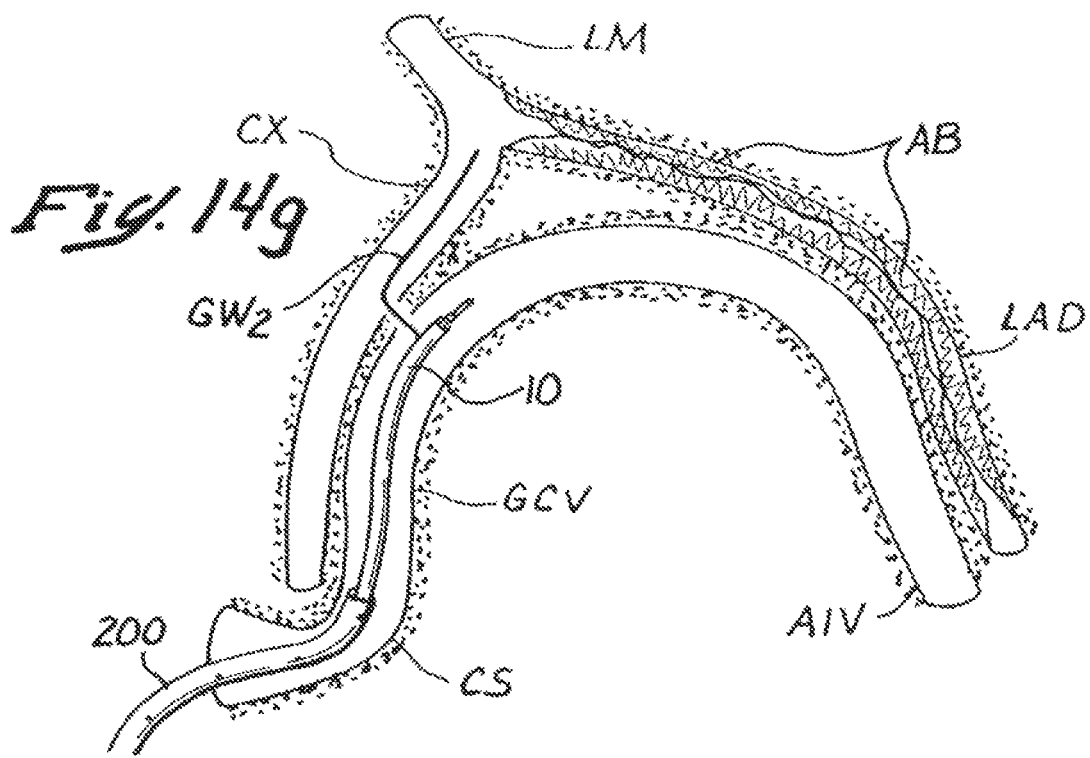
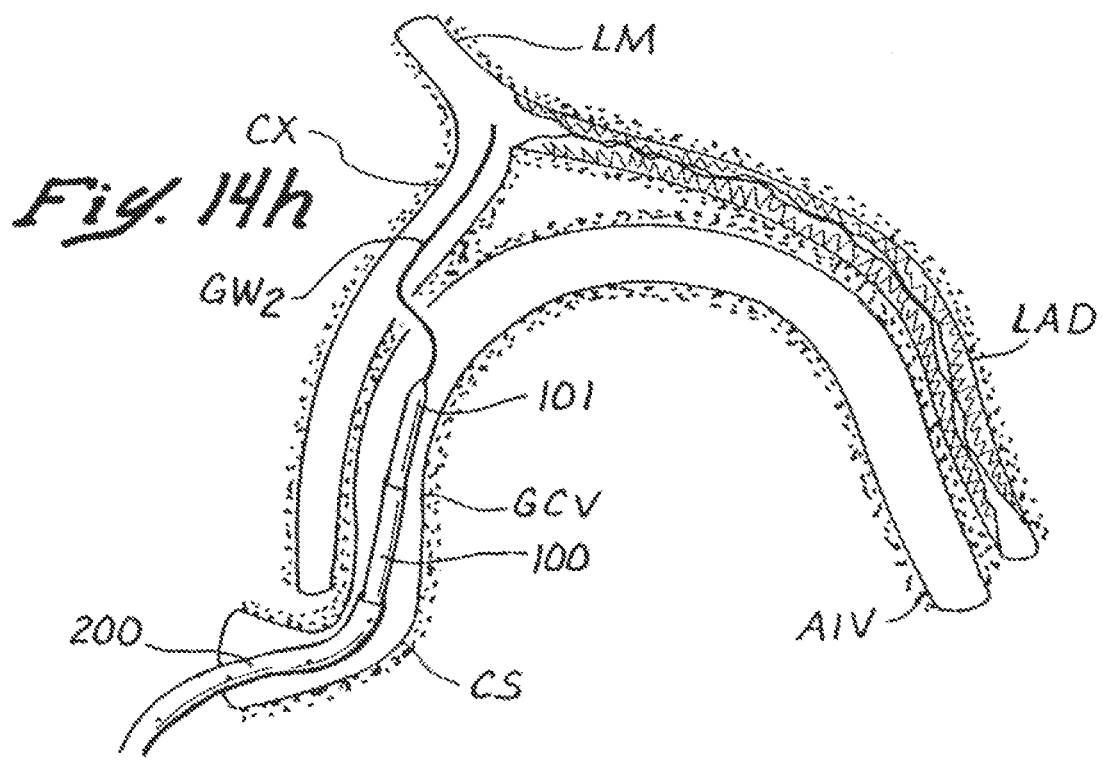

CATHETERS, SYSTEMS AND METHODS FOR PERCUTANEOUS IN SITU ARTERIO-VENOUS BYPASS

RELATED APPLICATIONS

This application is a Continuation of U.S. patent application Ser. No. 10/370,429 filed Feb. 20, 2003, now U.S. Pat. No. 8,585,596; which is a Division of U.S. patent application Ser. No. 09/282,276 filed Mar. 31, 1999, now U.S. Pat. No. 6,544,230; which claims the benefit and priority to U.S. Provisional Patent Application Ser. No. 60/080,196 entitled Methods and Apparatus for Percutaneous In Situ Artery Bypass, filed Mar. 31, 1998.

FIELD OF THE INVENTION

The present invention relates generally to medical devices and methods, and more particularly to catheter devices and methods that are useable to form channels (e.g., penetration tracts) between vessels such as arteries and veins as well as between vessels and other anatomical structures, in furtherance of a therapeutic purpose such as bypassing an arterial blockage, delivering therapuetic agents, or performing other interventional procedures.

BACKGROUND OF THE INVENTION

Applicant has invented several new interventional procedures wherein channels (e.g., bloodflow passageway(s)) are formed between blood vessels, and between blood vessels and other target structures, using transluminally advanceable catheters. These new procedures include novel percutaneous, transluminal techniques for bypassing obstructions in coronary or peripheral arteries through the use of the adjacent vein(s) as in situ bypass conduit(s), and other means of revascularizing oxygen starved tissues or delivering therapuetic substances to vessels, tissue and other organs. These procedures are fully described in U.S. Pat. No. 5,830,222 and in U.S. patent application Ser. Nos. 08/730,496, 09/048,147 and 09/048,147. Some of these procedures may be performed by a venous approach, such as vein-to-artery wherein a tissue penetrating catheter is inserted into a vein and the desired arterio-venous passageway is initially formed by passing a tissue penetrating element (e.g., a flow of energy or an elongate penetration member) from a catheter, through the wall of the vein in which the catheter is positioned, and into the lumen of an adjacent artery. Alternatively, some of these procedures may be performed by an artery-to-vein approach wherein the catheter is inserted into an artery and the desired arterio-venous passageway is initially formed by passing a tissue penetrating element (e.g., a flow of energy or elongate penetration member) from the catheter, through the wall of the artery in which the catheter is positioned, and into the lumen of an adjacent vein. Both approaches have been previously described in U.S. patent application Ser. No. 08/730,327. In addition, it may be advantageous to direct a penetrating element directly into other anatomical structures such as the myocardium, pericardium, chamber of the heart or other organs as described in U.S. patent application Ser. No. 09/048,147.

Different considerations and limitations may apply, depending upon which of these approaches (the "vein-to-artery approach, the "artery-to-vein" approach, or vessel to other anatomical structure) is being used or, more generally, the size and contour of the blood vessel lumen in which the operative catheters are to be placed, and the distance and/or angle between the vessels or other target. This is due in part to the fact that, in the heart as well as in other areas of the body, adjacent arteries and veins may be of significantly different diameter and significantly different dilatory capability. In addition, depending on the procedure to be performed, for example, such as the desired angle of channel creation between blood vessels, one approach may be preferred over the other, to promote, among other things, blood flow channels that encourage non-turbulent blood flow. Also, the consequences associated with causing temporary complete obstruction of a vein may be significantly less than the consequences of causing temporary complete obstruction of an artery. Thus, it is desirable to devise tissue penetrating catheters of the above-described type that are sized, configured and/or equipped differently for use in blood vessels of different sizes, shapes and in connection with different types of pathology.

Moreover, it is desirable for tissue penetrating catheters of the above-described type to be constructed and equipped for precise aiming and control of the tissue penetrating element as the tissue penetrating element passes from the catheter, through at least the wall of the blood vessel in which the catheter is located, and to the target location. Such aiming and control of the tissue penetrating element ensures that it will create the desired penetration tract at the intended location with minimal or no damage to surrounding tissues or other structures.

SUMMARY OF THE INVENTION

The present invention provides methods and apparatus for performing the percutaneous in situ coronary arterio-venous bypass procedures generally described in U.S. Pat. No. 5,830,222 and U.S. patent application Ser. No. 08/730,327, and other procedures requiring the use of accurately placed catheter elements.

A. Devices and System:

In accordance with the invention, there is provided a system for forming an initial penetration tract from the lumen of a blood vessel in which the catheter is positioned to a target location (such as another blood vessel, organ or myocardial tissue). This system generally comprises:

a) a coronary sinus guide catheter which is insertable within the venous system of the body and into the coronary sinus of the heart;

b) a tissue penetrating catheter which is advanceable to a position within a coronary vein, such tissue-penetrating catheter comprising i) a flexible catheter body, ii) a tissue penetrating element (e.g., a needle member, electrode or flow of energy) which is passable from the catheter body, through the wall of the coronary vein in which the catheter body is positioned and into the lumen of an adjacent coronary artery, or other targeted structure, iii) an imaging lumen through which an imaging catheter (e.g., an intravascular ultrasound imaging (IVUS) catheter) may be passed; and, c) a separate imaging catheter (e.g., an intravascular ultrasound (IVUS) catheter) that is advanceable through the imaging lumen of the tissue-penetrating catheter.

In addition to components a-c above, this catheter system may include a subselective sheath and introducer. The subselective sheath comprises a flexible tubular sheath that has a proximal end, a distal end and a lumen extending therethrough. The introducer is insertable through the lumen of the sheath and has a tapered, non-traumatizing distal portion that protrudes out of and beyond the distal end of the sheath as well as a guidewire lumen extending longitudinally therethrough. The tapered, non-traumatic distal portion of the introducer serves to dilate the blood vessel lumens or openings through which the sheath is inserted, thereby facilitating advancement and positioning of the sheath at a desired location within the body. After the sheath has been advanced to its desired position within the body, the introducer is extracted and various channel modifying catheters, connector delivery catheters and/or blocker delivery catheters may be advanced through the subselective sheath.

The coronary sinus guide catheter may incorporate a hemostatic valve to prevent backflow or leakage of blood from the proximal end thereof. Also, the coronary sinus guide catheter may include an introducer that is initially insertable through the guide catheter lumen. This introducer has a tapered, non-traumatizing distal portion that protrudes out of and beyond the distal end of the guide catheter, and a guidewire lumen extending longitudinally therethrough. The tapered, non-traumatizing distal portion of the introducer served to dilate the blood vessel lumens through which the guide catheter is inserted, thereby facilitating advancement and positioning of the coronary sinus guide catheter within the coronary venous sinus.

The tissue-penetrating catheter may incorporate one or more of the following elements to facilitate precise aiming and control of the tissue-penetration element and the formation of the passageway at the desired location:

a) Orientation Structure:

An orientation structure may be positioned or formed on the distal end of the tissue penetrating catheter. This orientation structure has i) a hollow cavity or space formed therewithin in alignment with the catheter's imaging lumen and ii) a marker member positioned in direct alignment with the opening in the catheter through which the tissue penetrating element emerges (or otherwise in some known spacial relationship to the path that will be followed by the tissue penetrating element as it passes from the tissue penetrating catheter). The separate imaging catheter may be advanced through the tissue penetrating catheter's imaging lumen and into the receiving space of the orientation structure. Thereafter, the imaging catheter is useable to image the target location as well as the marker. The image of the marker provides a path indication that is indicative of the path that will be followed by the tissue penetrating element as it passes from the tissue penetrating catheter. The operator may then adjust the rotational orientation of the tissue penetrating catheter as necessary to cause the path indication to be aligned with or aimed at the target location, thereby indicating that when the tissue penetrating member is subsequently passed from the catheter body, it will advance into the target location and not to some other location. In this manner the imaging lumen, separate imaging catheter and orientation structure that are incorporated into the catheter system of this invention operate, in combination with each other, to facilitate precise rotational orientation of the tissue penetrating catheter and aiming of the tissue penetrating element before the tissue penetrating element is advanced, thereby ensuring that the tissue penetrating element will enter the desired target at the desired location. In particular, the orientation structure may comprise a plurality (e.g., three) of longitudinal struts, such longitudinal struts being disposed about a central space into which the IVUS catheter may be advanced. One of such longitudinal struts may be aligned or specifically positioned in relation to the path that will be followed by the tissue penetrating element as it passes from the catheter, thereby providing on the display of the image received from the IVUS catheter, an artifact of other indication delineating the path or direction in which the tissue penetrating element will pass. The tissue-penetrating catheter may then be selectively rotated to aim the tissue penetrating element into the lumen of the artery or other target anatomical structure into which it is intended to pass.

b) Soft Distal Tip Member:

The catheter may incorporate a soft distal tip member that is formed or mounted on the distal end of the tissue-penetrating catheter (e.g., on the distal aspect of the above-described orientation structure). Such soft tip member is preferably formed of material which is soft enough to avoid trauma to the walls of the blood vessels through which the tissue-penetrating catheter is passed. A lumen may extend longitudinally through the soft tip member, to allow the operator to selectively advance the IVUS catheter or other device beyond the distal end of the tissue-penetrating catheter when it is desired to image blood vessels or other structures located distal to the then-current position of the tissue-penetrating catheter or perform other diagnostic functions with said IVUS catheter or other device.

c) Tissue Penetrating Member Stabilizer:

In embodiments wherein the tissue penetrating element is a needle or other elongate member that is advanceable laterally from the catheter body, the tissue penetrating catheter may incorporate a stabilizer to prevent or deter the tissue penetrating member from rotating or deviating from a predetermined acceptable penetration zone (APZ) (hereinafter sometimes referred to as the "stabilizer"). As used herein, the term stabilizer shall mean any structural or functional attributes of the catheter and/or tissue penetrating member that deter or prevent the tissue penetrating member from rotating or otherwise deviating from its intended path of advancement within a predetermined acceptable penetration zone (APZ). Examples of such structural and/or functional attributes include but are not limited to; curved distal housing formed to mirror the curve or form of the tissue penetrating element, engagement projections or elements for frictional engagement between the tissue penetrating member and the catheter body, bushings or narrowed/reduced diameter regions of the tissue penetration member lumen that serve to constrain the tissue penetrating member preventing side-to-side play or movement thereof, permanent magnets or electromagnets that create a magnetic field that prevents or deters lateral or rotational movement of the tissue penetrating member, etc. More specifically, for example, this stabilizer may comprise one or more of the following:

i) a curved needle housing which mates (i.e. has the same direction of curvature) with a preformed curvature formed in the needle. This mating of the curvatures of the needle and needle housing serves to deter unwanted rotation and resultant lateral deviation (flopping or wagging) of the portion of the needle which extends out of the catheter body;

ii) frictionally engaged surfaces formed on the needle member and surrounding catheter body (e.g., the wall of the lumen in which the needle member is disposed) to lock or deter rotation of the needle member relative to the catheter body;

iii) a steering mechanism for causing the distal portion of the catheter body to become curved in the direction in which the needle member is intended to advance so as to cause the preformed curve of the needle member to mate with the induced curvature of the surrounding catheter body; and, iv) A laterally deployable needle guide member (e.g., a balloon or rigid annular structure) that is deployable from side of the tissue penetrating catheter adjacent to the outlet opening through which the tissue penetrating member passes to support and prevent unwanted lateral "play" or movement of the tissue penetrating member as it is advanced from the catheter. This outwardly deployable needle guide member is initially disposed in a "stowed" position wherein it does not protrude (or only minimally protrudes) from the catheter body, and is subsequently deployable to an "active" position wherein it protrudes laterally from the catheter body, in the area of the needle outlet aperture, to provide support and/or guidance for the advancing tissue penetrating element (e.g., needle member or flow of energy) as the tissue penetrating element passes from the catheter body to the target location. This laterally deployable needle guide member may comprise a tubular cuff that has a lumen. The lumen of such tubular cuff may form, in combination with the catheter lumen in which the tissue penetrating element is positioned, a curvature that mates with or conforms to the preformed or intended curvature of the path of the tissue penetrating element as it passes from the catheter to the target location. In cases where the tissue penetrating element is a curved needle, the curvature of the laterally deployable needle guide member and/or catheter lumen may mate with or be the same as the curvature of the needle member.

d) Needle Member Locking Apparatus:

The tissue penetrating catheter may incorporate an apparatus that prevents or deters rotation of the tissue penetration member within the catheter body prior to its advancement out of the catheter. Such rotational locking of the tissue penetrating member while it is in its retracted position serves i) to maintain the desired rotational orientation of the needle member and ii) to enhance or couple the transfer of torque from the proximal end of the catheter to the distal end of the needle, without the addition of mass or cross-sectional dimension to the catheter body.

e) Catheter Body Construction:

The tissue penetrating device may comprise an elongate catheter body 12 with proximal, medial and distal segments of varying flexibility and torque strength as described more fully in U.S. patent application Ser. No. 08/837,294, incorporated herein by reference. Said catheter body may incorporate reinforcement members such as a reinforcement braid member which imparts structural integrity/stability as well as enhancing the ability of the catheter body to transmit torque along its length. In addition, it may be important for said reinforcement member to maintain the longitudinal integrity of said catheter body, and to minimize any variability of the catheter components during operation in the body.

B. Methods:

Further in accordance with the invention, there are provided methods for using the above-summarized catheter system to bypass an obstruction in a coronary artery by forming one or more arterio-venous passageways. Examples of these methods are the Percutaneous In Situ Coronary Artery Bypass (PICAB), as well as the Percutaneous Coronary Venous Arterialization (PICVA). It is understood that the same orientation steps and procedures may be used to access various targets and anatomical structures from placement of a tissue penetrating catheter within a blood vessel and orienting said catheter in accordance with this invention.

i. Percutaneous In Situ Coronary Artery Bypass (PICAB)

The PICAB procedure generally comprises the following steps:

1. Introduce a coronary sinus guide catheter into the coronary sinus;
2. Pass a tissue-penetrating catheter of the above-described type through the guide catheter and into the coronary vein;
3. Position an IVUS catheter or ultrasound transducer within the orientation structure of the tissue-penetrating catheter, and utilize the IVUS catheter or ultrasound transducer to view the artery into which the arterio-venous passageway is to extend as well as the marker that denotes the path that will be followed by the tissue penetrating member as it is advanced from the catheter body;
4. Rotate or move the tissue-penetrating catheter, as necessary, to cause the needle path indicator generated by the marker to become aligned with the lumen of the artery; and,
5. Pass the tissue penetrating element from the catheter, through the wall of the vein in which the catheter is positioned, and into the lumen of the artery, thereby forming an initial arterio-venous passageway distal to the arterial obstruction. In some embodiments, the tissue penetrating element has a lumen extending longitudinally therethrough for passage of a guidewire from vessel to vessel.
6. Move the catheter to a second location and repeat steps 4-6 to form an initial arterio-venous passageway proximal to the arterial obstruction.
7. Enlarge the proximal and distal arterio-venous passageways, if necessary, to permit the desired volume of blood flow through such passageways.
8. Place connector(s), stent(s), liner(s) or other stenting or connecting devices within the proximal and/or distal passageways, if necessary, to maintain the patency of the passageways; and,
9. Optionally, if necessary, place one or more blocker(s) within the coronary vein, or otherwise fully or partially block blood flow through the coronary vein, at location(s) that urge arterial blood to flow from the artery, through the first passageway and into the vein, through a segment of the vein, through the second passageway, and back into the artery (downstream of the blockage), thereby restoring arterial blood flow to the ischemic myocardium.

ii. Percutaneous Coronary Venous Arterialization (PICVA)

Further, in accordance with the present invention, there is provided a method for Percutaneous In Situ Coronary Venous Arterialization (PICVA) procedure, using a catheter system of the foregoing character. This preferred PICVA procedure generally comprises the steps of:

1. Introduce a coronary sinus guide catheter into the coronary sinus;
2. Pass a tissue-penetrating catheter of the above-described type through the guide catheter and into the coronary vein;
3. Position an IVUS catheter or ultrasound transducer within the orientation structure of the tissue-penetrating catheter, and utilize the IVUS catheter or ultrasound transducer to view the artery into which the arterio-venous passageway is to extend as well as the marker that denotes the path that will be followed by the tissue penetrating member as it is advanced from the catheter body;

4. Rotate or move the tissue-penetrating catheter, as necessary, to cause the needle path indicator generated by the marker to become aligned with the lumen of the artery; and,
5. Pass the tissue penetrating element from the catheter, through the wall of the vein in which the catheter is positioned, and into the lumen of the artery, thereby forming an initial arterio-venous passageway distal to the arterial obstruction. In some embodiments, the tissue penetrating element has a lumen extending longitudinally therethrough for passage of a guidewire from vessel to vessel.
6. Enlarge the initial arterio-venous passageways, if necessary, to permit the desired volume of blood flow through such passageway.

Place connector(s), stent(s), liner(s) or other stenting or connecting devices within the arterio-venous passageway, if necessary, to maintain the patency of the passageway; and, Optionally, if necessary, place one or more blocker(s) within the coronary vein, or otherwise fully or partially block blood flow through the coronary vein, at location(s) that urge arterial blood to flow from the artery, through the arterio-venous passageway and into the vein, such that the arterial blood will flow through the vein in a direction opposite normal venous flow, thereby retro-perfusing the ischemic myocardium by arterialization of the coronary vein.

Further aspects and advantages of the present invention will become apparent to those of skill in the art upon reading and understanding the detailed description of preferred embodiments set forth herebelow and the accompanying drawings.

BRIEF DESCRIPTION OF THE DRAWINGS

FIG. 1a is a broken, side elevational view of a first embodiment of a tissue-penetrating catheter of the present invention.

FIG. 1a' is a broken, side view of the catheter body construction of the catheter shaft of a tissue penetrating catheter of the present invention.

FIG. 1a" is a detailed view of the braided construction of the catheter shaft of FIG. 1a'.

FIG. 1b is an enlarged view of the distal end of the catheter shaft of FIG. 1a.

FIG. 1c is a cross sectional view through line 1c-1c of FIG. 1a.

FIG. 1d is a cross sectional view through line 1d-1d of FIG. 1a.

FIG. 1e is an enlarged, side elevational view of the needle housing/stabilizer assembly of the catheter of FIG. 1a.

FIG. 1f is a cross sectional view through line 1f-1f of FIG. 1e.

FIG. 1f' is a cross sectional view through line 1f'-1f' of FIG. 1f.

FIG. 4 is a side elevational view of a subselective sheath and accompanying introducer that are useable in combination with the tissue-penetrating catheter of the present invention.

FIG. 4a is a side elevational view of a dilator that is insertable through and useable in conjunction with the subselective sheath of FIG. 4.

FIG. 5 is a partial longitudinal sectional view of the subselective sheath of FIG. 4 having the dilator of FIG. 4a operatively inserted therein.

FIG. 5a is an enlarged, cross sectional view through line 5a-5a of FIG. 5.

FIG. 6 is an enlarged, longitudinal sectional view of the distal portion of the subselective sheath of FIG. 4.

FIG. 7 is a side elevational view of the tissue puncturing needle member of the tissue-penetrating catheter of FIG. 1a.

FIG. 8a is an enlarged, side elevational view of the distal end of the needle member of FIG. 7.

FIG. 8b is an enlarged top view of the of the distal end of the needle member of FIG. 7.

FIGS. 9 & 9a show the hand piece/needle controller and distal end, respectively, of tissue-penetrating catheter of FIG. 1a with its tissue penetrating needle member in its retracted position.

FIGS. 10 & 10a show the handpiece/needle controller and distal end, respectively, of tissue-penetrating catheter of FIG. 1a with its tissue penetrating needle member in its fully advanced position.

FIG. 10d is a side elevational view of an optional rotation-inhibiting key insert and corresponding keyed needle member which may be incorporated into the tissue-penetrating catheters of the present invention to prevent the tissue-penetrating needle member from rotating relative to the body of the catheter.

FIG. 10d' is a cross sectional view through line 10d'-10d' of FIG. 10d.

FIG. 10d" is a cross sectional view through line 10d"-10d" of FIG. 10d.

FIG. 10e is a side elevational view of an optional rotation-inhibiting oval insert and corresponding oval shaped needle member which may be incorporated into the tissue-penetrating catheters of the present invention to prevent the tissue-penetrating needle member from rotating relative to the body of the catheter.

FIG. 10e' is a cross sectional view through line 10e'-10e' of FIG. 10e.

FIG. 10e" is a cross sectional view through line 10e"-10e" of FIG. 10e.

FIG. 10f' is an enlarged view of region 10f' of FIG. 10f.

FIG. 10g is a side elevational view of a tissue-penetrating catheter of the present invention having a laterally deployable needle stabilizer disposed in its "stowed' position.

FIG. 10g' is a side elevational view of a tissue-penetrating catheter of the present invention having a laterally deployable needle stabilizer disposed in its "active" position.

FIG. 11 is a side elevational view of a coronary sinus guide catheter/introducer assembly of the present invention.

FIG. 11a is a cross-sectional view through line 11a-11a of FIG. 11.

FIG. 11b is an enlarged, longitudinal sectional view of the proximal end/hemostatic valve of the coronary sinus guide catheter shown in FIG. 11.

FIG. 11c is broken, side elevational view of the introducer of the coronary sinus guide catheter/introducer assembly.

FIGS. 14a-14l are schematic, step-by-step showings of a preferred method for performing a percutaneous coronary venous arterialization (PICVA) procedure to provide retrograde arterial bloodflow through a coronary vein.

DETAILED DESCRIPTION OF PREFERRED EMBODIMENTS

Figure 1:
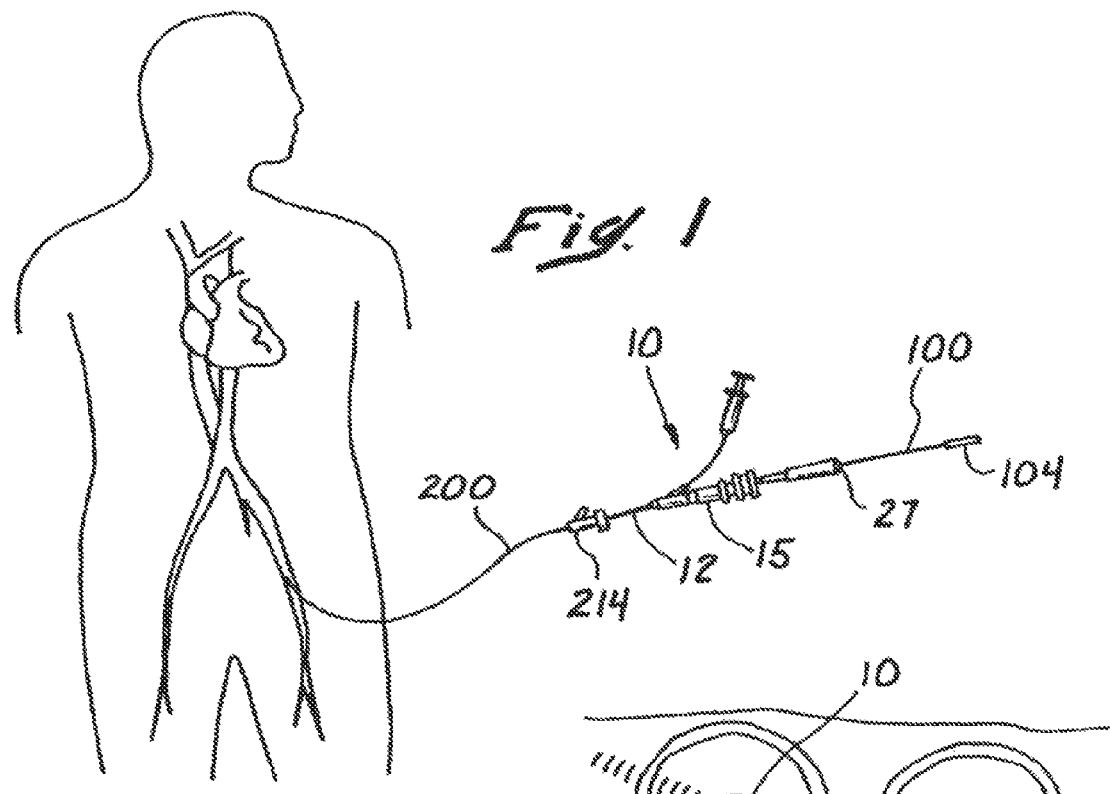
FIG. 1 is a schematic showing of a human being having a tissue-penetrating catheter system of the present invention percutaneously inserted via a femoral entry site.

The following detailed description, and the drawings to which it refers, are provided for the purpose of describing and illustrating certain preferred embodiments or examples of the invention only, and no attempt has been made to exhaustively describe all possible embodiments or examples of the invention. For example, the tissue penetrating catheter of this invention may be utilized is numerous locations in the body to reliably access organs, tissue or other structures to deliver therapeutic substances or procedures. Thus, the following detailed description and the accompanying drawings are not intended to limit, in any way, the scope of the claims recited in this patent application and any patent(s) issuing therefrom.

A. The Catheter System:

Referring generally to FIGS. 1-12, a presently preferred catheter system of the present invention generally comprises i) a tissue-penetrating catheter component 10 (FIGS. 1-3 and 7-10 a), ii) a subselective sheath/introducer component 100 (FIGS. 4-6) and iii) a coronary sinus guide catheter/introducer component 200 (FIGS. 11-11c). Each of these components is described in substantial detail herebelow. These components of the catheter system may be packaged together in a single kit, or may be provided in separate packages to permit the operator to mix and match component sizes in accordance with the particular anatomy of the patient, the size of the channels to be formed, the types of connectors and/or stents and/or blockers to be used, etc.

Figure 2:
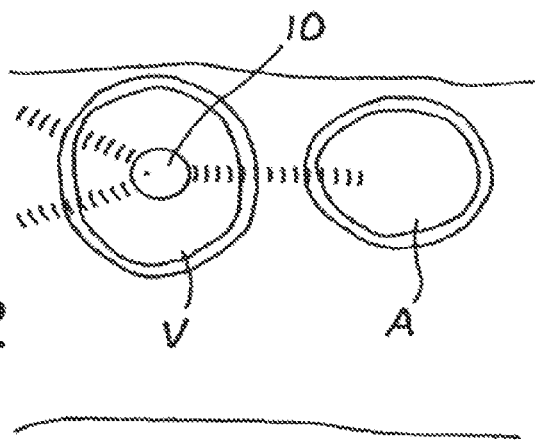
FIG. 2 is a representation of the intravascular ultrasound image that is obtained when the tissue-penetrating catheter of FIG. 1a is positioned within a coronary vein and properly oriented/aimed such that deployment of its tissue penetrating member will form a penetration tract (i.e., a passageway) from the coronary vein to an adjacent coronary artery.
Figure 3:
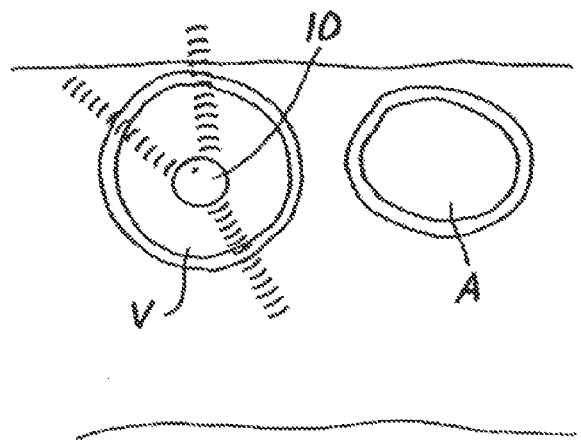
FIG. 3 is a representation of the intravascular ultrasound image which is obtained when the tissue-penetrating catheter of FIG. 1a is positioned within coronary vein and improperly oriented/aimed such that deployment of its tissue penetrating member will not form a passageway from the coronary vein to the adjacent coronary artery.

I. The Tissue-Penetrating Catheter Component of the Catheter System:

Referring to FIGS. 1-3 and 7-10 there is shown a tissue-penetrating catheter device 10 which is insertable into the vasculature of a mammalian patient and useable to form passageways (e.g., puncture tracts) between the blood vessel in which the distal end of the catheter device 10 is situated and another blood vessel or other anatomical structure. This catheter device 10 generally comprises an elongate, flexible catheter body 12 having a proximal portion $12_P$ of a first diameter $D_1$ and a distal portion $12_D$ of a second diameter $D_2$ which is smaller than the first diameter $D_1$. The catheter body 12 has two (2) lumens 14, 16 which extend longitudinally therethrough. The first lumen 14 is sized and configured to permit a standard commercially available IVUS catheter (e.g., those available from Endosonics of Rancho Cordova, Calif.; CVIS of Natick, Mass. or Hewlett-Packard of Andover, Mass.) to be inserted therethrough and slidably disposed therewith. The second lumen 16 is sized and configured to house a tissue penetrating needle member 30 (see FIGS. 7, 9 and 10) which is alternately moveable between i) a retracted position (FIGS. 9-9a) wherein the distal end DE of the needle member 30 is contained within the catheter body 12, and ii) an extended position (FIGS. 10-10a) wherein the needle member 30 is advanced out of the catheter body 12 so as to penetrate through the walls of the blood vessels and through any intervening tissue located between the blood vessels.

a. Orientation Structure:

An orientation structure 36 and tip member 38 are formed integrally with or mounted on the distal end of the catheter body 12, as shown in FIGS. 1b, 9a and 10a. The orientation cage 36 comprises first 40, second 42 and third 44 strut members which extend longitudinally between the distal end of the catheter body 12 and the proximal end of the distal tip member 38. The first strut member 40 is in direct longitudinal alignment with a needle outlet opening 46 formed in the side of the catheter body 12 through which the tissue penetrating needle member 30 is advanced. The second and third strut members 42, 44 are located at equally spaced distances from the first strut member 40, while the distance between the second and third strut members 42,44 is less than the distance between either of those second and third strut members 42, 44 and the first strut member 40. Such disparate (e.g., unequal) radial spacing of these strut members 40, 44 and 46 allows the operator to easily identify and distinguish the first strut member 40 from the other two strut members 42, 44 by way of the image received from an IVUS catheter positioned within the orientation structure 36. Thus, in this manner, the operator may selectively rotate the catheter body 12 until the first strut member 40 is directly aligned or juxtapositioned with the target blood vessel into which the needle member 30 is to be advanced. An illustration of this technique is shown in FIGS. 2 and 3. FIG. 2 shows the IVUS image which is obtained when the tissue-penetrating catheter 10 is properly rotated such that the first strut member 40 is aligned with the target artery A and the needle member 30 will advance into such target artery A. FIG. 3 shows another situation where the tissue-penetrating catheter 10 is not properly rotated, the first strut member 40 is not aligned with the target artery A and the needle member 30, if advanced, would not enter the target artery A.

It will be appreciated that the disparate distancing of the strut members 40, 42, 44 is only one possible way of rendering the first strut member 40 distinguishable from the other two strut members 42, 44. Alternatively, the size or configuration of the first strut member could be different so as to produce a distinguishable ultrasound image or the material or surface characteristics of the first strut member 40 could be made different from the other two strut members 42, 44 such that the first strut member 40 would reflect more or less ultrasound than the other two strut members 42, 44 thus producing an ultrasound image which is distinguishable from the images produced by the other two strut members 42, 44. It will also be appreciated that only one strut member may be required to provide a distinguishable element to aid catheter orientation, or alternatively two strut members may be positioned to delineate a zone within which the tissue penetrating member may be deployed, or other procedure conducted.

b. Distal Tip Member:

The distal tip member 38 is preferably of blunt tipped configuration and is formed of smooth soft material (e.g., PEBAX having a durometer hardness of 35 D) so as to minimize trauma to the vasculature as the tissue-penetrating catheter device 10 is advanced or otherwise manipulated about. A hollow lumen 39 may extend longitudinally through the tip member 38, in alignment with the first lumen 14 of the catheter body 12, such that an IVUS catheter or other device such as a guidewire may be advanced from the first lumen 14, through the orientation structure 36, through the distal tip lumen 38 and distally beyond the catheter device 10. This permits the operator to use the IVUS catheter to explore areas which are ahead of the distal end of the tissue-penetrating catheter without having to advance the tissue-penetrating catheter from its then-present position. It also permits the catheter device 10 to be introduced to the vasculature in the preferred "over the wire" manner.

c. Tissue Penetrating Needle Member:

The tissue penetrating element of the tissue penetrating catheter may comprise a sharp tipped needle 30 as shown in FIGS. 7, 8a and 8b. This needle 30 includes a proximal shaft 30p formed of stainless steel hypotubing and a resilient, curved distal portion 30d formed of a resilient material or, more preferably, a material such as NiTi alloy. Preferably a lumen 31 extends longitudinally through the proximal shaft 30p and the curved distal portion 30d.

The particular radius of curvature of the curved distal portion 30d may be an important factor in determining the trajectory and path of the needle tip as it advances and the point at which the needle tip will stop when in its fully advanced position.

The distal tip of the needle member 30 is preferably sharpened so as to easily penetrate through the walls of the blood vessels and any intervening tissue located therebetween. One preferred needle tip configuration is the lancet type bevel 36 shown in FIGS. 8a and 8b. This lancet type bevel comprises a first radial surface 36a and a second radial surface 36b. Such lancet type tip 36 provides excellent tissue-penetrability and retains its sharpness after multiple retractions into/advancements from the catheter. In practice it may be important for the material surrounding the lumen of the needle, particularly at the distal tip of the needle, and particularly the heel of the needle lumen 36c, to be smooth and free of rough edges or burrs. This allows smooth passage of devices, such as guidewires, through the needle lumen.

Figure 10F:
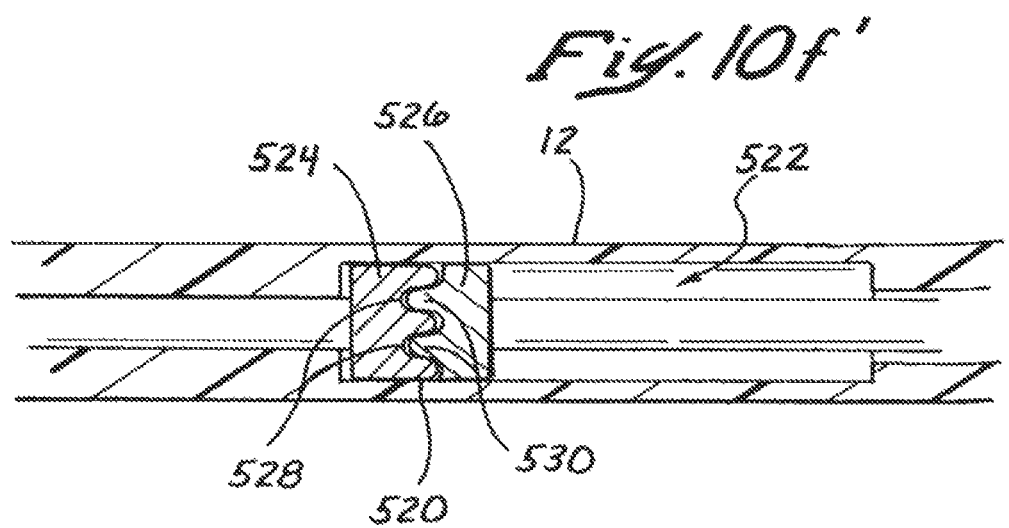
FIG. 10f is a partial longitudinal sectional view of a tissue-penetrating catheter device of the present invention incorporating an optional locking collar apparatus for preventing the tissue penetrating needle member from rotating relative to the catheter body when the needle member is in its retracted position.
Figure 12:
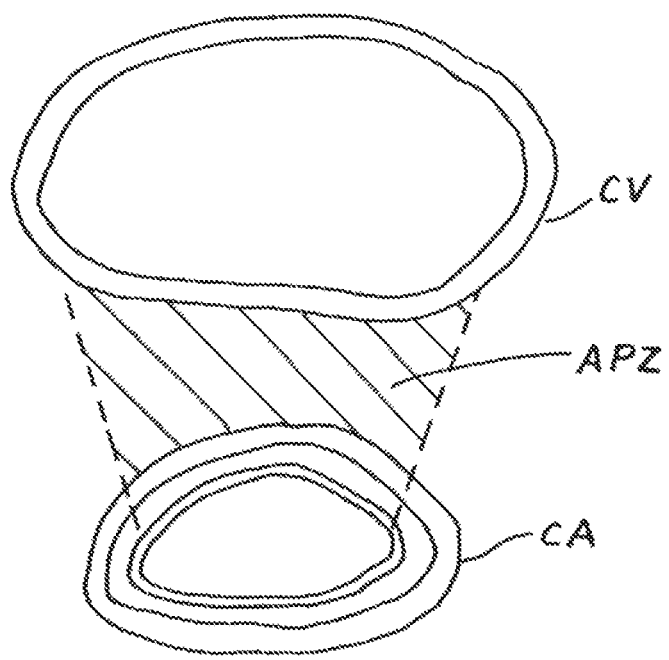
FIG. 12 is an enlarged, cross-sectional view through a coronary artery and adjacent coronary vein, showing the typical difference in diameter of the artery and vein, and delineating a preferred Acceptable penetration zone (APZ) wherein the arterio-venous bloodflow passageways of the present invention are formed.

In many applications, the controllability and aiming of the needle member 30 may be enhanced by constraining the needle member 30 such that it will remain in a preferred plane or acceptable penetration zone APZ as shown in FIG. 12, as it is advanced from the catheter. In embodiments where a curved needle member 30 is advanced out of a side aperture in the catheter (e.g., the embodiment shown in FIG. 10a), any rotation of the needle member 30 prior to, during or after advancement of the needle member 30 can cause the distal end of the curved needle member to deviate from or move out of the intended plane or acceptable penetration zone APZ. In this regard, the potential for such unwanted lateral movement of the distal end of the needle member 30 may be prevented or substantially limited by providing a stabilizer to prevent or substantially limit the amount of rotation that the needle member 30 may undergo relative to the catheter body 12 or to otherwise prevent or deter the needle member from deviating from a predetermined acceptable penetration zone APZ (FIG. 12) as it is advanced from the catheter 10. In particular, by preventing or limiting the rotation of the needle member 30 within the needle lumen 16, the curved distal portion of the needle member will be deterred from deviating from its intended path of advancement as it is extended laterally from the catheter body 12 (see FIG. 10a). Such prevention or limitation of the potential for rotation or lateral movement of the needle member 30 may be accomplished in any suitable way. As described in detail herebelow, specific apparatus which may be incorporated into the catheter device 10 to prevent or deter rotation or lateral movement (i.e., "wagging" or "flopping") of the needle member 30 during or after its advancement from the catheter body 12, include:

a) a curved needle housing 60 which has a curve at its distal end which mates with the preformed curvature of the needle member 30 to deter rotation (see FIGS. 9-10f);

b) engaged surfaces 76, 77 formed on the needle member 30 and surrounding catheter body 12 to lock or deter rotation of the needle member 30, examples of such engaged surfaces 76, 77 including but not necessarily being limited to i) a tongue in groove or key in key-way arrangement (see FIGS. 10d-10d") or ii) an oval to oval arrangement (see FIGS. 10e-10"), etc;

c) a steering mechanism for causing the distal portion of the catheter body 12 to curve in the lateral direction in which the needle member 30 is intended to advance so as to cause the preformed curve of the needle member 30 to mate with the induced curvature of the catheter body 12; and, d) a needle guide member 500 which is laterally projectable from the catheter body 12 in the area of the needle outlet aperture 46 to support the needle member 30 and/or to form a lateral extension of the needle lumen 16 so as to create a lateral curve in the needle lumen which mates with the preformed curvature of the needle member 30 (see FIG. 10 g).

i. Curved Needle Housing to Deter Rotation/Lateral Deviation of Extended Needle

An example of a preferred curved needle housing 60 mountable within the needle lumen 16 is specifically shown in FIGS. 1b-1f. Such needle housing 60 comprises a curved, rigid tube. A tubular liner 61 may be disposed within, and may extend from either end of, the curved needle housing 60. Such tubular liner 61 may be formed of a three-layer composite wherein the inner layer is a lubricious polymer material (e.g., polytetrafluoroethylene (PTFE)), the middle layer is a structural polymer material (e.g., polyimide) and the outer layer is an adhesive material which will bond to the inner surface of the curved needle housing 60 and to the inner surface of the needle lumen 16 at either end of the housing 60 (e.g., polyurethane adhesive). When the needle member 30 is in its retracted position (FIGS. 9 and 9a), and during advancement, the portion of the needle member which resides within the needle housing 60 will remain in a slightly curved state in conformance to the slightly curved configuration of the needle housing 60. This serves to deter the needle member 30 from rotating relative to the catheter body 12 and/or from undergoing uncontrolled movement (i.e., "flopping") out of the intended acceptable penetration zone APZ, during or after advancement from the catheter. This prevention or deterrence from rotation of the needle member 60 allows the operator to control the orientation of the lancet type or other bevel formed in the needle tip, and also enhances the operator's ability to predict the precise position of the needle tip by eliminating or minimizing the uncontrolled side-to-side movement of the needle. To facilitate the desired positioning and orientation of the curved needle housing 60 during manufacture of the catheter 10, a locator member 62 may be attached to the needle housing 60 and incorporated into the catheter body 12 as shown in FIGS. 1b, 1e, 1f, 1f', 9a and 10a. This locator member 62 comprises a rigid disc 64 which is transversely positionable within the catheter body, having a first bore 66 and a second bore 68 extending longitudinally therethrough. A chamfered edge 69 is formed about the proximal end of the first bore 66, as shown in FIGS. 1f and 1f'. During manufacture of the catheter body 12, a rod or mandrel is inserted through the first bore 66 of the locator and into the first lumen 14 of the proximal catheter body portion $12_P$ and the curved needle housing 60 having a tubular liner 61 extending therethrough and protruding for either end, are inserted through the second bore 68 and into the second lumen 16 of the proximal catheter body portion 12$_P$. Thereafter, a distal plastic tube is advanced about the locator, a tubular polymer skin 73 is applied, and the composite is then heated to form the distal portion of the catheter body 12, as shown.

ii. Frictionally Engaged Surfaces of Needle Member and Catheter to Deter Rotation/Lateral Deviation of Extended Needle:

As an alternative to, or in addition to, the use of the curved needle housing 60 as a means for preventing rotation of the needle member 30 and for providing more accurate and stable deployment of the needle member 30, the needle member 30 and at least a portion of the second lumen 14 may incorporate engaged surfaces which are frictionally engaged to one another so as to prevent or deter rotation of the needle member 30 within the needle lumen 16. Examples of such engaged surfaces 76, 77 include a key/key-way design shown in FIGS. 10*d*-10*d'''* or an oval/oval design such as that depicted in FIGS. 10*e*-10*e''*.

With specific reference to the showings of FIGS. 10*d*-10*d'''*, the key/keyway method of preventing independent rotation of the needle member 30 may be effected by use of a key-way element 76 in combination with a keyed needle 30$_{key}$. The key-way element 76 comprises a tubular member which has a key-way shaped lumen 77 with a key portion 79 extending longitudinally therethrough. The keyed needle 30$_{key}$ comprises a hollow needle of the type described hereabove and shown in FIGS. 7-8*b* having a longitudinally extending rail or key member 33 formed upon a segment thereof. The key member 33 may be formed as a portion of the needle wall or may alternatively comprise a separate member, such as a section of hypotube, affixed to the side of the needle wall. The keyed needle 30$_{key}$ is sized and configured to be advanced and retracted through the lumen 77 of the key-way housing, with the key member 31 being disposed within the key portion 79 of the lumen 77. In this manner the keyed needle member 30$_{key}$ is longitudinally advanceable and retractable, but can not be rotated within the lumen 77 due to the engagement of the needle key member 31 with the key portion 79 of the lumen 77. The key-way element 76 is provided with a stabilizer 78 which is substantially the same as the needle housing stabilizer 62 described above and shown in FIGS. 1*e*-1*f'*, and the key-way element 76/stabilizer 78 assembly may be installed and mounted within the catheter body at the time of manufacture in the same manner as described hereabove with respect to the needle housing 60/stabilizer 62 assembly shown in FIGS. 1*e*-1*f'*. This key-way element 76/stabilizer 78 assembly is typically installed and mounted in the catheter body 12 proximal to the location of the needle housing 60/locator 62 assembly shown in FIGS. 1*e*-1*f'* but near enough to the distal end of the catheter device 10 to prevent the portion of the needle adjacent its distal end from undergoing untoward rotation within the catheter body 12 during the catheter insertion procedure.

With specific reference to the oval/oval arrangement shown in FIGS. 10*e*-10*e''*, the device 10 may incorporate an oval shaped needle housing 76$_{alt}$ in combination with an oval shaped needle 30$_{ov}$. The oval shaped needle housing 76$_{alt}$ comprises a tubular member positioned within the needle lumen 16 and having an oval shaped lumen 77$_{alt}$ extending longitudinally therethrough. The oval shaped needle 30$_{ov}$ comprises a hollow needle of the type described hereabove and shown in FIGS. 7-8*b* having an oval, ovoid or other non-round cross-sectional configuration. The oval shaped needle 30$_{ov}$ is sized and configured to be advanced and retracted through the lumen 77$_{alt}$ of the oval shaped needle housing 76$_{alt}$, but can not be rotated within the lumen 77$_{alt}$ due to the engagement of the oval shaped needle member 30$_{ov}$ with the oval shaped wall of the housing lumen 77$_{alt}$. The oval shaped needle housing 76$_{alt}$ is provided with a locator 78 which is substantially the same as the needle housing locator 62 described above and shown in FIGS. 1*e*-1*f'*, and the oval shaped needle housing 76$_{alt}$/locator 78 assembly may be installed and mounted within the catheter body 12 at the time of manufacture, in the same manner as described hereabove with respect to the needle housing 60/locator 62 assembly shown in FIGS. 1*e*-1*f'*. This oval shaped needle housing 76$_{alt}$/locator 78 assembly will typically be installed and mounted in the catheter body 12 proximal to the location of the needle housing 60/locator 62 assembly shown in FIGS. 1*e*-1*f'*, but near enough to the distal end of the catheter device 10 to prevent the portion of the needle 30$_{ov}$ adjacent its distal end from undergoing untoward rotation within the catheter body 12 during the catheter insertion procedure.

iii. Laterally Deployable Needle Guide to Deter Rotation/Lateral Deviation of Extended Needle:

FIGS. 10*g* and 10*g'* show an example of a needle guide member 500 which may be caused to project or extend laterally from the catheter body 12 in the area of the needle outlet aperture 46 to stabilize and guide the advancing needle member, thereby deterring lateral or side-to-side movement of the needle member 30 and further constraining the path which will be followed by the advancing needle. The deployment of such needle guide member 500 may also give rise to a lateral extension of the needle lumen 16 which mates with the preformed curve of the needle member 30 to prevent rotation of the needle member 30 in essentially the same manner as the curved needle housing 60 described above.

The particular laterally deployable guide member 500 shown in FIGS. 10*g* and 10*g'* is an inflatable annular member that is connected to an inflation fluid lumen 502 that extends through the catheter body 12 to permit inflation fluid to be infused and withdrawn from the inflatable guide member 500. When deflated (FIG. 10*g*) the guide member 500 will nest within a depression or cut out region in the catheter's outer wall thereby assuming a configuration that is substantially flush with the outer surface 504 of the catheter body 12. When inflated (FIG. 10*g'*) the guide member 500 will form an annular support collar around the tissue penetrating member 30 as it advances laterally from the catheter body. The surface(s) of the inflatable guide member 500 that may be brushed against or contacted by the tip of the tissue penetrating member as it advances out of the outlet opening 46 may be armored or coated with a metal foil or other material that will resist puncture by the tip of the tissue penetrating member 30.

iv. Steerable Catheter Body to Deter Rotation/Lateral Deviation of the Extended Needle Member:

The catheter body 12 may be provided with a mechanism for inducing a curve or bend in the region of the catheter body 12 proximal to the needle outlet aperture 46 to cause the portion of the needle lumen 16 proximal to the outlet aperture 46 to assume a curvature which mates with the curved shape to which the needle member 30 is biased, thereby deterring rotation of the needle member 30 within the catheter in the same manner described above with respect to the curved needle housing 60. The mechanism by which the catheter body 16 may be induced to curve may be any suitable catheter steering apparatus known in the art, such as an internal pull wire or spine member formed on shape memory alloy which is alternately transitionable between a straight configuration and a curved configuration.

v. Rotational Locking of Needle Member when Retracted to Maintain Correct Orientation and Enhance Torque Transfer:

It is desirable for the proximal shaft of the tissue-penetrating catheter 10 to be endowed with enough structural integrity to transmit torque to the distal end of the catheter, as necessary for precise rotational orientation and aiming of the catheter device 10 before advancement of the needle member 30 therefrom. Also, in many applications, it is desirable for the needle member 30 to be maintained in a predetermined rotational orientation within the catheter body 12 prior to advancement of the needle member 30 from the catheter 10 (i.e., while the needle member 30 is still in its retracted state). In many applications, it is also desirable to minimize the diameter of the catheter body 12 to allow it to pass through small blood vessel lumens. Each of these three (3) objectives may be achieved by rotational locking of the needle member 30 within the catheter body prior to its advancement from the catheter, as such rotational locking i) prevents unwanted needle rotation, ii) enhances the efficiency of torque transfer to the distal end of the catheter body 12 and thereby the needle, and iii) does not add any mass or additional diameter to the catheter body 12.

FIGS. 10f-10f' show a needle locking collar assembly 520, which comprises an enlarged region 522 formed within the needle lumen 16, wherein a first locking collar member 524 and second locking collar member 526 are located. The first locking collar member 524 is stationarily affixed to the catheter body 12 and has cavities or grooves 528 formed in the distal surface thereof and a central aperture through which the needle member $30_{col}$ may be advanced and retracted. The second locking collar member 526 is affixed to the needle member $30_{col}$ and has projections 530 extending from the proximal surface thereof. The projections 530 are sized, located and configured to be received within the grooves 528 of the first collar member 524 when the needle member $30_{col}$ is in its retracted position, thereby frictionally locking the needle member $30_{col}$ to prevent its rotation relative to the catheter body 12. However, when the needle member $30_{col}$ is in its extended position, the projections 530 will not be inserted within the grooves 528, and the collar assembly 520 will not prevent the needle member $30_{col}$ from rotating within the catheter body 12. It will be appreciated that these stabilizing devices may be employed at various points along the length of the catheter body, including the proximal, medial, distal or needle housing portion.

d. Handpiece/Needle Controller:

A handpiece/needle controller 15 is mounted on the proximal end of the Catheter body 12, and is useable to control the rotational orientation of the catheter body 12 and the advancement/retraction of the needle member 30.

Also this handpiece/needle controller 15 has a proximal port 27 formed on its proximal end through which a small guidewire (e.g., a 0.0010-0.016 inch diameter wire) may be advanced through the lumen 31 of the needle member 30, a first side port 21 through which a large guidewire (e.g., a 0.030-0.040 inch diameter wire) may be advanced through the first lumen 14 when that first lumen 14 is not occupied by an IVUS catheter, and a second side port 23 through which a flush solution may be infused into the catheter's second lumen 16 outside of the needle member 30 disposed therein.

e. Catheter Body:

The catheter body 12 includes a relatively stiff proximal section 12a, a medial section 12b, and a distal section 12c shown in FIGS. 1A and 1B. The catheter body exhibits varying flexibility and torque strength along its length, and may incorporate reinforcement members such as a reinforcement braid member which imparts structural integrity as well as enhancing the ability of the catheter body to transmit torque. A hand piece 15 is attached to the proximal end of the proximal section 12a, as shown. In the preferred embodiment the hand piece 15 and proximal section 12a are approximately 115 cm in length. The medial section extends approximately 25 cm terminating approximately 2 cm from the distal section 12c. The proximal and medial sections of the catheter contain a braided component 50 as shown in FIGS. 1B' and 1B", encased in a polymer material (e.g. Pebax, nylon, polyurethane, polyester or PVC) extruded to form the inner lumen 50b and out jacket 50a of catheter body 12.

It has been determined that material expansion and changes in the physical properties of certain materials may occur after the catheter 10 is inserted into the patient's body and warmed from room temperature to body temperature. This material expansion and changes in the physical properties of certain materials can result in variation in the tolerances and sizing of the catheter 10 (e.g. elongation or shrinking) and can thus give rise to an unwanted modification of the position of the tissue penetrating member 30. This could, in at least some cases, interfere with the precise aiming and advancement of the tissue penetrating member as desired. FIG. 1B" illustrates the braid angle A and pick count PC of the catheter braid 50. The "pick count" PC of the braid is, as is well known in the art, a function of the braid angle A (i.e., the greater the braid angle the more picks per inch). Also, the torque transmission and stiffness of the braided section 50 is a function of the braid angle (i.e., a braid angle of 90 degrees provides maximum torque transfer and a braid angel of 0 degrees provides minimum torque transfer). Catheters used in the present invention that have exhibited this phenomenon have braid angles A that result in a pick count of 50-70 picks per inch. However, applicant has determined that by decreasing the braid angle A of the braid 50 within the proximal and medial sections of the catheter 10 to result in a pick count of 20-30 picks per inch, it is possible to minimize or eliminate the unwanted longitudinal expansion of the catheter 10 and/or its components, while retaining sufficient torque transmission and acceptable stiffness to accomplish the procedures for which the catheter 10 is intended (examples of such procedures are illustrated in FIGS. 13a-14l herebelow). This variation in braid angle or picks per inch may vary depending on the material of construction of the catheter and/or the braid fiber, and the diameter of the catheter body.

II. The Coronary Sinus Guide Component of the Catheter System:

FIGS. 11-11c show a preferred coronary sinus guide catheter/introducer assembly 200, which comprises a) a flexible coronary sinus guide catheter 203 that has a curved distal portion 204, a proximal assembly 214 mounted on the proximal end of the flexible catheter body 203, and a hollow lumen 202 extending longitudinally therethrough and b) an introducer 213 that has a tapered, soft distal portion 213d that protrudes out of and beyond the distal end DE of the guide catheter 203 and a guidewire lumen 215 that extends longitudinally through the introducer 213 to permit the guide catheter/introducer assembly to be advanced over a guidewire GW as described more fully herebelow in connection with a preferred method of using the catheter system 10.

A reinforcement braid 212, such as a wire braid, is formed within a portion of the catheter body 203 but terminates approximately 2 to 5 centimeters from the distal end DE. In this manner, the reinforcement braid 212 will prevent kinking and improve torque strength of the proximal portion of the catheter body 203, and the curved portion thereof, up to a location at about 2 to 5 centimeters from its distal end DE.

The proximal assembly comprises a rigid body 248 through which the lumen 202 extends, and upon which a proximal port 250 is formed to permit the guide introducer 213, subselective sheath 100 (FIGS. 4-6), tissue-penetrating catheter device 10 (FIGS. 1 and 9-10), or other catheters, guidewires and/or devices (e.g., blocker delivery catheter, channel connector delivery catheter, channel enlarging device, etc. . . . ) to be inserted through the lumen 202 of the coronary sinus guide catheter 200. A hemostatic valve 244, such as a cross-cut resilient membrane, a slit-cut resilient membrane, or a flapper valve) is positioned transversely within the lumen 202 of the proximal assembly 214 to prevent blood from backflowing out of the proximal port 250 when no catheter or other device is inserted therethrough and to prevent or minimize the amount of blood which may leak out of the proximal port 250 when a catheter or other device is inserted therethrough. A side port 246 is formed on the proximal assembly 214 to permit preparation fluid to be infused or injected into or through the lumen 202. A plurality of side apertures 210 are formed in the wall of the catheter body 203 near its distal end to allow pressure relief in the event that a radiographic contrast medium or other fluid is injected.

III. The Subselective Sheath Component of the Catheter System

As shown in FIGS. 4-6, a preferred subselective sheath 100 of the present invention comprises a flexible sheath body 102 having a proximal hub 104 and a lumen 106 extending longitudinally therethrough. A reinforcement braid 108 is formed within the catheter body 102 to prevent kinking and improve torque strength. Such reinforcement braid terminates distally at 0.1-1.0 centimeter from the distal end of the catheter body 102. A gradual taper 110 is formed about the distal end of the sheath body's outer surface to such that the sheath 100 will taper to a flush transition with the distally protruding portion 111$d$ of its introducer 111. The lumen 202 has an inner diameter D1 which is substantially the same as the outer diameter of the introducer 111 that is initially inserted through the lumen 106. The introducer 111 has a guidewire lumen 109 that extends longitudinally therethrough to permit the subselective sheath/introducer assembly to be advanced over a previously inserted guidewire GW (e.g., a 0.035 inch guidewire). The outer diameter of the sheath 100 is sized to be advanced and retracted through the lumen 202 of the coronary sinus guide catheter 200 (FIGS. 11-11$b$). The preferred method of using this subselective sheath 100 and introducer 111 are described in detail herebelow with respect to the methods of the present invention.

B. Preferred Methods for Using the Catheter System:

The present invention also includes methods for using this catheter system described hereabove (or any other catheter system or devices that may be suitable to carry out the desired purpose), in conjunction with other apparatus such as guidewires, channel enlarging catheters/devices, channel connecting catheters/devices and vessel blocking catheters/devices to perform percutaneous, in situ coronary arteriovenous bypass procedures by way of a vein-to-artery approach, such method being fully described herebelow and shown in step-by-step fashion in FIGS. 13$a$-13$x$ and 14$a$-14$l$.

The catheter system described hereabove and shown in FIGS. 1-11$b$ is useable in conjunction with a fluoroscope, an IVUS imaging catheter, a coronary sinus access catheter (e.g., a standard angiographic catheter), a channel-enlarging catheter device, lumen-blocking device(s), a 0.035 inch diameter guidewire, and one or more 0.014 inch diameter guidewire(s) to perform various revascularization procedures including, as described in detail herebelow, a Percutaneous In Situ Coronary Artery Bypass (PICAB) procedure as well as a Percutaneous In Situ Coronary Venous Arterialization (PICVA) procedure. It will be appreciated that, in addition to the particular PICAB and PICVA examples described in detail herebelow, the catheter system of the present invention may also be useable to perform various other procedures such as directed drug delivery procedures of the type described in co-pending U.S. patent application Ser. No. 09/048,147 and other revascularization procedures.

I. A Preferred Method for Performing the PICAB Procedure:

FIGS. 13$a$-13$x$ show, in step-by-step fashion, an example of a PICAB procedure wherein the catheter system 10 of the present invention is used for the purpose of bypassing a blockage located in the proximal portion of the Anterior Descending Coronary Artery (LAD) of a human patient. In this PICAB procedure, a coronary sinus access catheter (e.g., a standard angiographic catheter such as the modified Simmons-type angiographic catheter available from Cook Cardiology, Bloomington, Ind.) is initially inserted through a femoral vein or external jugular vein approach, using standard percutaneous catheter insertion technique. After such initial percutaneous catheter insertion has been accomplished, the PICAB procedure proceeds as follows:

First Step: Coronary Sinus Access/Introduction of First Guidewire:

As shown in FIG. 13$a$, an arterial blockage AB to be bypassed is located in the left anterior descending coronary artery (LAD). The coronary sinus access catheter 500 is advanced into the coronary sinus CS, as shown in FIG. 13$b$, to assist in the placement of a 0.035 inch diameter guidewire $GW_1$ into the great cardiac vein (GCV) and anterior interventricular vein (AIV). This guidewire $GW_1$ can be pre-loaded in the lumen of the coronary sinus access catheter 500 or can be advanced through the lumen of the coronary sinus access catheter 500 after it has been positioned inj the coronary sinus, as a separate step. Thereafter, the coronary sinus access catheter 500 is removed, leaving the 0.035 inch guidewire $GW_1$ in place.

Second Step: Introduction of Coronary Sinus Guide Catheter/AIV Access:

As shown in FIG. 13$c$-13$d$, the coronary sinus guide catheter 200 with introducer sheath 100 disposed within or through its lumen 202, is advanced over the 0.035 inch guidewire $GW_1$ until the tip of the coronary sinus guide catheter 200 is past the "mouth" of the coronary sinus. The introducer sheath 100 is then removed, leaving the coronary sinus guide catheter 200 in place, in the manner shown in FIG. 13$d$.

Third Step: Introduction & Aiming of Tissue-Penetrating Catheter:

As shown in FIG. 13$e$, the tissue-penetrating catheter 10 is then inserted over the pre-positioned 0.035 inch guidewire $GW_1$, through the lumen 202 of the coronary sinus guide catheter 200, and is advanced using fluoroscopy to a position distal to the arterial blockage AB being bypassed. The 0.035 inch guidewire $GW_1$ is then extracted and removed from the first lumen 14 of the tissue-penetrating catheter 10 and an IVUS imaging catheter (not shown) is then advanced through that first lumen 14 until the IVUS transducer resides within the hollow interior space of the orientation structure 36. The IVUS catheter is then used to receive a 360 degree ultrasound image from a vantage point within the interior space of the orientation structure 36. Such image enables the operator to see both the resident vessel (the AIV) and the target vessel (the LAD), as well as the reflections or artifacts from the three strut members 40, 42 &44 of the orientation structure 36. Because of the disparate distancing between the strut members 40, 42 &44, the reflections or artifacts produced by the strut members will form a generally "Y" shaped image as illustrated in FIGS. 2 and 3 of this patent application. The reflection $40_{Ref}$ produced by the first strut member 40 is clearly distinguishable from the reflections $42_{Ref}$, $44_{Ref}$ produced by the second and third strut members 42, 43, and provides an indication of the particular direction in which the needle member 30 will travel when advanced from the needle outlet opening 46 in the side of the catheter body 12. Thus, if the first strut member reflection $40_{Ref}$ observed on the IVUS image does not extend directly toward or into the lumen of the LAD (as illustrated in FIG. 3), the operator will rotate the tissue-penetrating catheter 10 until such first strut member reflection $40_{Ref}$ observed on the IVUS image does extend directly toward or into the lumen of the LAD (as illustrated in FIG. 2). This will ensure that the needle member 30 is properly aimed to enter the LAD when advanced.

Figure 13A:
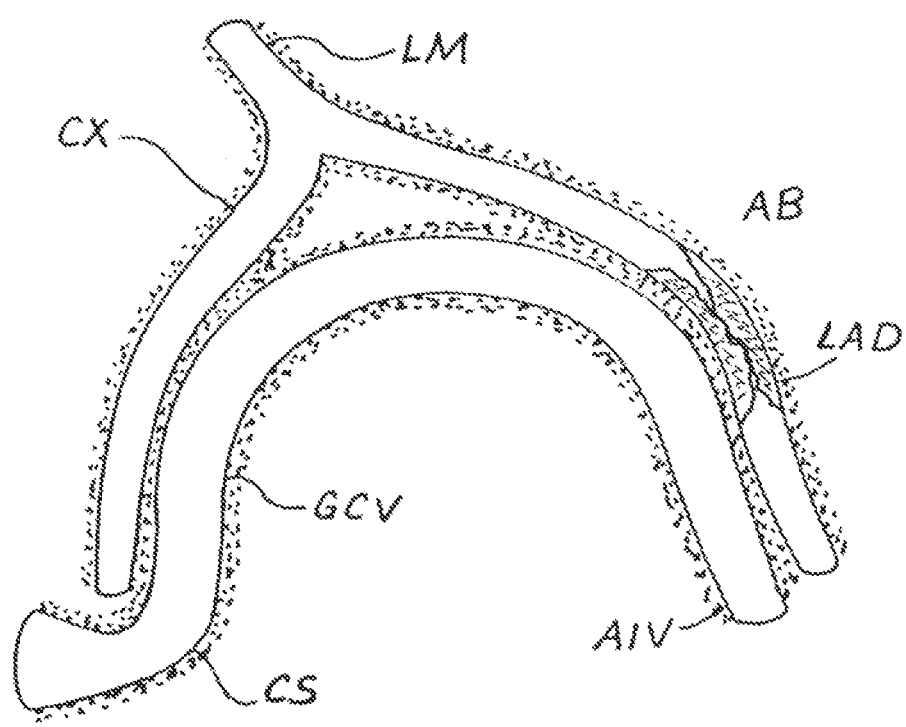
FIGS. 13a-13x are schematic, step-by-step showings of a preferred method for performing a percutaneous, in situ coronary arterio-venous bypass (PICAB) procedure to bypass a blockage in the proximal Left Anterior Descending coronary artery, using a vein-to-artery approach.
Figure 13H:
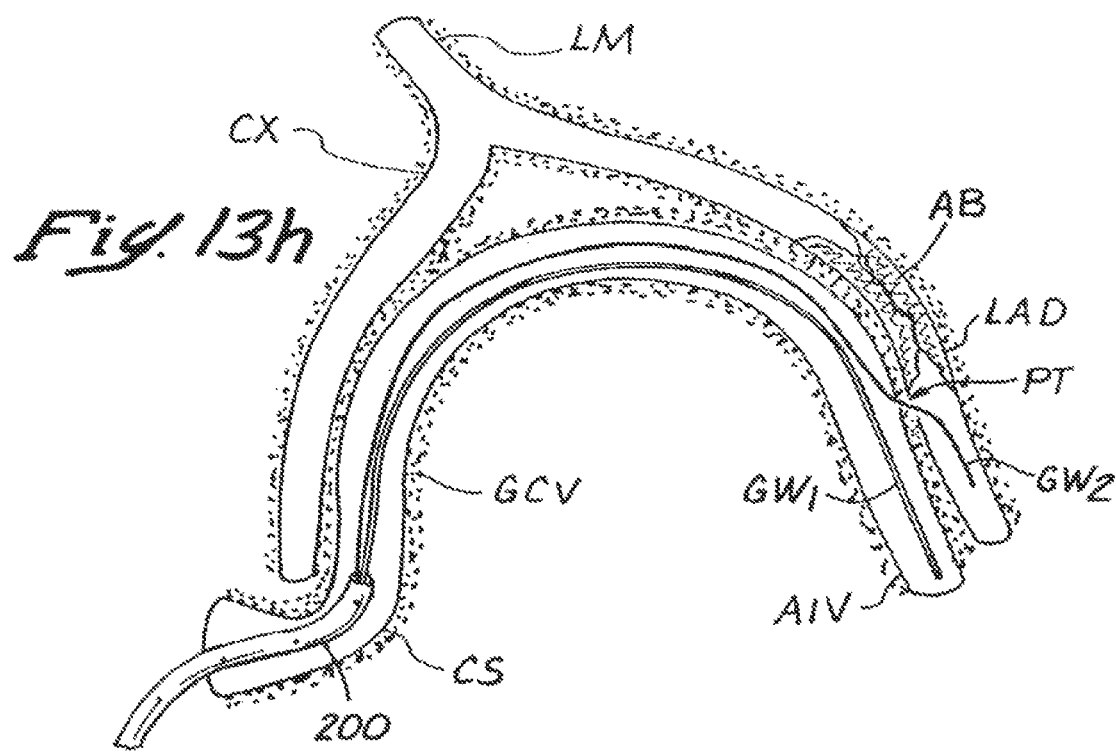
Figure 13I:
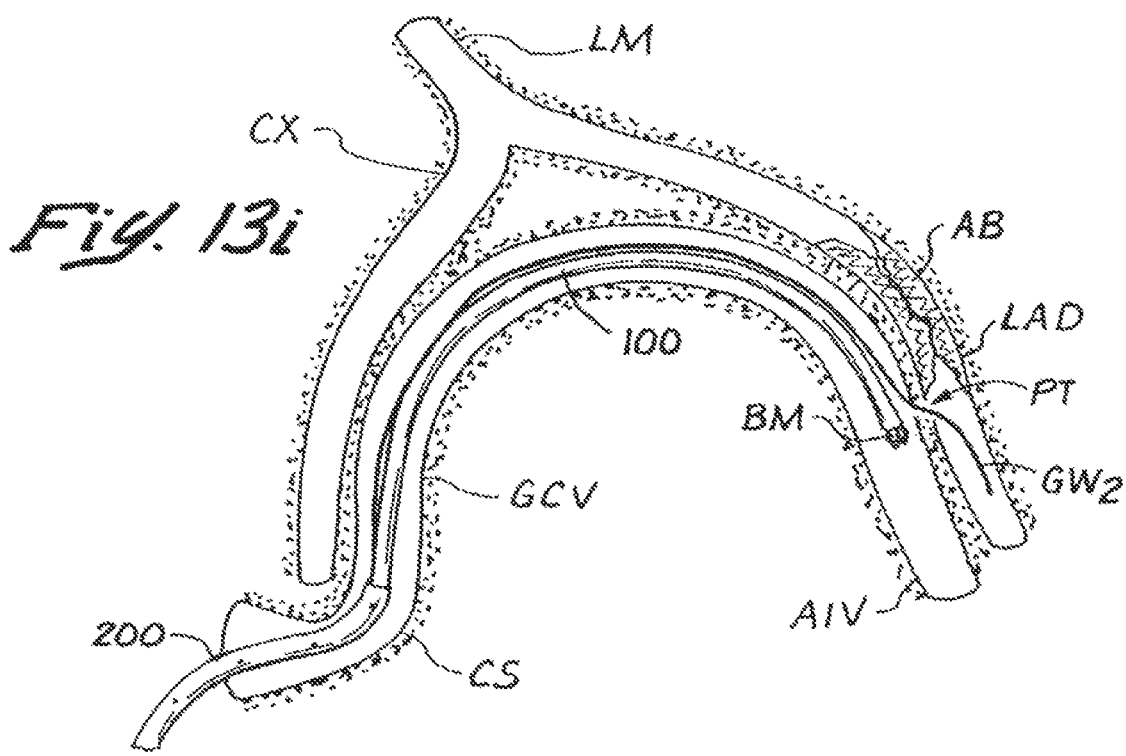
Figure 13J:
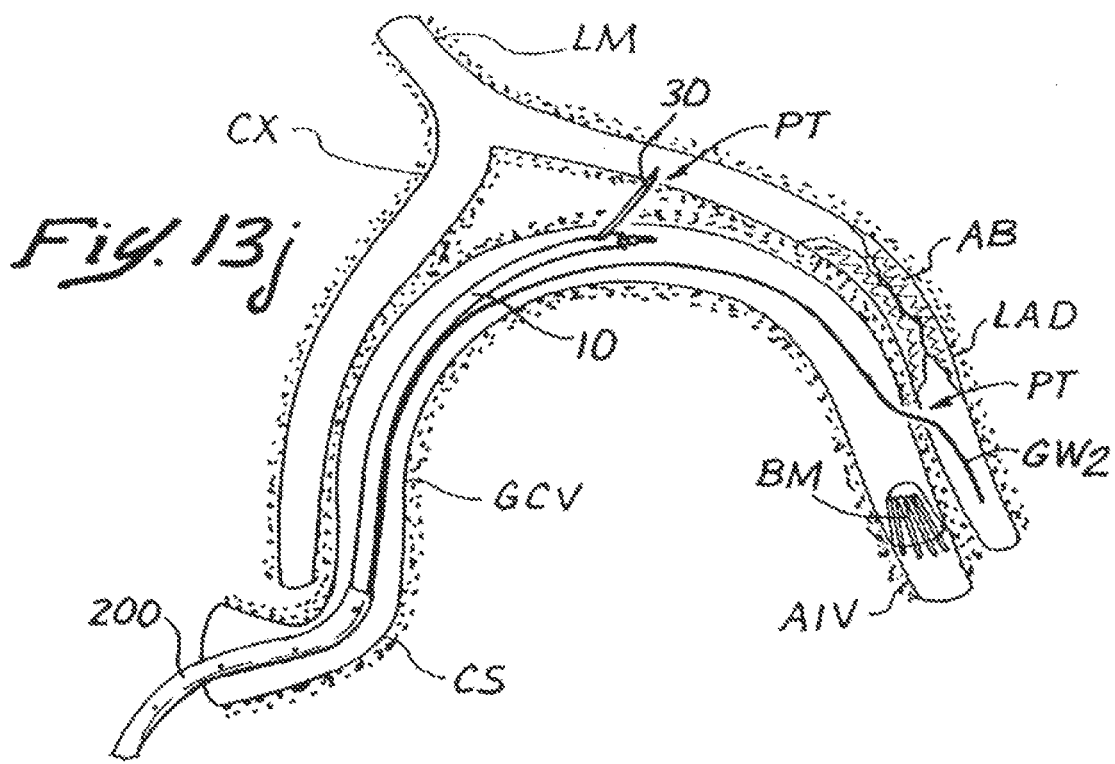
Figure 13K:
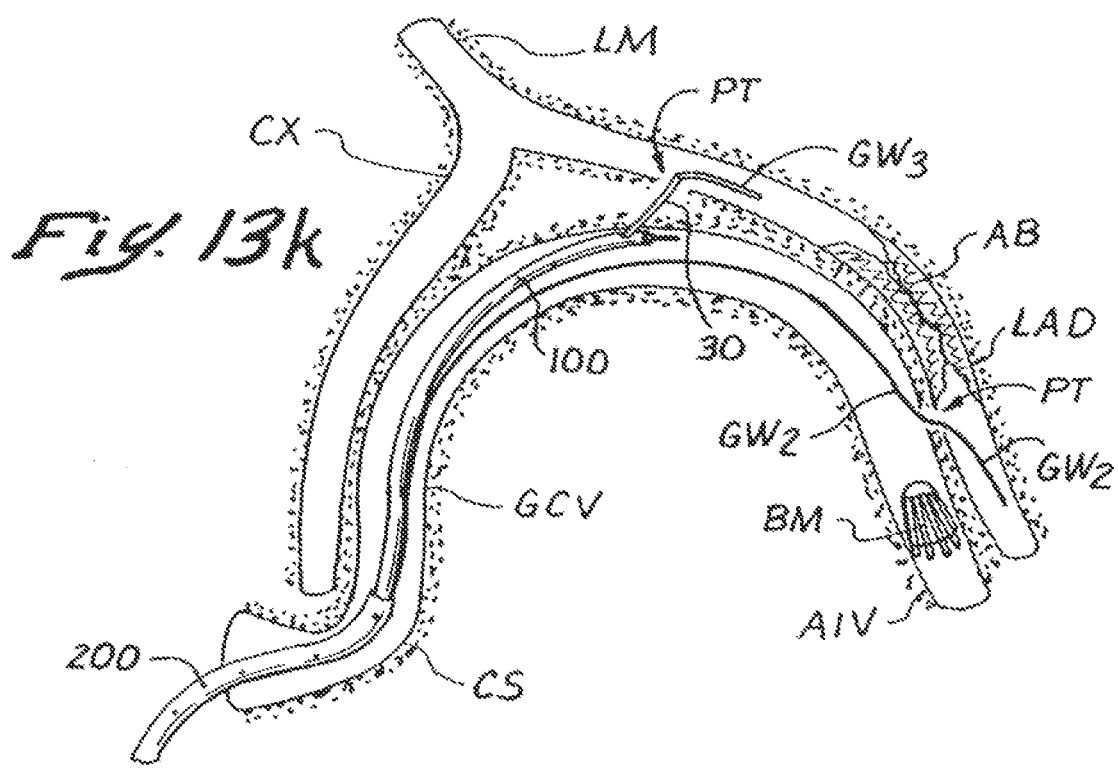

Fourth Step: Formation of Initial Arterio-Venous Penetration Tract Distal to Blockage:

As shown in FIG. 13f-13h, the tissue penetrating needle member 30 is then advanced in the distal direction to its extended position such that it punctures through the wall of the resident vessel (the AIV), through any tissue which may exist between the resident vessel (the AIV) and the target vessel (the LAD) and into the lumen of the target vessel (the LAD) at a location downstream of the arterial blockage AB. This maneuver results in the formation of an initial arterio-venous penetration tract PT. With the needle member 30 in its extended position and its distal tip in the lumen of the target vessel (the LAD), a 0.014 inch diameter guidewire $GW_2$ is inserted through the proximal port 27 of the tissue-penetrating catheter handpiece/needle controller 15 and advanced through the lumen 31 of the needle member 30 into the target vessel (the LAD), as shown in FIG. 14h.

After the 0.014 inch diameter guidewire $GW_2$ has been introduced into the target vessel (the LAD) the needle member 30 is withdrawn to its retracted position, leaving the 0.014 inch diameter guidewire $GW_2$ extending through the initially formed interstitial passageway into the target vessel (the LAD) as shown in FIG. 14h. After the needle member 30 is withdrawn to its retracted position, the tissue-penetrating catheter 10 is withdrawn and removed, leaving the 0.014 inch guidewire in place (i.e., extending through the newly formed arterio-venous penetration tract PT).

Fifth Step: Deployment of Blocker into Vein Lumen Distal to Blockage:

As shown in FIGS. 13 i-k, the subselective sheath 100 with its introducer 111 inserted therethrough is advanced through the coronary sinus guide 200 over the large guide wire $GW_1$. Thereafter, the introducer 111 and guidewire $GW_1$ are removed and one or more embolic blocker members BM are introduced into the proximal end of the subselective sheath, pushed through the lumen of the subselective sheath 100 using a pusher rod (not shown) and expelled into the lumen of the coronary vein (the AIV) where such embolic blocker(s) expand and engage the wall of the vein to cause substantial occlusion and blockage of bloodflow through the vein ath that location. Examples of such blocker members BM and their methods of implantation are described in U.S. patent application Ser. No. 09/117,156 The 0.035 inch diameter guidewire $GW_1$ is then removed, and an embolic blocker member BM is inserted into the proximal end of the subselective sheath. A push rod is then advanced through the lumen of the subselective sheath to push the embolic blocker member BM out of the distal end of the subselective sheath and into its desired position within the lumen of the coronary vein (the AIV). It is to be noted that this blocker deployment step may be performed at this point in the procedure, or alternatively may be delayed until a later time in the procedure. After the distal blocker member BM has been implanted at its desired location, the 0.035 inch diameter guidewire $GW_1$ is reinserted through the subselective sheath 100 and the subselective sheath 100 is then withdrawn and removed as shown in FIG. 13k.

Figure 13L:
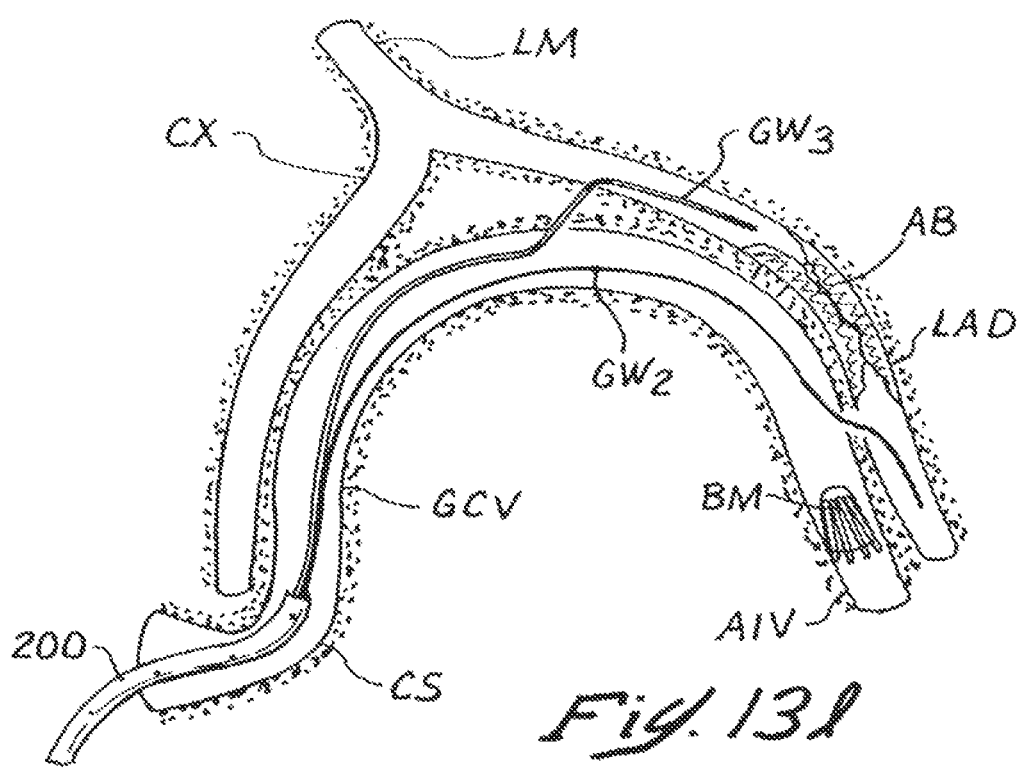
Figure 13M:
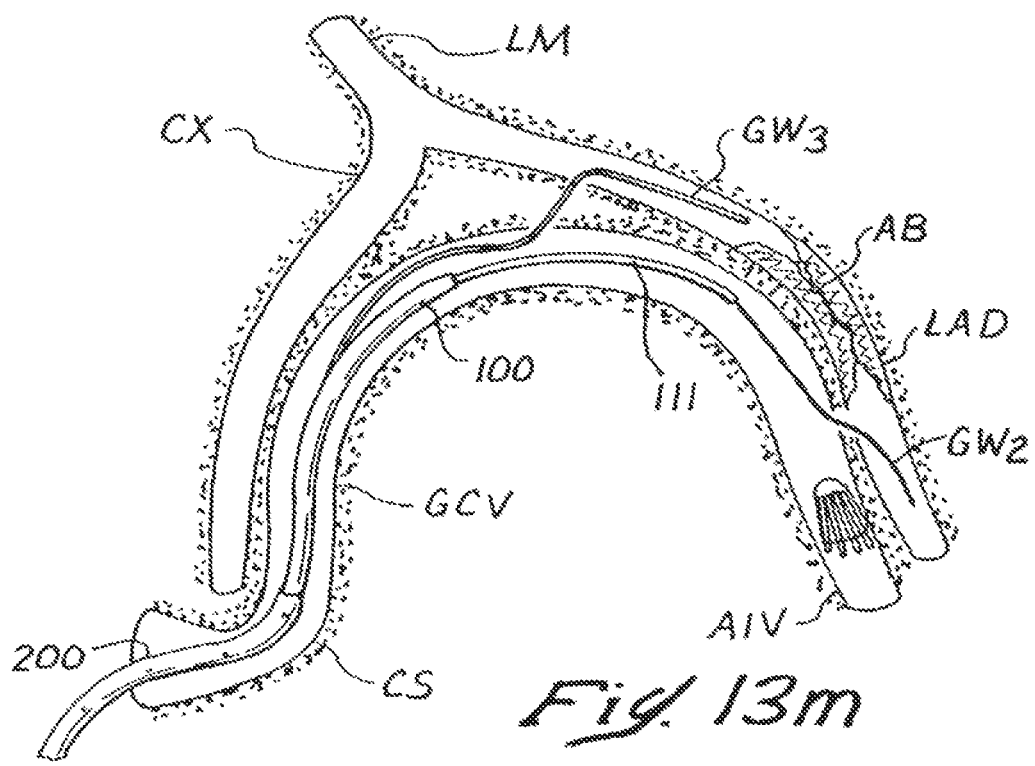
Figure 13N:
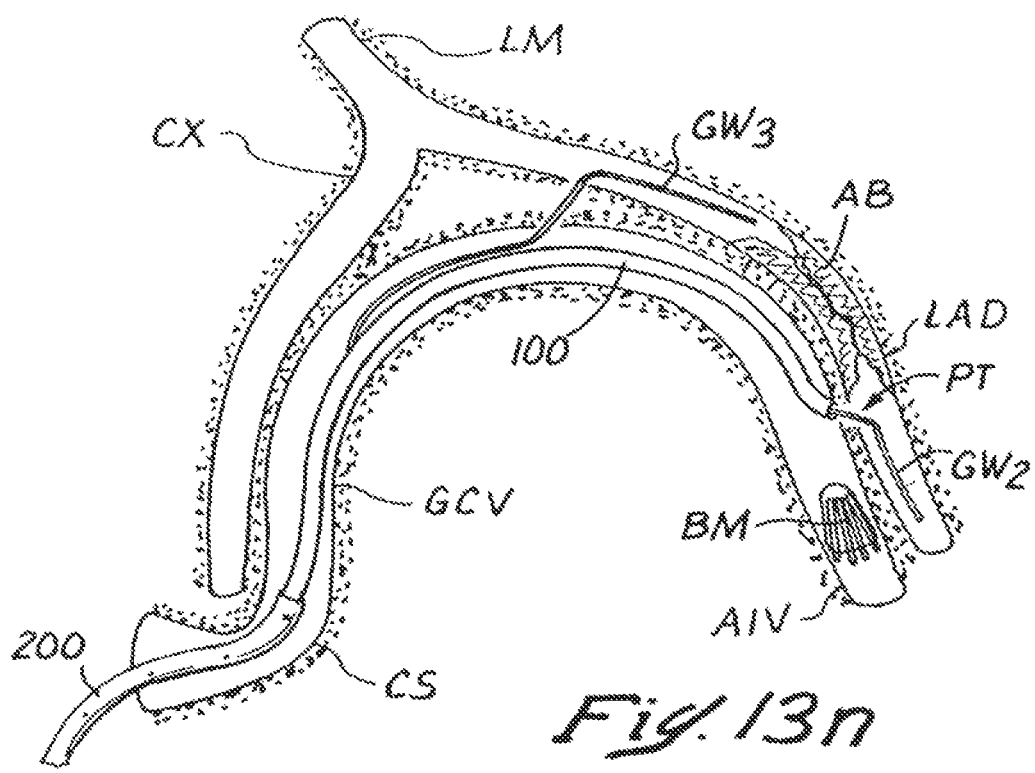

Sixth Step: Formation of Initial Arterio-Venous Penetration Tract Proximal to Blockage:

As shown in FIGS. 13l-13n, the tissue-penetrating catheter 10 is then once again advanced over the 0.035 inch diameter guidewire $GW_1$, under fluoroscopy, to a position that is proximal to the previously-formed distal penetration tract PT. The above-described fourth step is then repeated to form another initial arterio-venous penetration tract PT proximal to the blockage, and to pass a second 0.014 inch guidewire $GW_3$ through that second arterio-venous penetration tract PT. The tissue-penetrating catheter 10 is then withdrawn and removed, leaving both 0.014 inch guidewires $GW_1$ and $GW_3$ in place, in the manner shown in FIG. 13n.

Figure 13O:
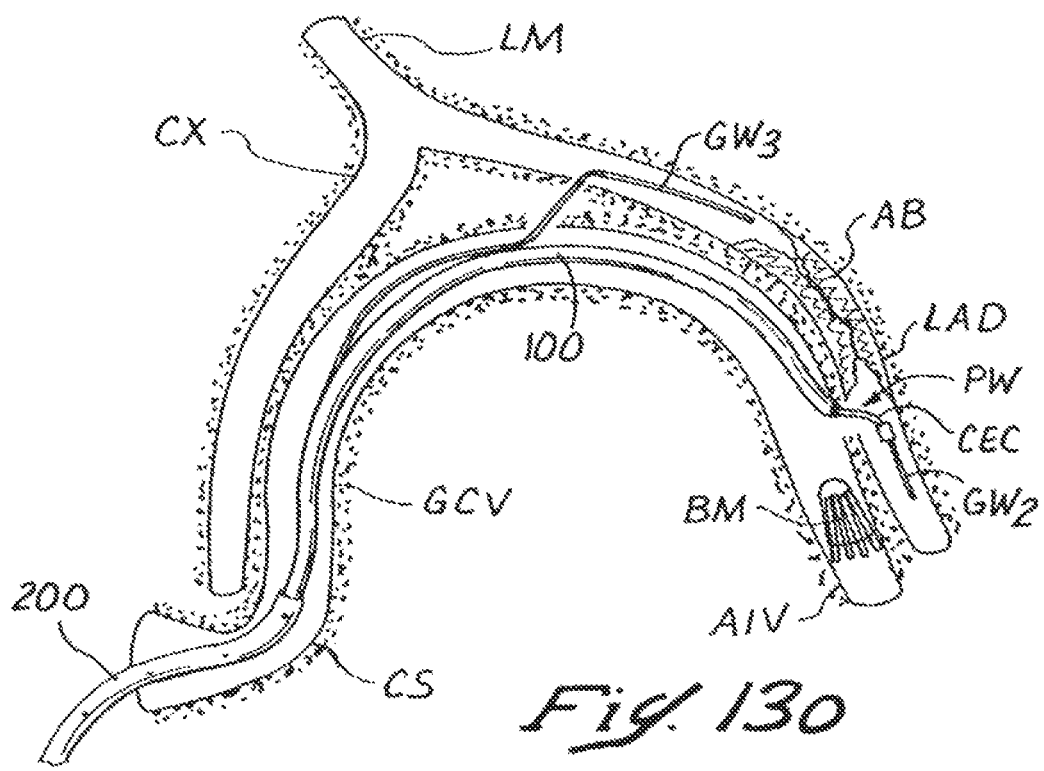
Figure 13P:
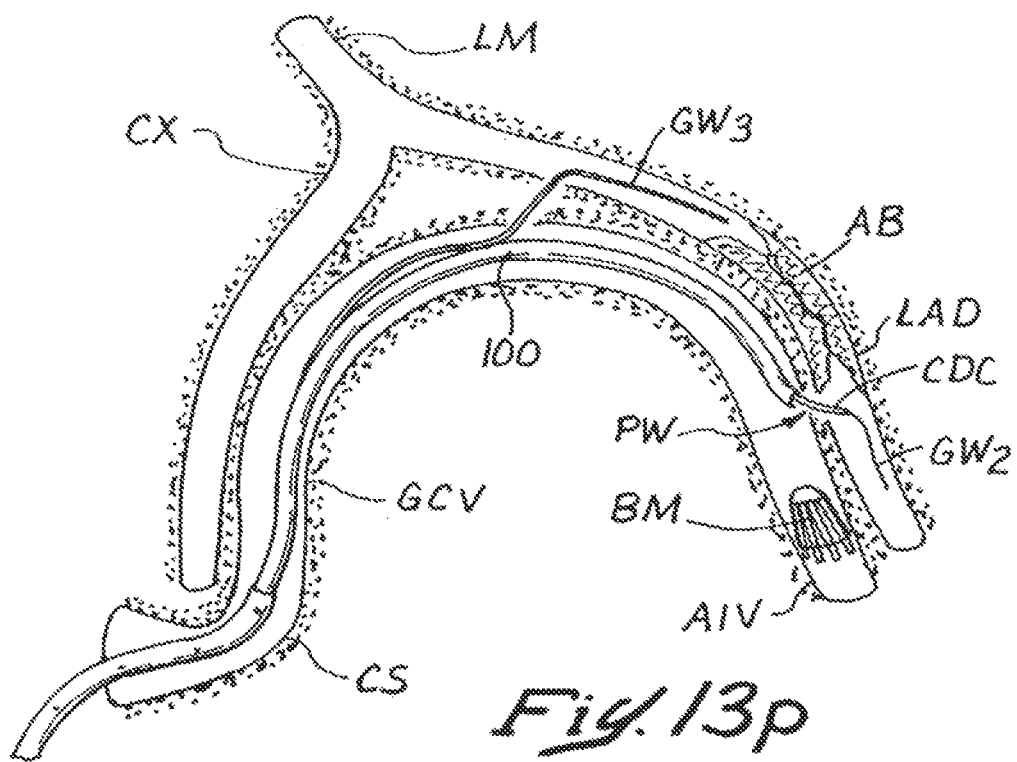

Seventh Step: Enlargement of Distal Penetration Tract to Form Arterio-Venous Bloodflow Passageway:

As shown in FIG. 13o, the subselective sheath 100 and its introducer 111 are advanced through the guide catheter 203, over the second guidewire GW2 to a location where the distal end of the subselective sheath 100 is within the AIV immediately adjacent the distal penetration tract PT. Thereafter, the introducer 111 is withdrawn and a channel enlarging catheter device CEC, of the type described in U.S. patent application Ser. No. 09/056,589, is advanced over the 0.014 inch guidewire $GW_2$ which extends through the distal arterio-venous penetration tract PT, thereby the dilating or enlarging that tract to form an arterio-venous bloodflow passageway PW. This step of the procedure provides control over the diameter or size of the arterio-venous bloodflow passageways PW and helps to ensure that the passageways PW will remain patent and functional following completion of the procedure. After such enlargement of the penetration tract to form the intended passageway PW, the channel enlarging catheter device CEC is withdrawn and removed along with the subselective sheath 100, leaving both 0.014 inch guidewires $GW_1$ and $GW_3$ in place, in the manner shown in FIG. 13p.

Figure 13Q:
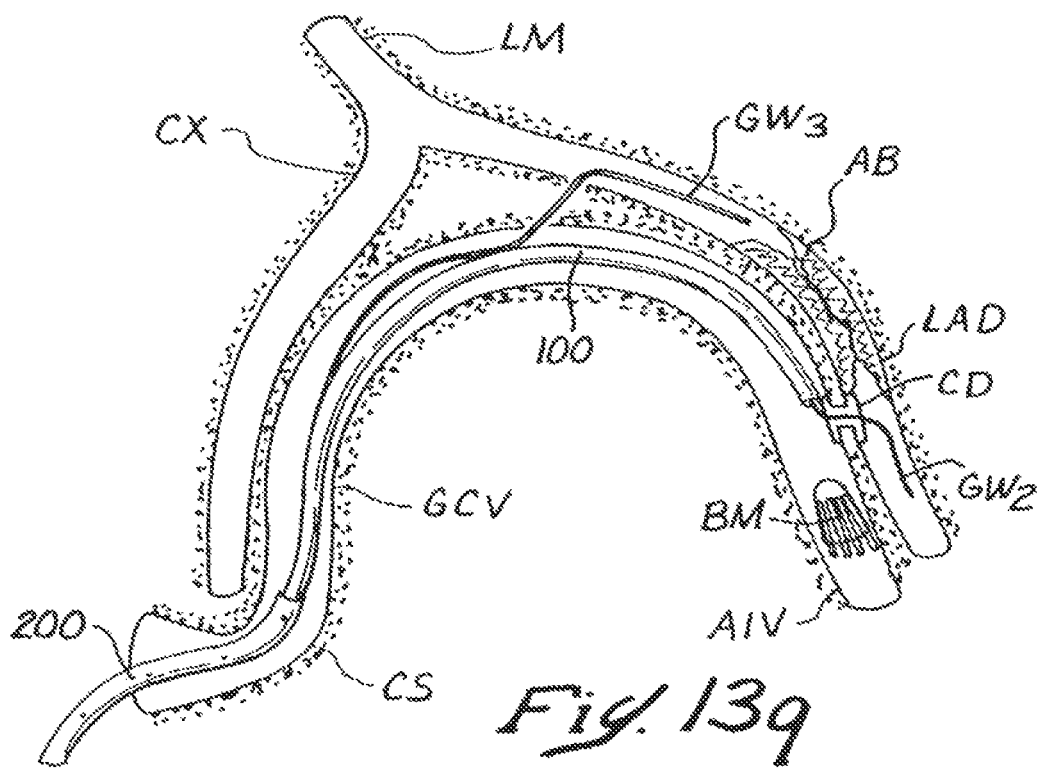

Eighth Step: Placement of Connector Device in Distal Arterio-Venous Bloodflow Passageway:

As an optional step, a connection device may be deployed in the passageway PW. As shown in FIGS. 13q-13s, the subselective sheath 100 and its introducer 111 are then advanced over the distal channel guidewire GW2 to a position where the distal end of the subselective sheath 100 is in the AIV immediately adjacent the distal bloodflow passageway PW. Thereafter, the introducer 111 is removed and a connector device delivery catheter CDC, of the type described in U.S. patent application Ser. No. 08/970,694, is advanced over through the subselective sheath 100 and over the 0.014 inch guidewire $GW_2$ which extends through the distal arterio-venous passageway PW, to implant a connector device CD within that passageway PW. The connector delivery catheter device CDC is then removed, along with the subselective sheath 100 and the distal 0.014 inch guidewire $GW_2$ that had extended through the distal arterio-venous passageway PW, leaving the distal connector device CD in place within the distal arterio-venous passageway PW in the manner shown in FIG. 13s.

Figure 13U:
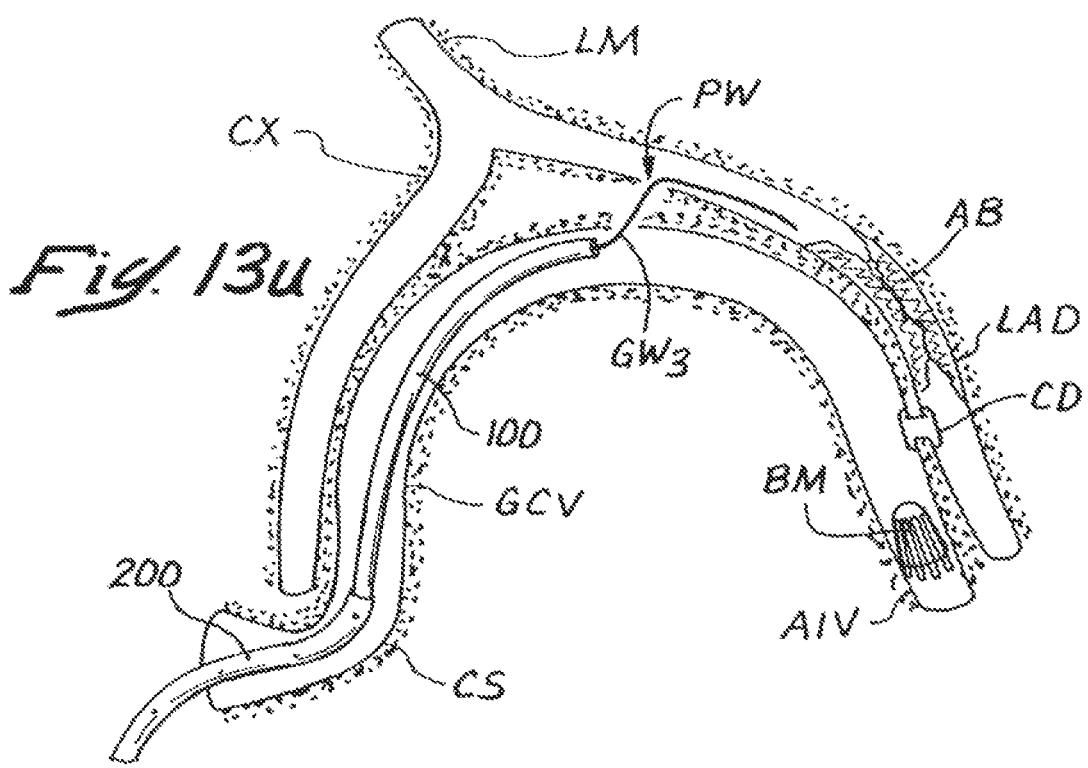

Ninth Step: Enlargement of Proximal Penetration Tract to form the Proximal Arterio-Venous Bloodflow Passageway:

As shown in FIGS. 13t-13u, the subselective sheath 100 and its introducer 111 are then advanced over the distal channel guidewire GW2 to a position where the distal end of the subselective sheath 100 is in the AIV immediately adjacent the distal bloodflow passageway PW. Thereafter, the introducer 111 is removed and a and a channel enlarging catheter device CEC, of the type described in U.S. patent application Ser. No. 09/056,589, is advanced over the 0.014 inch guidewire $GW_3$ that extends through the proximal arterio-venous penetration tract PT, thereby the dilating or enlarging that tract to form a proximal arterio-venous bloodflow passageway PW. This step of the procedure provides control over the diameter or size of the arterio-venous bloodflow passageways PW and helps to ensure that the passageways PW will remain patent and functional following completion of the procedure. After such enlargement of the proximal penetration tract to form the intended passageway PW, the channel enlarging catheter device CEC is withdrawn and removed leaving the subselective sheath 100 and proximal 0.014 inch guidewire $GW_3$ in place, as shown in FIG. 13u.

Figure 13V:
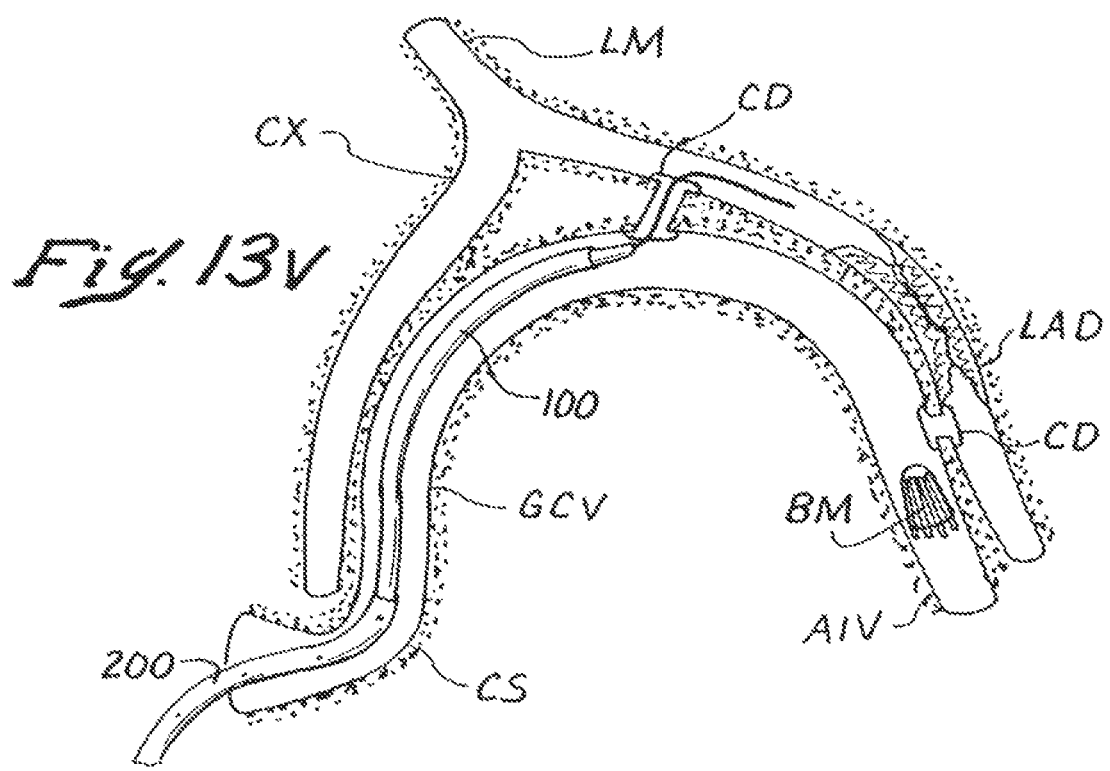

Tenth Step: Placement of Connector Device in Proximal Arterio-Venous Passageway:

As an optional step, a connection device may be deployed in the passageway PW. As shown in FIG. 13v, a connector device delivery catheter CDC, of the type described in U.S. patent application Ser. No. 08/970,694, is then advanced through the subselective sheath 100 and over the 0.014 inch guidewire $GW_3$ which extends through the proximal arterio-venous passageway PW, to implant a connector device CD within that passageway PW. The connector delivery catheter device is then removed, and the subselective sheath 100 and 0.014 inch guidewire $GW_3$ are then retracted to a position within the Great Cardiac Vein GCV, proximal to the proximal passageway PW, as shown in FIG. 13w, leaving the proximal connector device CD in place within the proximal arterio-venous passageway.

Eleventh Step: Deployment of Blocker into Vein Lumen Proximal to Blockage:

As shown in FIG. 13w, the above-described fifth step is then repeated to implant a second blocker device BD within the lumen of the Great Cardiac Vein (GCV), proximal to the proximal arterio-venous passageway PW. This completes the procedure, and results in the flow of arterial blood from the Circumflex Artery (CX), through the proximal arterio-venous passageway PW, through the Great Cardiac Vein GCV and Anterior Interventricular Vein in the retrograde direction, through the distal arterio-venous passageway PW, and into the Left Anterior Descending coronary artery LAD, downstream of the blockage AB, as illustrated by the flow-indicating arrows on FIG. 13x.

Figure 14A:
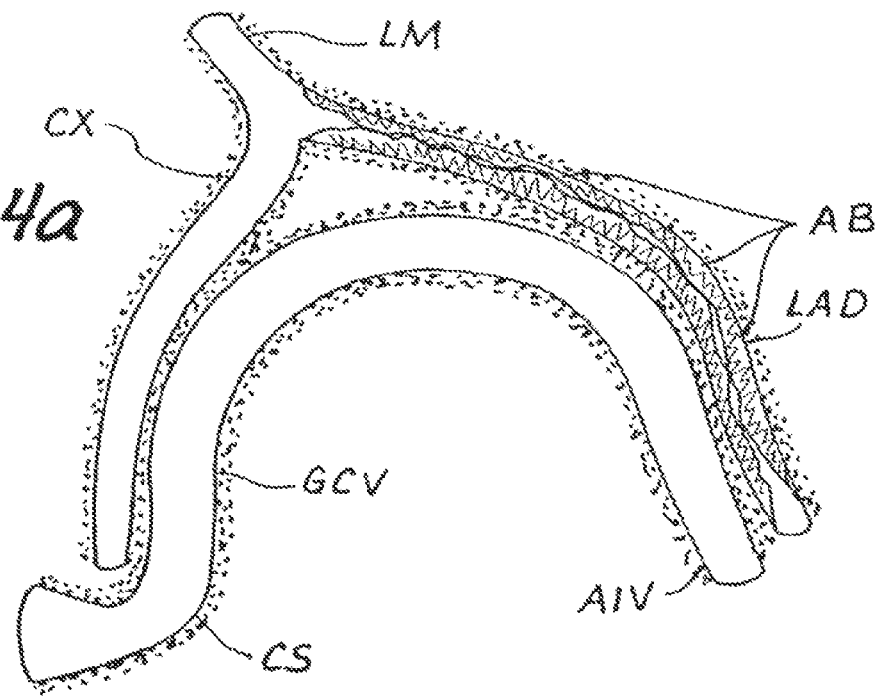
Figure 14B:
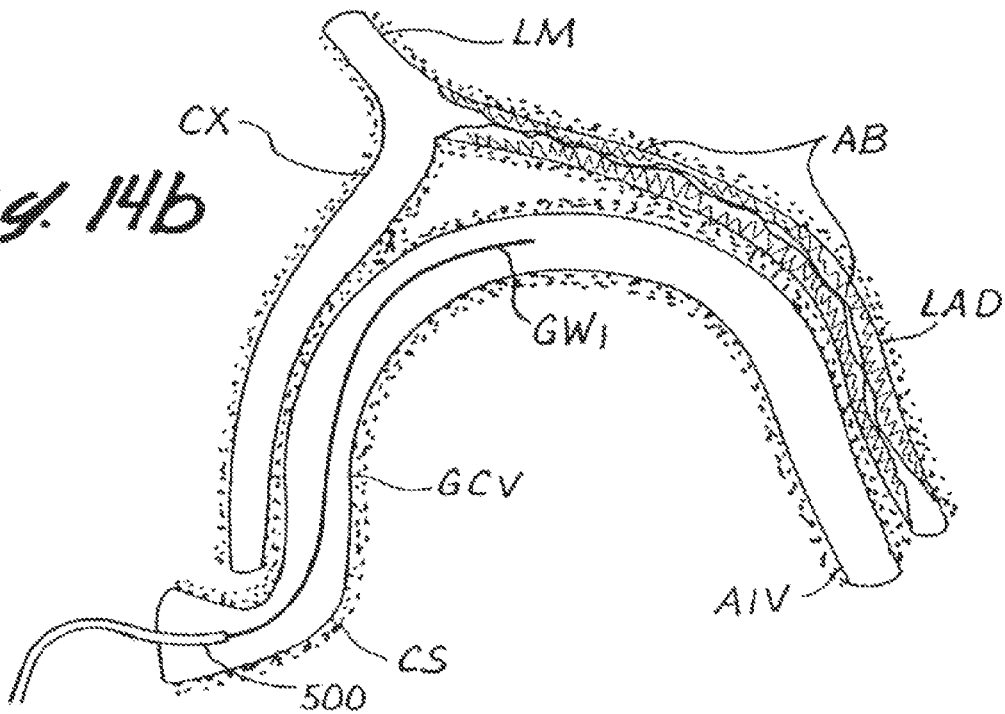

II. A Preferred Method for Performing the PICVA Procedure:

FIGS. 14a-14l show, in step-by-step fashion, an example of a PICVA procedure wherein the catheter system 10 of the present invention is used for the purpose causing arterial blood to be rerouted into the Anterior Interventricular Vein and caused to subsequently flow through the AIV in retrograde fashion (i.e., in a direction opposite normal venous return) thereby bypassing an extensive blockage within the patient's Anterior Descending Coronary Artery (LAD) and perfusing the region of myocardium that had been rendered ischemic due to the extensive blockage in the LAD. In this PIVA procedure, a coronary sinus access catheter (e.g., a standard angiographic catheter such as the modified Simmons-type angiographic catheter available from Cook Cardiology, Bloomington, Ind.) is initially inserted through a femoral vein or external jugular vein approach, using standard percutaneous catheter insertion technique. After such initial percutaneous catheter insertion has been accomplished, the PICAB procedure proceeds as follows:

First Step: Coronary Sinus Access/Introduction of First Guidewire:

As shown in FIG. 14a, an extensive arterial blockage AB extends though substantially the entire length of the left anterior descending coronary artery (LAD), thereby rendering this patient an unlikely candidate for the above-described PICAB procedure because no patent distal portion of the LAD remains available to receive the bypass arterial bloodflow. It is appreciated that in cases where the disease AB does not extend into the proximal portion of the LAD, a connection may be established between the LAD and the AIV proximal to the blockage, but there would be no opportunity to make a distal connection as required by the PICAB procedure. As shown in FIG. 14b, a coronary sinus access catheter 500 is advanced into the coronary sinus CS to assist in the placement of a 0.035 inch diameter guidewire $GW_1$ into the great cardiac vein (GCV). This guidewire $GW_1$ can be pre-loaded in the lumen of the coronary sinus access catheter 500 or can be advanced through the lumen of the coronary sinus access catheter 500 after it has been positioned in the coronary sinus, as a separate step. Thereafter, the coronary sinus access catheter 500 is removed, leaving the 0.035 inch guidewire $GW_1$ in place.

Second Step: Introduction of Coronary Sinus Guide Catheter/AIV Access:

As shown in FIG. 14c-14d, the coronary sinus guide catheter 200 with introducer sheath 100 disposed within or through its lumen 202, is advanced over the 0.035 inch guidewire $GW_1$ until the tip of the coronary sinus guide catheter 200 is past the "mouth" of the coronary sinus. The introducer sheath 100 is then removed, leaving the coronary sinus guide catheter 200 in place, in the manner shown in FIG. 14d.

Figure 14E:
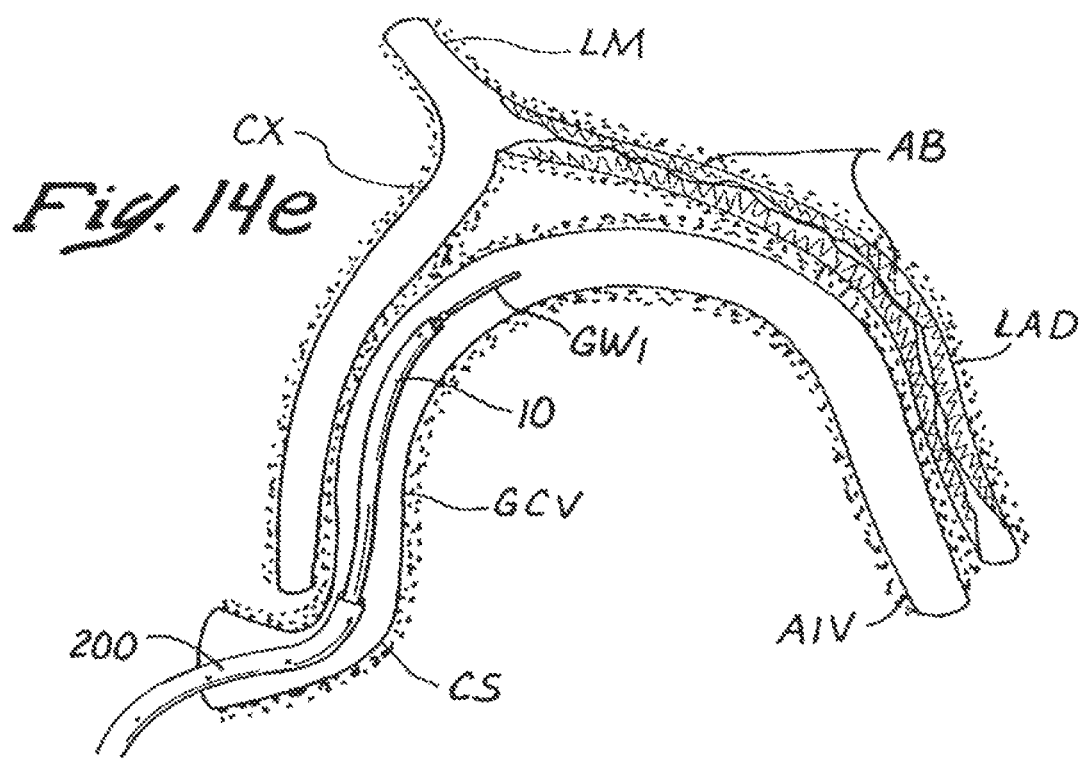

Third Step: Introduction & Aiming of Tissue-Penetrating Catheter:

As shown in FIG. 14e, the tissue-penetrating catheter 10 is then inserted over the pre-positioned 0.035 inch guidewire $GW_1$, through the lumen 202 of the coronary sinus guide catheter 200, and is advanced using fluoroscopy to a position proximal to the arterial blockage AB being bypassed. The 0.035 inch guidewire $GW_1$ is then extracted and removed from the first lumen 14 of the tissue-penetrating catheter 10 and an IVUS imaging catheter (not shown) is then advanced through that first lumen 14 until the IVUS transducer resides within the imaging catheter-receiving space of the orientation structure 36. The IVUS catheter is then used to receive a 360 degree ultrasound image from a vantage point within the interior space of the orientation structure 36. Such image enables the operator to see both the resident vessel (the GCV) and the target vessel (the CX), as well as the reflections or artifacts from the three strut members 40, 42 &44 of the orientation structure 36. Because of the disparate distancing between the strut members 40, 42 &44, the reflections or artifacts produced by the strut members will form a generally "Y" shaped image as illustrated in FIGS. 2 and 3 of this patent application. The reflection $40_{Ref}$ produced by the first strut member 40 is clearly distinguishable from the reflections $42_{Ref}$, $44_{Ref}$ produced by the second and third strut members 42, 43, and provides an indication of the particular direction in which the needle member 30 will travel when advanced from the needle outlet opening 46 in the side of the catheter body 12. Thus, if the first strut member reflection $40_{Ref}$ observed on the IVUS image does not extend directly toward or into the lumen of the CX (as illustrated in FIG. 3), the operator will rotate the tissue-penetrating catheter 10 until such first strut member reflection $40_{Ref}$ observed on the IVUS image does extend directly toward or into the lumen of the CX (as illustrated in FIG. 2). This will ensure that the needle member 30 is properly aimed to enter the CX when advanced.

Figure 14F:
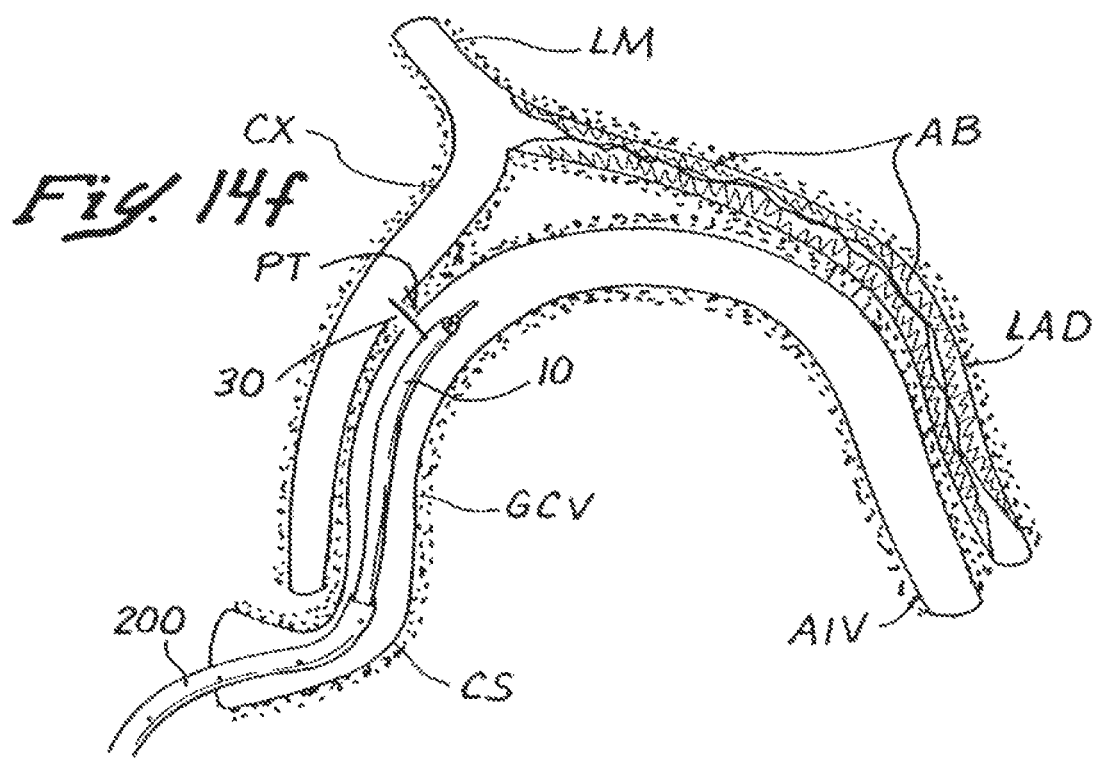

Fourth Step: Formation of Initial Arterio-Venous Penetration Tract Distal to Blockage:

As shown in FIG. 14*f*-14*h*, the tissue penetrating needle member 30 is then advanced in the distal direction to its extended position such that it punctures through the wall of the resident vessel (the GCV), through any tissue which may exist between the resident vessel (the GCV) and the target vessel (the CX) and into the lumen of the target vessel (the CX) at a location downstream of the arterial blockage AB. This maneuver results in the formation of an initial arterio-venous penetration tract PT. With the needle member 30 in its extended position and its distal tip in the lumen of the target vessel (the CX), a 0.014 inch diameter guidewire $GW_2$ is inserted through the proximal port 27 of the tissue-penetrating catheter handpiece/needle controller 15 and advanced through the lumen 31 of the needle member 30 into the target vessel (the CX), as shown in FIG. 14*h*. After the 0.014 inch diameter guidewire $GW_2$ has been introduced into the target vessel (the LAD) the needle member 30 is withdrawn to its retracted position, leaving the 0.014 inch diameter guidewire $GW_2$ extending through the initially formed interstitial passageway into the target vessel (the CX) as shown in FIG. 14*h*. Thereafter, the needle member 30 is withdrawn to its retracted position and the tissue-penetrating catheter 10 is withdrawn and removed, leaving the 0.014 inch guidewire in place (i.e., extending through the newly formed arterio-venous penetration tract PT), as shown in FIG. 14*h*.

Figure 14I:
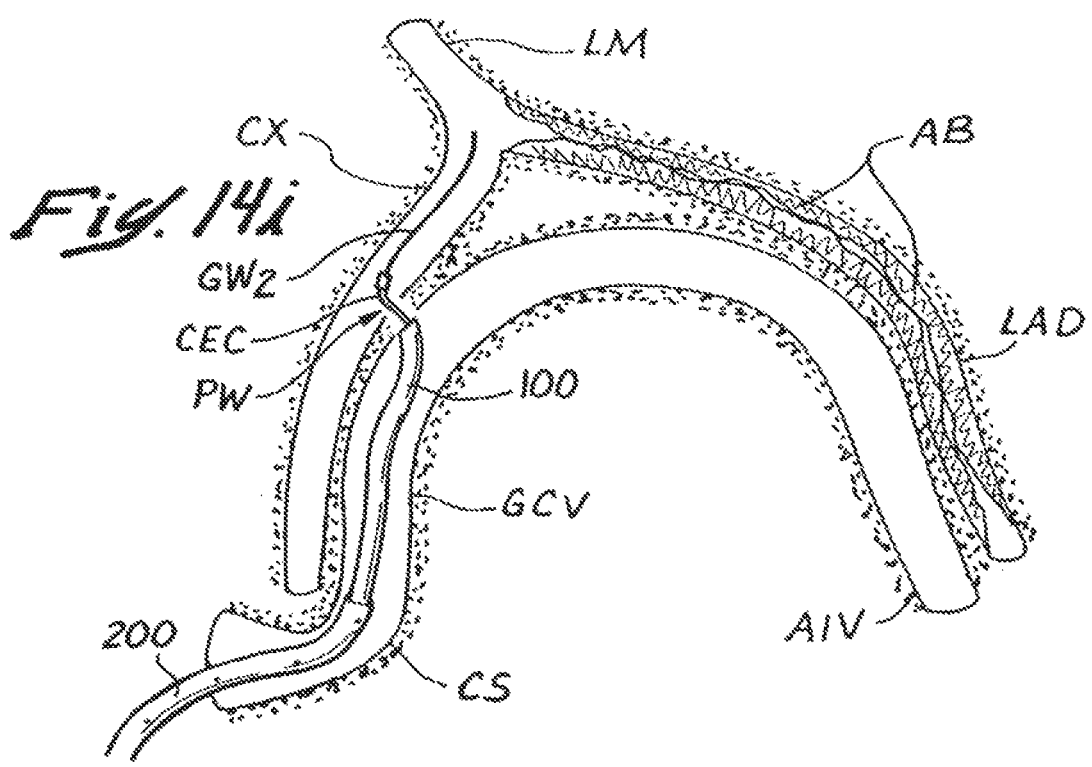

Fifth Step: Enlargement of Penetration Tract to Form Arterio-Venous Bloodflow Passageway:

As shown in FIG. 14*i*, the subselective sheath 100 and its introducer 111 are advanced through the guide catheter 203, over the second guidewire GW2 to a location where the distal end of the subselective sheath 100 is within the AIV immediately adjacent the distal penetration tract PT. Thereafter, the introducer 111 is withdrawn and a channel enlarging catheter device CEC, of the type described in U.S. patent application Ser. No. 09/056,589, is advanced over the 0.014 inch guidewire $GW_2$ which extends through the arterio-venous penetration tract PT, thereby the dilating or enlarging that tract to form an arterio-venous bloodflow passageway PW. This step of the procedure provides control over the diameter or size of the arterio-venous bloodflow passageways PW and helps to ensure that the passageways PW will remain patent and functional following completion of the procedure. After such enlargement of the penetration tract to form the intended passageway PW, the channel enlarging catheter device CEC is withdrawn and removed, leaving the subselective sheath 100 and second guidewire $GW_2$ in place.

Figure 14J:
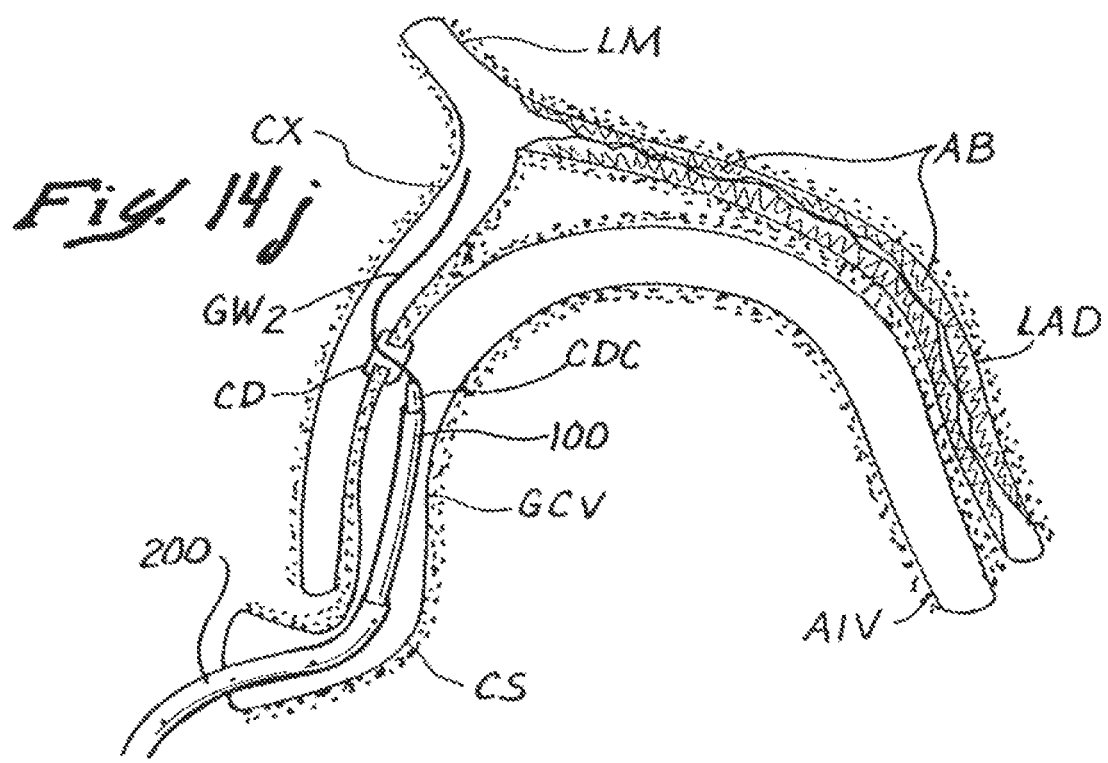
Figure 14K:
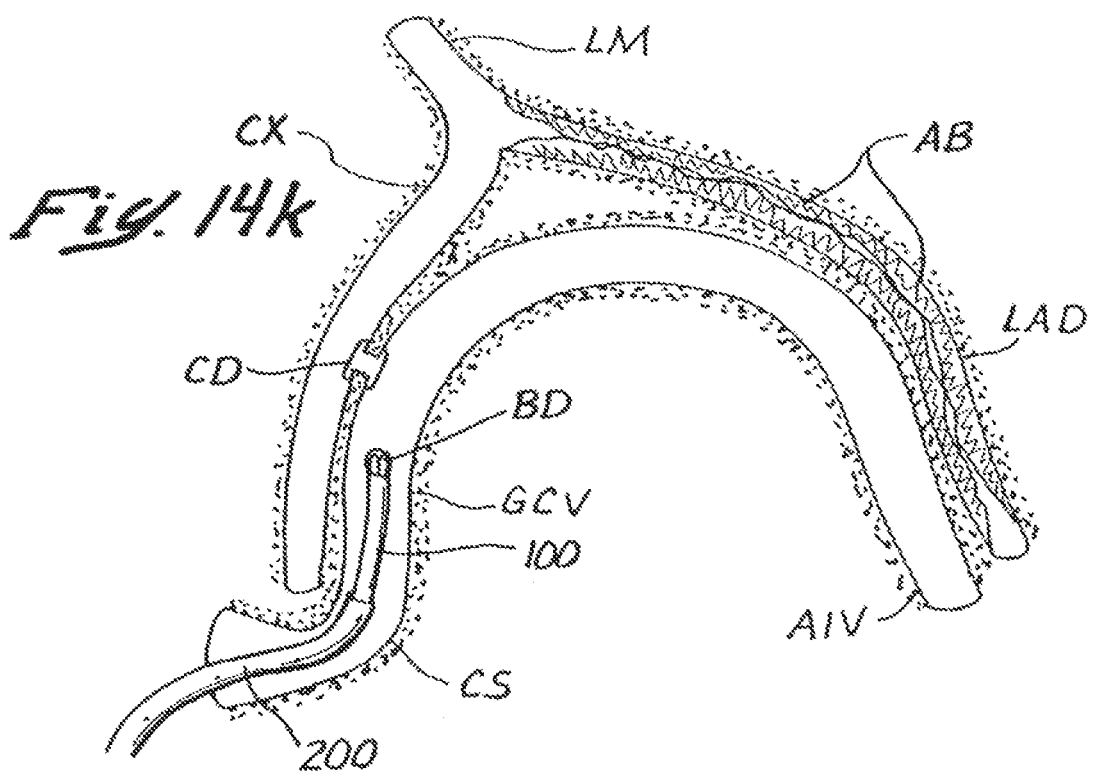

Sixth Step: Placement of Connector Device in Arterio-Venous Bloodflow Passageway:

It may be desirable, in an optional step as shown in FIGS. 14*j*-14*k*, to place a connector device within the passageway PW. A connector device delivery catheter CDC, of the type described in U.S. patent application Ser. No. 08/970,694, is advanced over through the subselective sheath 100 and over the 0.014 inch guidewire $GW_2$ which extends through the arterio-venous passageway PW, to implant a connector device CD within that passageway PW. The connector delivery catheter device CDC is then removed, and the subselective sheath 100 and the 0.014 inch guidewire $GW_2$ that had extended through the distal arterio-venous passageway PW are then retracted to a position proximal to the passageway PW.

Figure 14L:
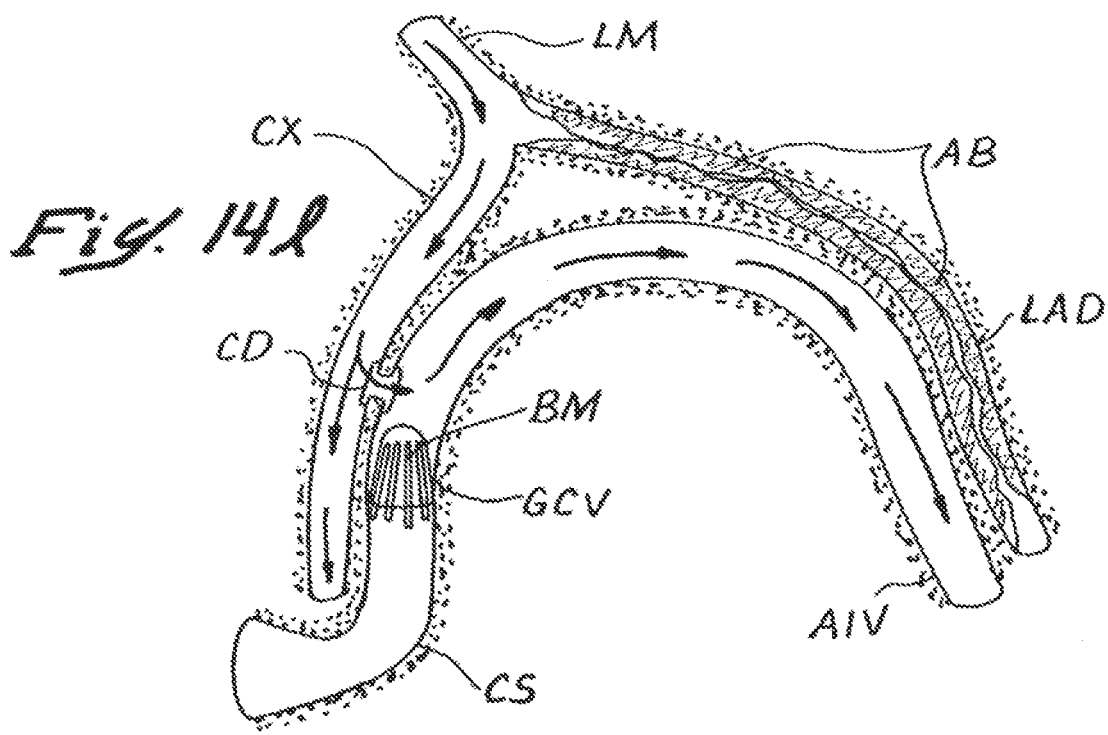

Seventh Step: Deployment of Blocker into Vein Lumen Proximal to Blockage:

As shown in FIG. 14*l*, the guidewire $GW_2$ is then removed and one or more embolic blocker members BM are introduced into the proximal end of the subselective sheath 100, pushed through the lumen of the subselective sheath 100 using a pusher rod (not shown) and expelled into the lumen of the Great Cardiac Vein (GCV) proximal to the bloodflow passageway PW where such embolic blocker(s) expand and engage the wall of the vein to cause substantial occlusion and blockage of bloodflow through the vein at that location. Examples of such blocker members BM and their methods of implantation are described in U.S. patent application Ser. No. 09/117,516. The 0.035 inch diameter guidewire $GW_1$ is then removed, and an embolic blocker member BM is inserted into the proximal end of the subselective sheath. A push rod is then advanced through the lumen of the blocker delivery catheter to push the embolic blocker member BM out of the distal end of the subselective sheathand into its desired position within the lumen of the coronary vein (the GCV). It is to be noted that this blocker deployment step may be performed at this point in the procedure, or alternatively may be delayed until a later time in the procedure. This completes the procedure, and results in the flow of arterial blood from the Circumflex Artery (CX), through the arterio-venous passageway PW, through the Great Cardiac Vein GCV and Anterior Interventricular Vein in the retrograde direction so as to perfuse the myicardium that has been rendered ischemic due to the blockage of the Left Anterior Decending coronary arter (LAD) as illustrated by the flow indicating arrows on FIG. 14*l*.

It is to be understood and appreciated that the invention has been described herein with reference to certain presently preferred embodiments and examples only, and no effort has been made to exhaustively describe all possible embodiments and examples of the invention. Indeed, as those killed in the art will appreciate, various additions, deletions, modifications and variations may be made to the particular embodiments and examples described hereabove without departing from the intended spirit and scope of the invention. For example, where this patent application has listed the steps of a method or procedure in a specific order, it may be possible (or even expedient in certain circumstances) to change the order in which some steps are performed, and it is intended that the particular steps of the method or procedure claims set forth herebelow not be construed as being order-specific unless such order specificity is expressly stated in the claim. Another example is that, although the specific procedures described in detail in this application involve penetrating through tissue located within an "acceptable penetration zone," such acceptable penetration zone need not be occupied by tissue but rather such acceptable penetration zone may fully or partially comprise an open space such as a body cavity or void. Accordingly, it is intended that all such additions, deletions, modifications and variations be included within the scope of the following claims.

What is claimed is:

1. A tissue penetrating catheter device useable to penetrate outwardly from a blood vessel lumen in which the tissue penetrating catheter device is positioned to a target location outside of that blood vessel lumen, said tissue penetrating catheter device comprising:

i) a flexible catheter body which is insertable into the blood vessel lumen, said catheter body having a side wall, a distal end and an outlet opening formed in the side wall thereof;

ii) an first lumen through which a separate imaging catheter may be inserted;

iii) a second lumen which extends through said outlet opening;

iv) a tissue penetrating member disposed within said second lumen and advanceable out of said outlet opening; and, v) an orientation structure positioned on the catheter body, said orientation structure having a) an imaging catheter receiving space formed therein in alignment with said first lumen and b) at least one marker member located on one side of the imaging catheter receiving space, said at least one marker member being positioned and constructed to create, on an image display received from an imaging catheter positioned within the imaging catheter receiving space, an indication of the path that will be followed by the tissue penetrating member when the tissue penetrating member is advanced from the catheter body.

2. A device according to claim 1 wherein the orientation structure comprises a plurality of strut members and wherein said at least one marker member comprises one of said strut members.

3. A device according to claim 2 wherein an imaging catheter which images a 360 degree field, when positioned in the imaging catheter receiving space, will image all of said plurality of strut members, but an image of the strut member which comprises the at least one marker member will be distinguishable from images of the other strut members.

4. A device according to claim 2 wherein the plurality of strut members extend longitudinally at circumferentially spaced-apart locations about the imaging catheter receiving space with the strut member that comprises the at least one marker member being aligned with the outlet opening out of which the tissue penetrating member advances.

5. A device according to claim 2 wherein, when an ultrasound imaging catheter, when positioned in the imaging catheter receiving space and used to image the plurality of strut members, the strut member that comprises the at least one marking member produces an ultrasound image which is distinguishable from ultrasound images produced by the other strut members.

6. A device according to claim 2 wherein the strut member that comprises the at least one marking member is distinguishable from the other strut members because it is uniquely spaced away from the other strut members.

7. A device according to claim 1 wherein a distal end opening is formed distal of the catheter receiving space so that an imaging catheter may be advanced distally out of the catheter receiving space and beyond the distal end of the penetrating catheter.

8. A device according to claim 1 further comprising a soft tip on the distal end of the catheter body.

9. A device according to claim 1 further comprising a tissue penetrating member stabilizer which prevents or deters the tissue penetrating member from rotating or deviating from a predetermined acceptable penetration zone as it is advanced out of the outlet opening.

10. A device according to claim 9 wherein the tissue penetrating member is elastically deformable and biased to a preformed curved configuration and wherein the tissue penetrating member stabilizer comprises a curved needle housing which mates with the preformed curved configuration of the tissue penetrating member thereby deterring unwanted rotation and resultant lateral deviation of the tissue penetrating member as it advances out of the outlet opening.

11. A device according to claim 9 wherein the tissue penetrating member stabilizer comprises frictionally engaged surfaces formed on the tissue penetrating member and the surrounding catheter body to rotationally lock or deter rotation of the tissue penetrating member relative to the catheter body.

12. A device according to claim 9 wherein the tissue penetrating member is elastically deformable and biased to a preformed curved configuration and wherein the tissue penetrating member stabilizer comprises a steering mechanism for causing a distal portion of the catheter body to become curved in the direction in which the tissue penetrating member is intended to advance so as to cause the preformed curve of the tissue penetrating member to mate with the induced curvature of the distal portion of the catheter body.

13. A device according to claim 9 wherein the tissue penetrating member stabilizer comprises a needle guide member that is deployable from a side of the tissue penetrating catheter adjacent to the outlet opening through to support and prevent unwanted lateral movement of the tissue penetrating member as it is advanced out of the outlet opening.

* * * * *